United States Patent
Higuchi

(10) Patent No.: US 12,262,939 B2
(45) Date of Patent: Apr. 1, 2025

(54) LESION RESECTION METHOD

(71) Applicant: OLYMPUS CORPORATION, Hachioji (JP)

(72) Inventor: Tatsuya Higuchi, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 712 days.

(21) Appl. No.: 17/575,183

(22) Filed: Jan. 13, 2022

(65) Prior Publication Data

US 2023/0218336 A1 Jul. 13, 2023

(51) Int. Cl.
| | |
|---|---|
| *A61B 18/00* | (2006.01) |
| *A61B 1/00* | (2006.01) |
| *A61B 17/068* | (2006.01) |
| *A61B 18/14* | (2006.01) |
| *A61B 90/00* | (2016.01) |

(52) U.S. Cl.
CPC ...... *A61B 18/1445* (2013.01); *A61B 1/00009* (2013.01); *A61B 17/0682* (2013.01); *A61B 90/39* (2016.02); *A61B 2018/1452* (2013.01); *A61B 2090/3908* (2016.02); *A61B 2090/3991* (2016.02)

(58) Field of Classification Search
CPC ............ A61B 1/00009; A61B 17/0682; A61B 18/1445; A61B 90/39
See application file for complete search history.

(56) References Cited

U.S. PATENT DOCUMENTS

| | | | | |
|---|---|---|---|---|
| 6,808,491 | B2 * | 10/2004 | Kortenbach | A61B 10/06 600/153 |
| 8,863,748 | B2 * | 10/2014 | Kuroda | A61B 17/0401 600/106 |
| 11,998,187 | B2 * | 6/2024 | Karasawa | A61B 17/0469 |
| 2004/0138682 | A1 * | 7/2004 | Onuki | A61B 17/0643 606/205 |
| 2023/0218336 | A1 * | 7/2023 | Higuchi | A61B 90/39 606/46 |

FOREIGN PATENT DOCUMENTS

JP 2010-036024 A 2/2010

* cited by examiner

*Primary Examiner* — Eyamindae C Jallow
(74) *Attorney, Agent, or Firm* — Oliff PLC

(57) ABSTRACT

A lesion resection method includes a marking step of forming a three-dimensional marking in peripheral tissues of a lesion; a grasping step of grasping the lesion by a grasping forceps; a retracing step of pulling the marking to a hand side of a staple ejection position of a stapler by pulling the grasping forceps grasping the lesion; a ligating step of ejecting a staple from the stapler to ligate the peripheral tissues of the lesion; and a resecting step of resecting the lesion.

14 Claims, 42 Drawing Sheets

LESION RESECTION METHOD

TECHNICAL FIELD

The present disclosure relates to a lesion resection method.

BACKGROUND

Recently, in a surgery of ligating the gastrointestinal duct or the like, a resection method of using a ligation device such as a stapler or the like is used. It is possible to make the surgery of ligating the gastrointestinal duct or the like to be easy and significantly reduce the surgery time by using a suitable ligating device.

In Japanese Unexamined Patent Application, First Publication No. 2010-036024, a ligation device used by being attached to an endoscope is disclosed. A surgeon uses the endoscope with the ligation device being attached thereto to perform the procedures of full thickness resection on the portion including the lesion site of the gastrointestinal duct or the like.

Generally, in the full thickness resection using a medical stapler, as a preprocessing of the resection, there is a case of cauterize the peripheral tissues of the lesion site and perform the marking by a high-frequency treatment device so as to determine a guide of a region for the resection. After the marking, the ligation with respect to the peripheral tissues of the lesion site is performed by the medical stapler in a state in which the lesion site is grasped and pulled to the hand side and the tissues outside the ligation position are cut off. Here, in order to more correctly resect the lesion site, it is necessary to dispose the ligation position by the stapler to be outside of the marking position. In other words, at the time of the ligation by the medical stapler, it is necessary to make the marking position to be pulled to the hand side than the stapler ejection position. However, in a case of a planar marking that is formed by cauterizing the peripheral tissues by the high-frequency treatment device, there is a case in which it is difficult to recognize whether the marking position is at the hand side of the ejection position of the stapler during the ligation.

SUMMARY

According to a first aspect of the present disclosure, a lesion resection method including a marking step of forming a three-dimensional marking in peripheral tissues of a lesion site, a retracting step of pulling the marking to be at a hand side of a staple ejection position of a stapler by pulling the grasping forceps grasping the lesion site, a ligating step of ejecting a staple from the stapler to ligate the peripheral tissues of the lesion site, and a resecting step of cut off tissues to resect the lesion site.

DETAILED DESCRIPTION

First Embodiment

A first embodiment of the present disclosure will be described by referring to FIG. 1 to FIG. 22. In the following figures, a dimensional scale may be different due to the configuration element so as to make each configuration element to be easily viewed.

Figure 1:
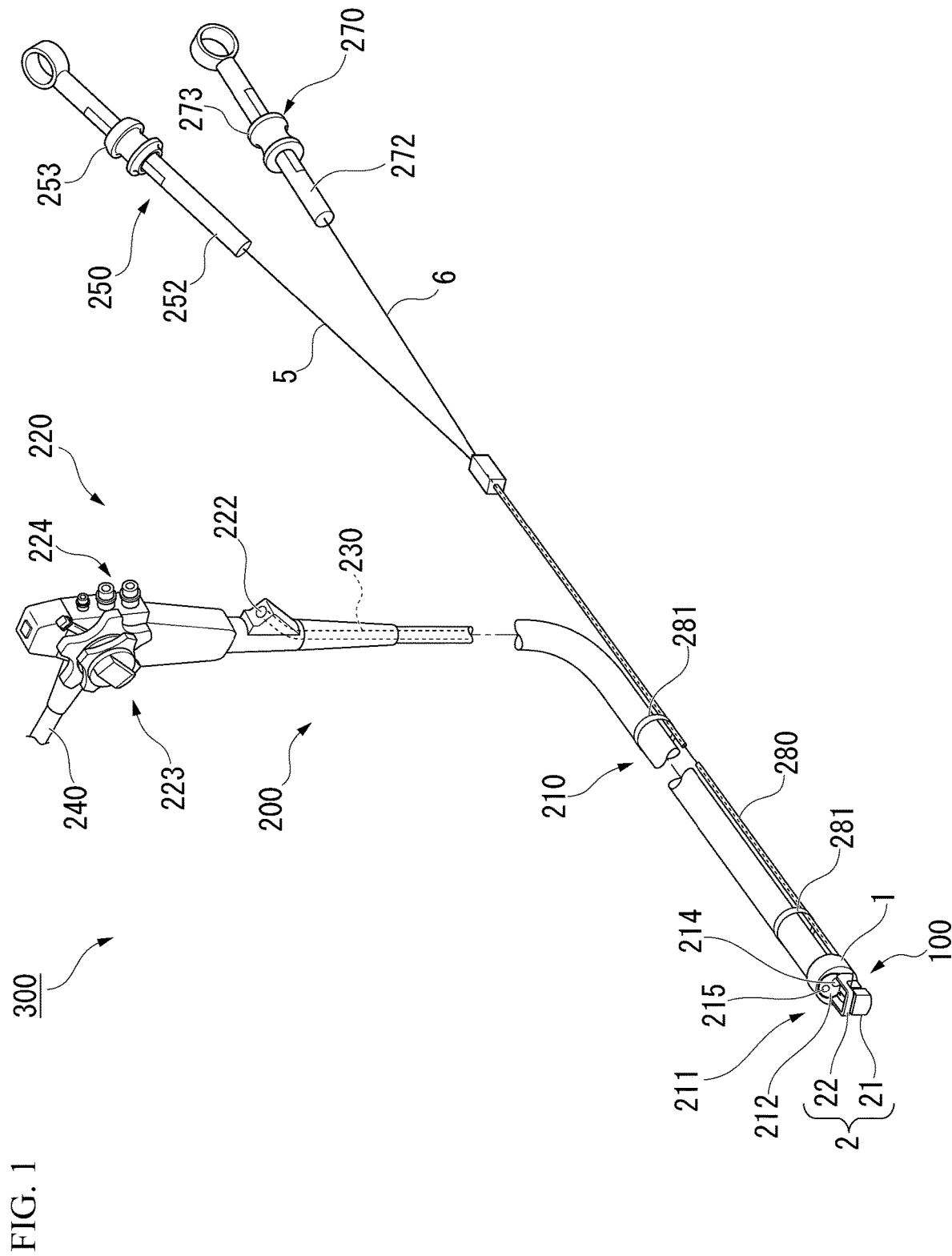
FIG. 1 is a view showing a medical system using a resection method according to a first embodiment of the present invention.

FIG. 1 is a view showing an overall configuration of a medical system 300 used in a lesion resection method according to the present embodiment. The medical system used in the lesion resection method according to the present embodiment is not limited to the medical system 300.

[Medical System 300]

The medical system 300 shown in FIG. 1 is used in a surgery for ligating the gastrointestinal duct or the like. The medical system 300 includes a medial stapler 100, an endoscope 200, an open-close operation portion 250, an extraction operation portion 270, and a wire sheath 280. The open-close operation portion 250 is an operation portion for operating the medical stapler 100 by an open-close operation wire 5. The extraction portion 270 is an operation for operating the medical stapler 100 by an extraction operation wire 6.

[Endoscope 200]

The endoscope 200 is a conventional flexible endoscope including an elongated insertion portion 210 that is inserted into the body from a distal end, an operation portion 200 provided at a proximal end portion of the insertion portion 210, and a universal cord 240.

A treatment device channel 230 for inserting an endoscopic treatment device therethrough is formed in the insertion portion 210. A forceps port 214 as a distal opening of the treatment device channel 230 is provided at a distal end 212 of the insertion portion 210. The treatment device channel 230 extends from the distal end 212 of the insertion portion 210 to the operation portion 220.

A distal end portion 211 of the insertion portion 210 includes an imaging unit (not shown) having a CCD or the like. An object lens 215 of the imaging unit is exposed to the distal end 212 of the insertion portion 210.

A knob 223 for operating the operation portion 210 and a switch 224 for operating the imaging unit are provided at the proximal end side of the operation portion 220. The surgeon operates the knob 223 so as to direct the insertion portion 210 to be bent to a desired direction.

A forceps insertion port 222 communicating with the treatment device channel 230 is provided at the distal end side of the operation portion 220. The surgeon inserts the endoscopic treatment device from the forceps insertion port 222 into the treatment device channel 230.

The universal cord 240 is configured to connect the operation portion 220 with the external peripheral device. The universal cord 240 is configured to output the image captured by the imaging unit to the external device. The image captured by the imaging unit is displayed on a display apparatus such as an LCD display via an image processing apparatus.

[Open-Close Operation Portion 250]

The open-close operation portion 250 is an operation portion for opening and closing the medical stapler 100 by operating the open-close operation wire 5. As shown in FIG. 1, the open-close operation portion 250 includes an open-close operation portion main body 252 and open-close operation slider 253. A proximal end of the open-close operation wire 5 is connected to the open-close operation slider 253. The surgeon may advance and retract the open-close operation wire 5 by advancing and retracting the open-close operation slider 253 in a longitudinal direction with respect to the open-close operation portion main body 252.

[Extraction Operation Portion 270]

The extraction operation portion 270 is an operation portion for extracting (ejecting) a stapler S (see FIG. 10) from the medical stapler 100 by operating the extraction operation wire 6. As shown in FIG. 1, the extraction operation portion 270 includes an extraction operation portion main body 272 and an extraction operation slider 273. A proximal end of the extraction operation wire 6 is connected to the extraction operation slider 273. The surgeon may advance and retract the extraction operation wire 6 by advancing and retracting the extraction operation slider 273 with respect to the extraction operation portion main body 272 in the longitudinal direction.

[Wire Sheath 280]

The wire sheath 280 is a sheath for the open-close operation wire 5 and the extraction operation wire 6 to be inserted through. As shown in FIG. 1, the distal end side of the wire sheath 280 is connected to the insertion portion 210 of the endoscope 200 by a plurality of bands 281.

[Medical Stapler 100]

Figure 2:
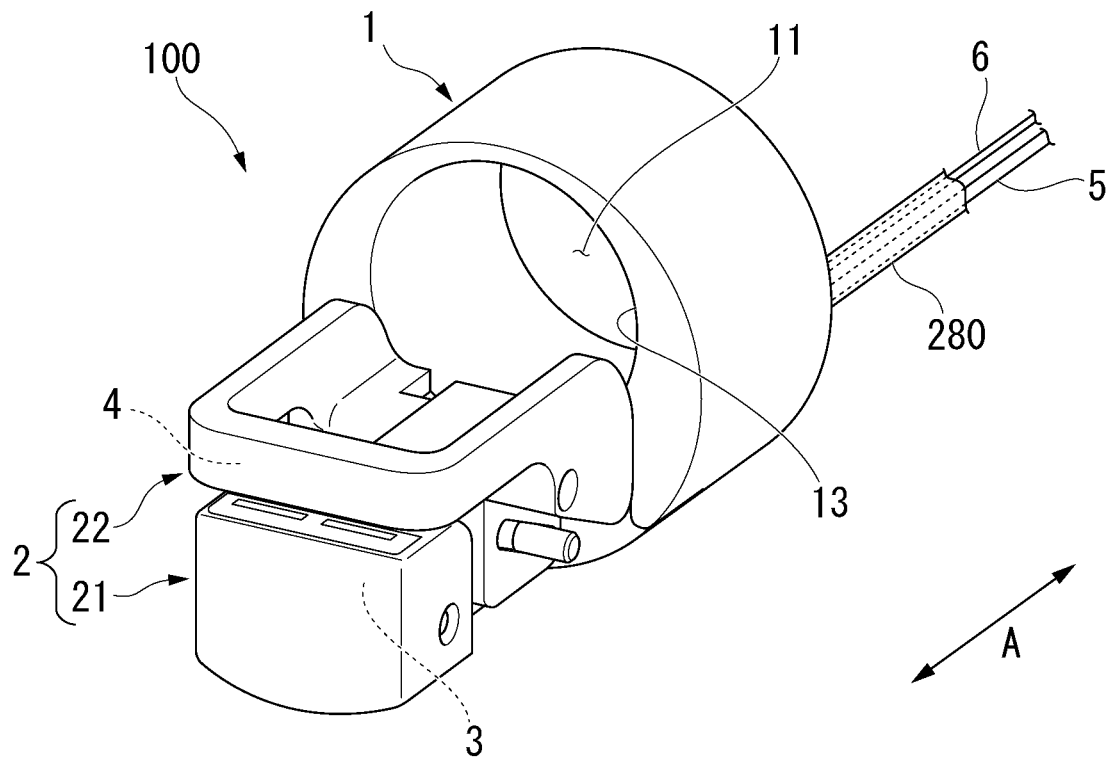
FIG. 2 is a perspective view of a medical stapler.

FIG. 2 is a perspective view showing the medical stapler 100.

The medical stapler (ligation device) 100 includes a cap 1, a grasping portion 2, a staple extraction portion 3, a staple reception portion 4, an open-close operation wire 5, and an extraction operation wire (power transmission member) 6. The medical stapler 100 is attachable to and detachable from the distal end portion 211 of the insertion portion 210 shown in FIG. 1.

Figure 3:
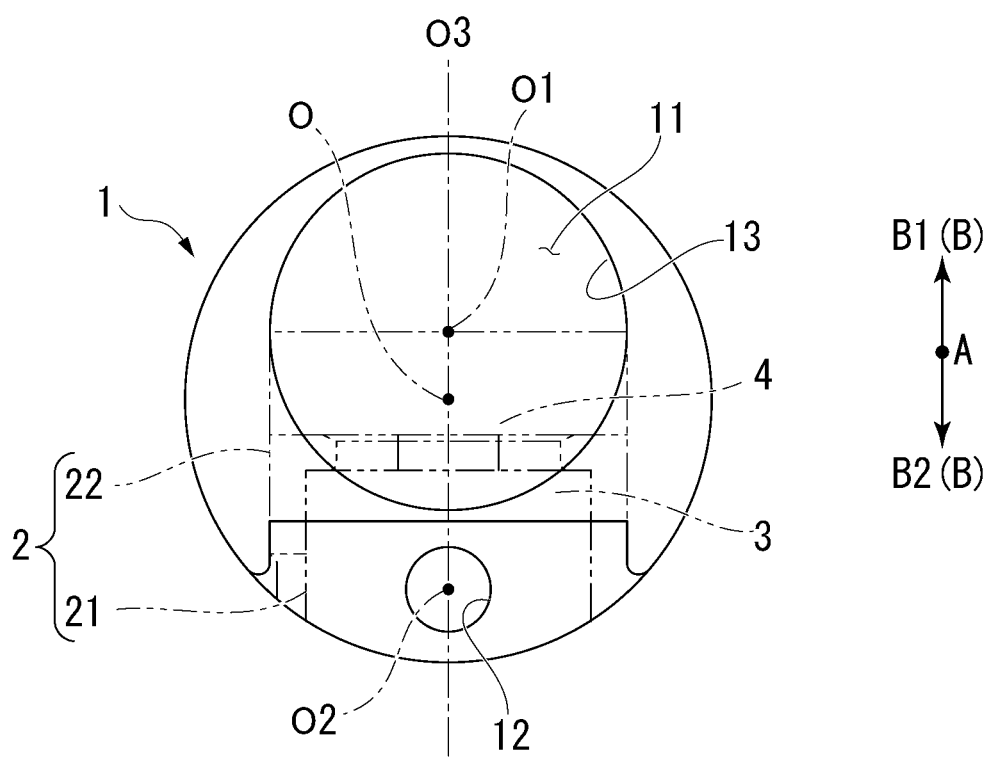
FIG. 3 is a front view of a cap of the medical stapler.

FIG. 3 is a front view of the cap 1. In FIG. 3, the grasping portion 2 is transparently displayed.

The cap (detachable portion) 1 is a member attachable to and detachable from the distal end portion 211 of the endoscope 200 shown in FIG. 1. The cap 1 is formed in a substantial cylindrical shape and has a first penetration hole 11 penetrating in an axial direction A and a second penetration hole 12 penetrating in the axial direction A.

The first penetration hole 11 is a hole to which the distal end portion 211 as the insertion portion 210 of the endoscope 200 shown in FIG. 1 is inserted. A shape of the first penetration hole 11 is formed following an external form of the distal end portion 211 of the insertion portion 210. Accordingly, as shown in FIG. 1, it is possible to attach the cap 1 to the distal end portion 211 of the endoscope 200 by inserting the distal end portion 211 of the endoscope 200 into the first penetration hole 11.

As shown in FIG. 3, a central axis O1 of the first penetration hole 11 in the axial direction A is offset with respect to a central axis O of the cap 1 in the axial direction A. A direction in which the central axis O1 is offset from the central axis O is referred to as an "upper side B1".

The second penetration hole 12 is a hole in which the wire sheath 280 is inserted, wherein the open-close operation wire 5 and the extraction operation wire 6 are inserted through the wire sheath 280. An inner diameter of the second penetration hole 12 is substantially the same with an outer diameter of the wire sheath 280. A distal end portion of the wire sheath 280 is inserted through the second penetration hole 12 and fixed. The open-close operation wire 5 and the extraction wire 6 pass through the second penetration hole 12 and extend to the distal end side.

As shown in FIG. 3, a central axis O2 of the second penetration hole 12 in the axial direction A is offset with respect to the central axis O of the cap 1 in the axial direction A. A direction in which the central axis O2 is offset from the central axis O is opposite to the direction (upper side B1) in which the central axis O1 is offset from the central axis O. The direction in which the central axis O2 is offset from the central axis O is referred to as a "lower side B2". In the present embodiment, the upper side B1 and the lower side B2 are directions along a up-down direction B.

Figure 4:
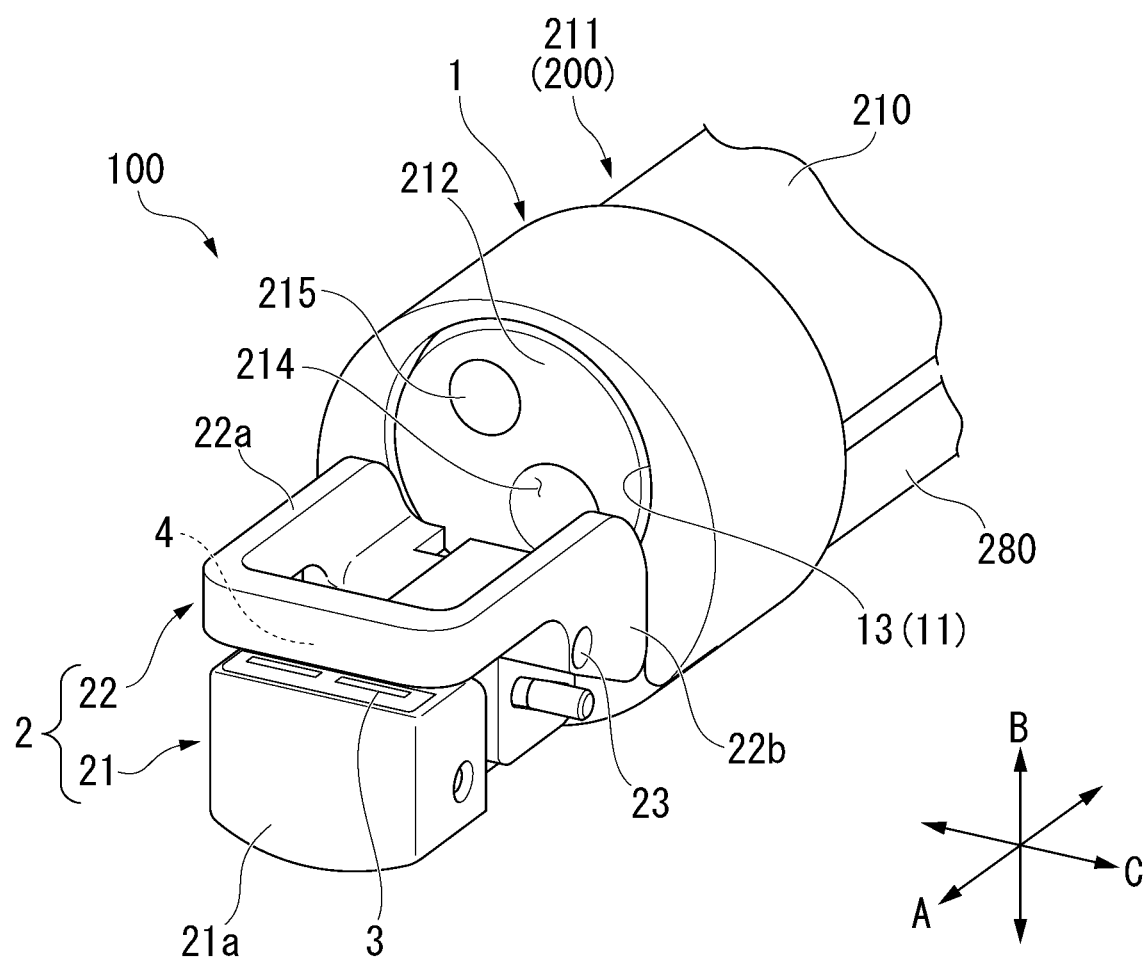
FIG. 4 is a perspective view of the medical stapler with a grasping portion in a closed state.
Figure 5:
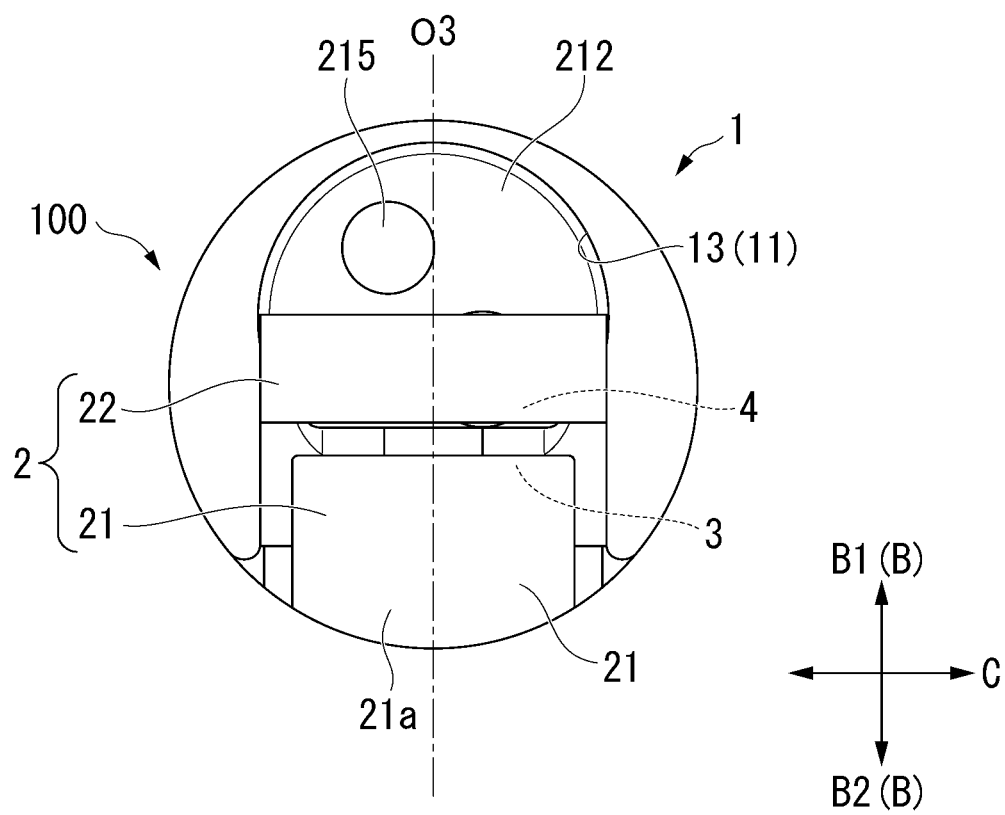
FIG. 5 is a front view of the medical stapler with the grasping portion in the closed state.

As shown in FIG. 4 and FIG. 5 are perspective view and front view of the medical stapler 100 when the grasping portion 2 is in a closed state.

When the cap 1 is attached to the distal end portion 211 of the endoscope 200, as shown in FIG. 4 and FIG. 5, the object lens 215 and the forceps port 214 are exposed from the opening at the distal end side of the first penetration hole 11 of the cap 1. The surgeon may observe the treatment target by the object lens 215 even in the state in which the medical stapler 100 is attached to the distal end portion 211 of the endoscope 200.

Figure 6:
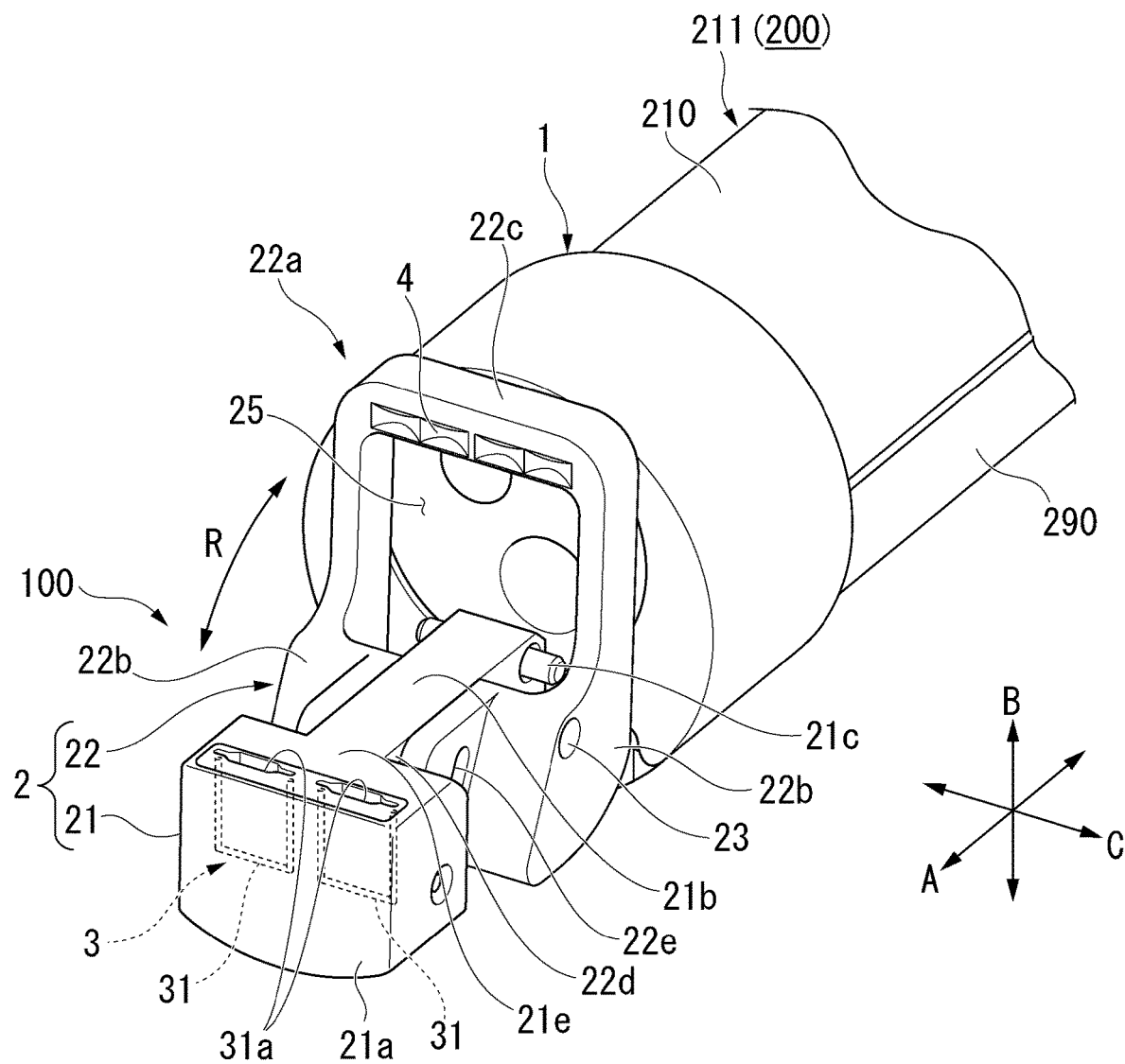
FIG. 6 is a perspective view of the medical stapler with the grasping portion in an open state.
Figure 7:
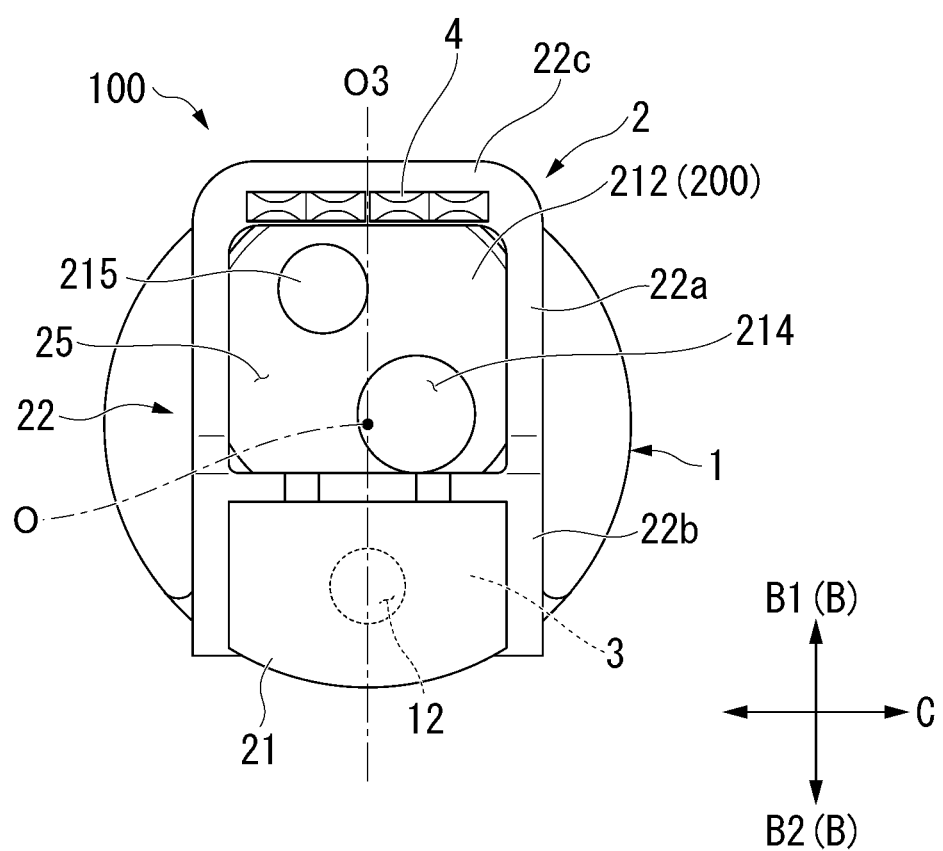
FIG. 7 is a front view of the medical stapler with the grasping portion in the open state.
Figure 8:
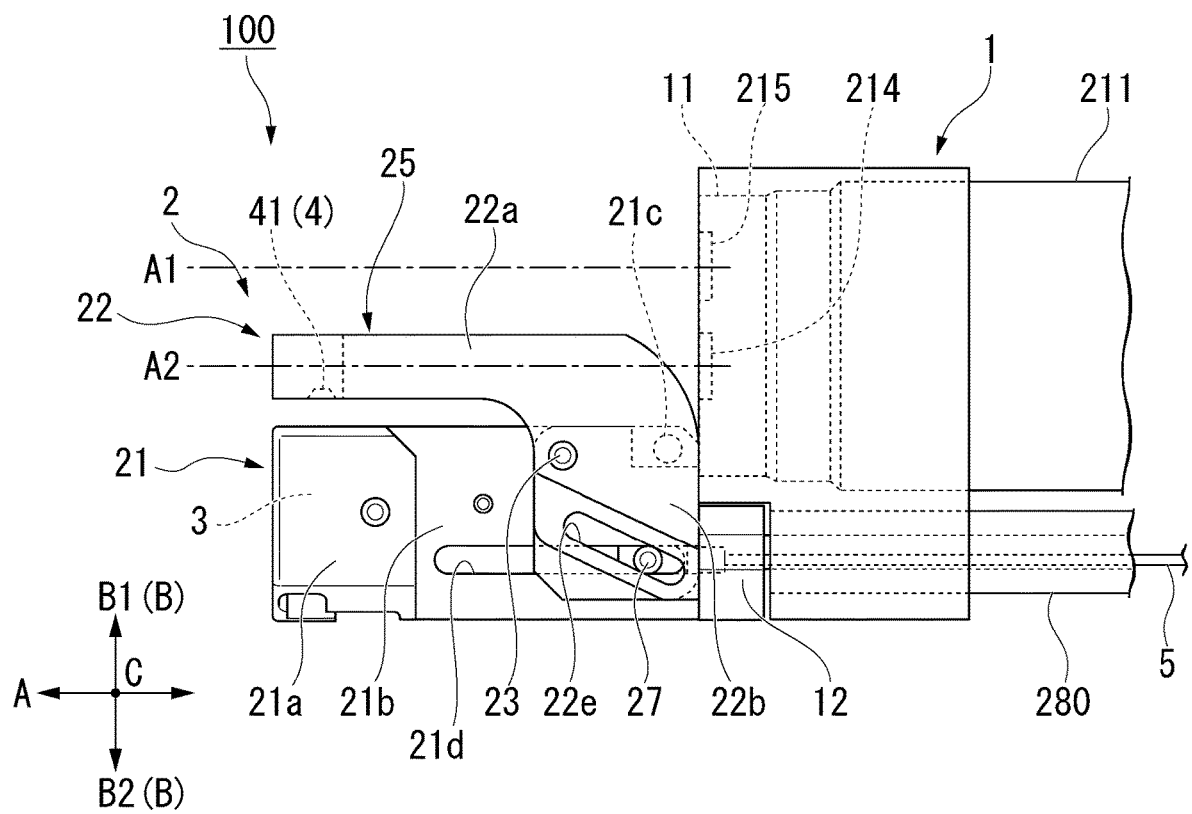
FIG. 8 is a side view of the medical stapler with the grasping portion in the closed state.
Figure 9:
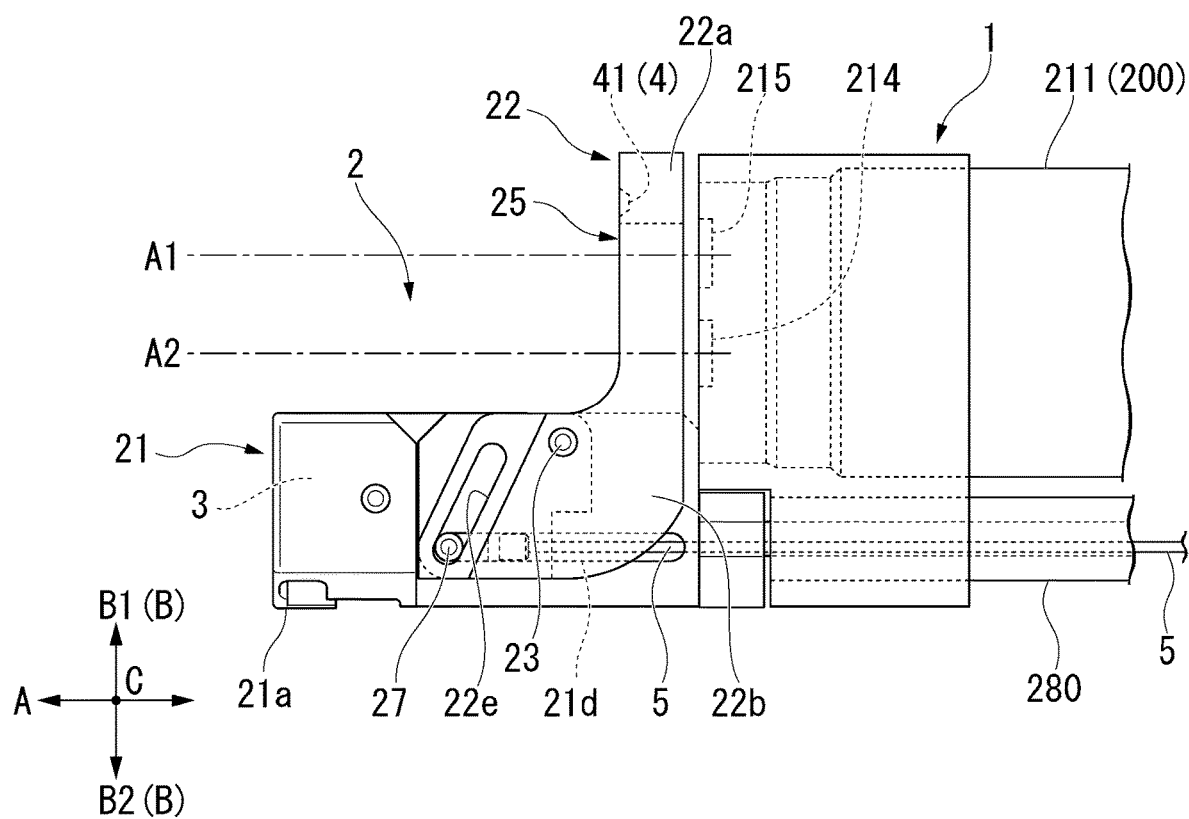
FIG. 9 is a side view of the medical stapler with the grasping portion in the open state.

FIG. 6 and FIG. 7 are perspective view and front view of the medical stapler 100 when the grasping portion 2 is in an open state. Furthermore, FIG. 8 is a side view of the medical stapler 100 when the grasping portion 2 is in the closed state. FIG. 9 is a side view of the medical stapler 100 when the grasping portion 2 is in the open state.

As shown in FIG. 8, the grasping portion 2 includes a first grasping member 21, a second grasping member 22, an open-close rotation axis 23, and a movable pin 27. The first grasping member 21 and the second grasping member 22 are connected to each other to be openable and closable by the open-close rotation axis 23. The open-close rotation axis 23 is disposed at the distal end side of the cap 1. The axial direction C of the open-close rotation axis 23 is orthogonal to the axial direction A and the up-down direction B of the cap 1. The grasping portion 2, as shown in FIG. 7, is formed to be symmetric with a central axis O3 in the up-down direction B.

The first grasping member 21 is fixed to the distal end side of the cap 1 to be unrotatable. The first grasping member 21 is fixed to the cap 1 at the lower side B1 with respect to the central axis O of the cap 1. The first grasping member 21, as shown in FIG. 7, is disposed at a position overlapping the second penetration hole 12 of the cap 1 in the front view. On the other hand, the first grasping member 21, as shown in FIG. 7, is disposed at the position not to overlap the object lens 215 and the forceps port 214 of the endoscope 200 in the front view.

As shown in FIG. 6, the first grasping member 21 includes a first distal end portion 21a and a first main body portion 21b, and the first grasping member 21 is formed in a substantial T shape in a planar view viewed from the up-down direction B. The first distal end portion 21a is disposed at the distal end side of the first main body portion 21b.

The first distal end portion 21a is formed in a substantial cuboid shape. The first distal end portion 21a is formed in a rectangle shape extending in the axial direction C of the open-close rotation axis in the planar view. The staple extraction portion 3 is provided in the first distal end portion 21a. An opening 31a of the staple extraction portion 3 is provided on a surface (upper surface 21e) at the upper side B1 of the first distal end portion 21a.

The first main body portion 21b is an elongated member extending in the axial direction A. A distal end of the first main body portion 21b is fixed to the first distal end portion 21a. A proximal end of the first main body portion 21b is fixed to the cap 1 via the wire sheath 280. The first main body portion 21b includes a contact pin 21c and a first engaging groove 21d (see FIG. 8).

The contact pin 21c is provided at the proximal end of the first main body portion 21b and configured to come into contact with the second grasping member 22 in the closed state so as to regulate a moveable range of the second grasping member 22.

The first engaging groove 21d as shown in FIG. 8 is a groove penetrating in the axial direction C of the open-close rotation axis 23 in the first main body portion 21b. The first engaging groove 21d extends in the axial direction A of the grasping portion 2.

The second grasping member 22 is attached to the first grasping member 21 by the open-close axis 23 so as to be rotatable. The second grasping member 22 includes a U-shaped member 22a formed in a substantial U shape and a second main body portion 22b configured to support the U-shaped member 22a to be rotatable.

The U-shaped member 22a is formed in a substantial U shaped as shown in FIG. 6 and FIG. 7, and two end portions thereof are connected to the second main body portion 22b while an intermediate portion is disposed at the distal end side. As shown in FIG. 6 and FIG. 7, the intermediate portion includes a second distal end portion 22c. The second distal end portion 22c is formed in a substantial cuboid shape. The staple reception portion 4 is provided in the second distal end portion 22c.

As shown in FIG. 8 and FIG. 9, the second main body portion 22b is attached to the first main body portion 21b of the first grasping member 21 by the open-close rotation axis 23 to be rotatable. A guide groove 22d into which the first main body portion 21b is inserted is formed in the second main body portion 22b. Second engaging grooves 22e are formed at two end portions of the guide groove 22d of the second main body portion 22b.

The second engaging groove 22e is a groove formed in the second main body portion 22b. The second engaging groove 22e is a groove penetrating in the axial direction C. As shown in FIG. 8 and FIG. 9, the second engaging groove 22e is formed at the opposite side with respect to the staple reception portion 4 by sandwiching the open-close rotation axis 23 therebetween. The second engaging groove 22e is symmetric with respect to the central axis O3 of the second grasping member 22 (see FIG. 7).

As shown in FIG. 6, the second grasping member 22 include a visual field space 25 penetrating in the open-close direction R between the staple reception portion 4 at the distal end side the open-close axis 23 at the proximal end side. In the present embodiment, the visual field space 25 is a space being surrounded by the sides of the U-shaped member 22a formed in the substantial U shape.

As shown in FIG. 8, the movable pin 27 is engaged with the first engaging groove 21d and the second engaging groove 22e to advance and retract in the axial direction A along the first engaging groove 21d. The distal end of the open-close operation wire 5 is attached to the movable pin 27. As shown in FIG. 9, when the open-close operation wire 5 is advanced to the distal end side, the movable pin 27 makes the second grasping member 22 to rotate around the open-close rotation axis 23 as the rotation center such that the grasping portion 2 enters the open state. As shown in FIG. 8, when the open-close operation wire 5 is retracted to the hand side of the endoscope 200, the movable pin 27 makes the second grasping member 22 to rotate around the open-close rotation axis 23 such that the grasping portion 2 enters the closed state.

As shown in FIG. 5, when the grasping portion 2 is in the closed state, the staple extraction portion 3 and the staple reception portion 4 are opposite to each other in the up-down direction B. When the grasping portion is in the open state, there is a slight gap formed between the staple extraction portion 3 and the staple reception portion 4.

As shown in FIG. 8, when the grasping portion 2 is in the closed state, an optical axis A1 of the object lens 215 passes through the upper side B1 of the first grasping member 21 and the second grasping member 22. When the grasping member 2 is in the closed state, in the front view, the central axis A2 of the forceps port 214 does not overlap the first grasping member 21; however, the central axis A2 of the forceps port 214 is at the position overlapping the second grasping member 22.

When the grasping portion 2 is in the closed state, as shown in FIG. 9, the staple reception portion 4 is disposed at the hand side of the endoscope 200 with respect to the open-close rotation axis 23. When the grasping portion 2 is in the open state, the staple extraction portion 3 and the staple reception portion 4 are disposed at the upper side B1 and the lower side B2 respectively to sandwich the optical axis A1 of the object lens 215. When the grasping portion 2 is in the open state, the optical axis A1 of the object lens 215 passes through the visual field space 25. When the grasping portion 2 is in the open state, the central axis A2 of the forceps port 214 passes through the visual field space 25.

Figure 10:
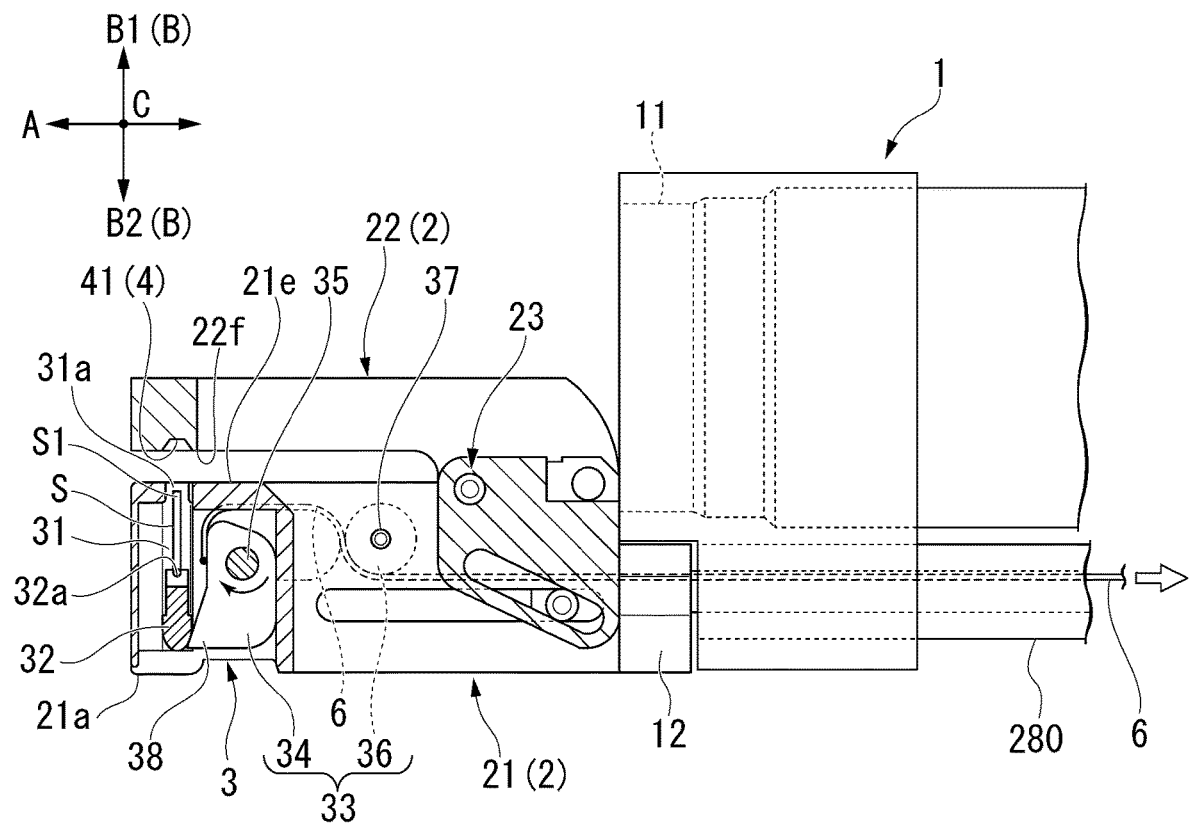
FIG. 10 is a cross-sectional view of the grasping portion including a staple extraction portion.

FIG. 10 is a cross-sectional view of the grasping portion 2 including the staple extraction portion 3.

The staple extraction portion 3 is provided at the first distal end portion 21a of the first grasping member 21 so as to be able to accommodate and extract the staple S. The staple extraction portion 3 includes a staple accommodation portion 31, a move-straight member 32, and a rotation member 33.

The staple accommodation portion 31 is a space for accommodating the staple S provided at the first distal end portion 21a of the first grasping member 21. In the first grasping member 21, two staple accommodation portions 31 as shown in FIG. 6 are formed to be arranged along the axial direction C to be able to accommodate two U-shaped staples S.

The staple accommodation portion 31 opens in the up-down direction B at the opening 31a provided on the upper surface 21e of the first distal end portion 21a. The staple S is accommodated in the staple accommodation portion 31 from the opening 31a. The staple S is accommodated in the staple accommodation portion 31 in a state in which a needle tip S1 of the staple S faces the upper side B1.

In the planar view, the staple accommodation portion 31 is formed in a rectangle shape with a short side extending in the axial direction A and a long side extending in the axial direction C. The staple S accommodated in the staple accommodation portion 31 have the needle tips S1 of two ends arrayed in the axial direction C.

The move-straight member 32 is a member accommodated in the staple accommodation portion 31 and is movable in the up-down direction B in the inner space of the staple accommodation portion 31. The move-straight member 32 has a concave portion 32a supporting the staple S at the upper side B1. The staple S accommodated in the staple accommodation portion 31 is fitted into the concave portion 32a.

A first pulley 34 and a second pulley 36 as the rotation member 33 are attached to the inside of the first grasping member 31 to be rotatable and the first pulley 34 and the second pulley 36 rotate so as to make the move-straight member 32 to move in the up-down direction B. The distal end of the extraction operation wire 6 is connected with the first pulley 34. It is possible to rotate the first pulley 34 by pulling the extraction operation wire 6.

The second pulley 35 is attached to the inside of the first grasping member 21 to be rotatable, and the first pulley 34 is disposed to at the distal end side of the second pulley 36. A rotation axis 35 of the first pulley 34 and a rotation axis 37 of the second pulley 36 extend in the axial direction C and are substantial parallel to the open-close rotation axis 23 of the grasping portion 2. The first pulley 34 has a convex portion (contact portion) 38 provided at the distal end side for supporting the move-straight member 32 from the lower side B2.

The distal end of the extraction operation wire 6 is connected to the first pulley at the upper side B1 with respect to the rotation axis 35. The extraction operation wire 6 passes through the second penetration hole 12 from the first pulley 34 via the second pulley 36 and then extends to the extraction operation portion 270 (see FIG. 1).

Figure 11:
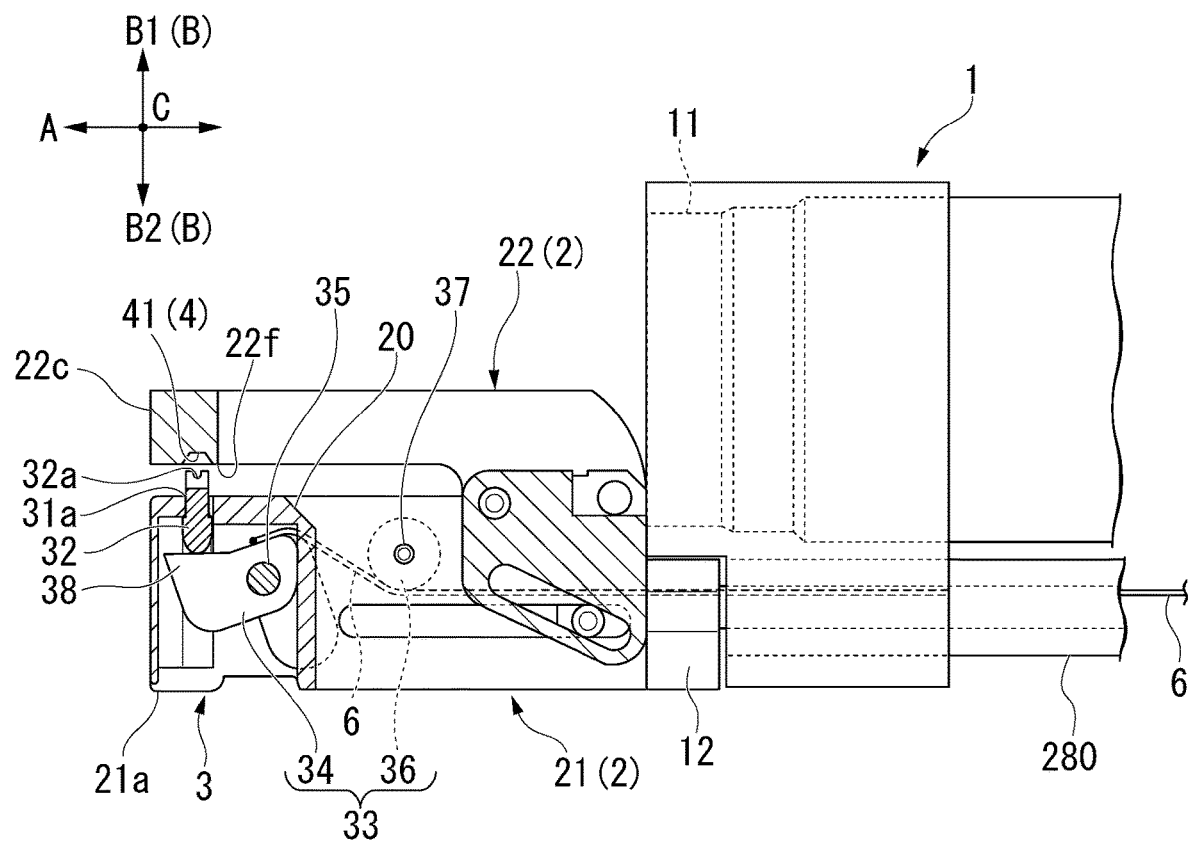
FIG. 11 is a cross-sectional view of the grasping portion where an extraction operation wire is pulled.

FIG. 11 is a cross-sectional view of the grasping portion 2 in which the extraction operation wire 6 is pulled.

The first pulley 34 rotates by pulling the extraction operation wire 6 and the convex portion 38 of the first pulley 34 pushes up the move-straight member 32 such that the accommodated staple S is extracted to the upper side B1 from the opening 31a.

The staple reception portion (anvil) 4 is provided on the lower surface 22f of the second distal end portion 22c of the second grasping member 22. A plurality of pockets 41 capable of receiving the staple S extracted from the staple extraction portion 3 are provided in the staple reception portion 4. In the present embodiment, two of U-shaped staples are extracted from the staple extraction portion 3 such that as shown in FIG. 6 and FIG. 7, four pockets are provided in the staple reception portion 4. As shown in FIG. 10, when the grasping portion 2 is in the closed state, the opening 31a from which the staple S is extracted and the pockets 41 of the staple reception portion 4 are opposite to each other.

[Usage Method of Medical Stapler 100]

Next, an usage method of the medical stapler 100 (an lesion resection method using the medical stapler 100) will be described. FIG. 12 to FIG. 19 are views for describing the usage method of the medical stapler 100.

Figure 12:
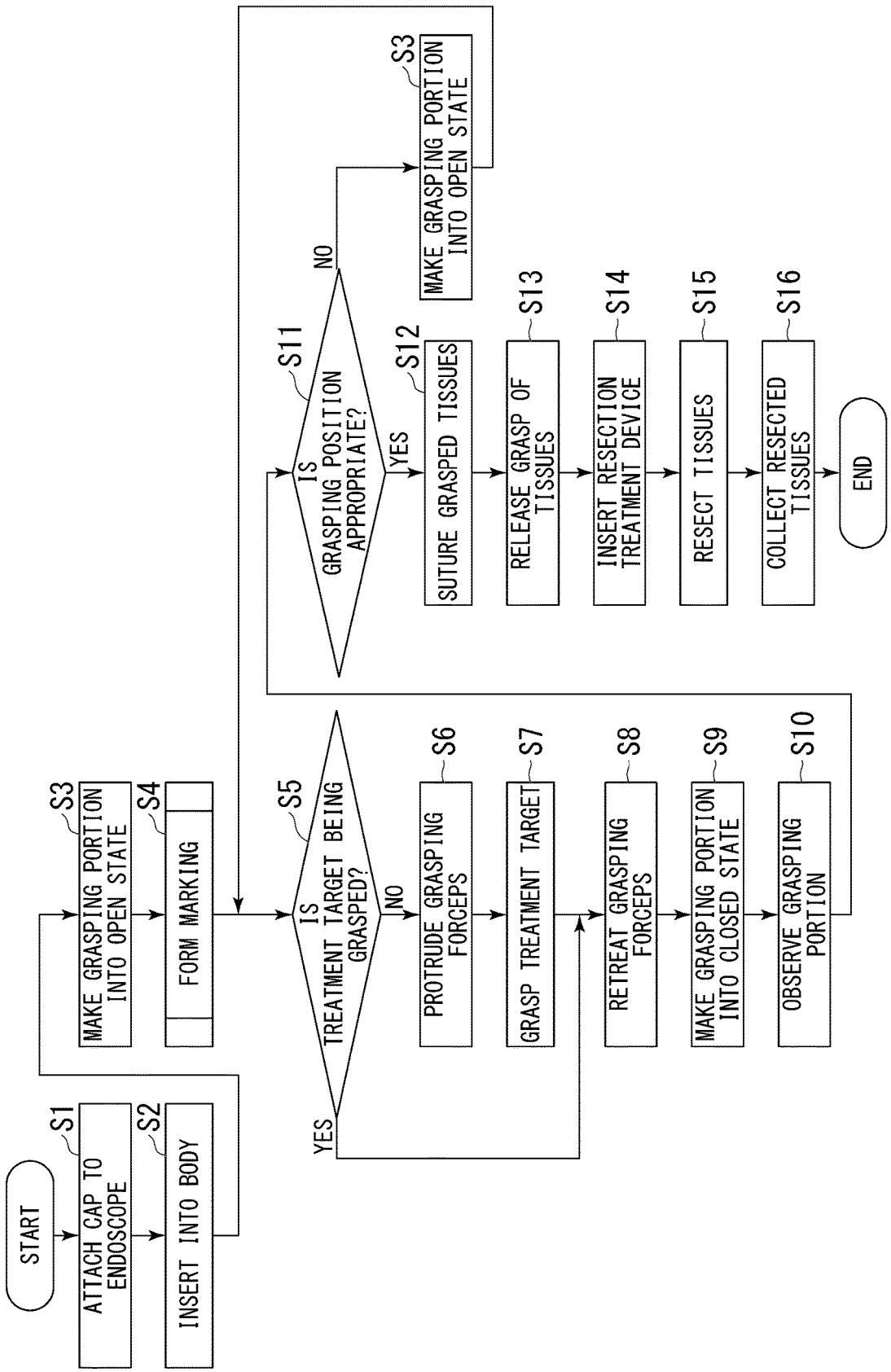
FIG. 12 is a flowchart showing a lesion resection method using the medical stapler.
Figure 13:
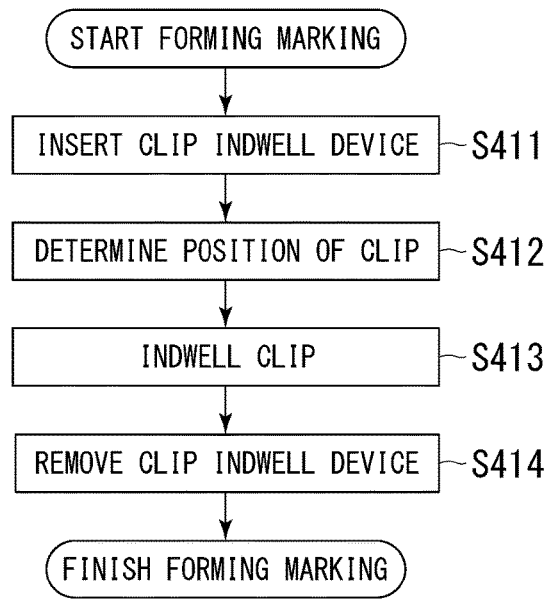
FIG. 13 is a flowchart showing a marking step.

FIG. 12 is a flowchart showing the lesion resection method using the medical stapler. FIG. 13 is a flowchart showing a marking step.

The lesion resection method according to the present embodiment will be described based on the flowchart of FIG. 12 showing the whole lesion resection method and the flow chart of FIG. 13 showing the three-dimensional marking formation method.

<Inserting Step>

The surgeon or an assistance (hereinafter, simply referred to as the "surgeon") uses the cap 1 included in the medical stapler 100 to attach the medical stapler 100 to the insertion portion 210 of the endoscope 200 (Step S1). At the time of the attachment of the medical stapler 100, the grasping portion 2 of the medical stapler 100 is in the closed state.

The surgeon inserts the insertion portion 210 of the endoscope 200 to which the medical stapler 100 is attached from the mouth as the natural orifice of the subject (Step S2), and makes the distal end portion 211 to approach the tumor (lesion tissues) TU (see FIG. 14) as the treatment target T.

Next, the surgeon operates the open-close operation portion 250 (see FIG. 1) to advance the open-close operation wire 5 to make the grasping portion 2 into the open state (Step S3).

Even the grasping portion 2 is in the open state, as shown in FIG. 9, the optical axis A1 of the object lens 215 passes through the visual field space 25 such that the surgeon may observe the tumor TU (the treatment target T) through the imaging unit of the endoscope 200.

<Marking Step>

Figure 14:
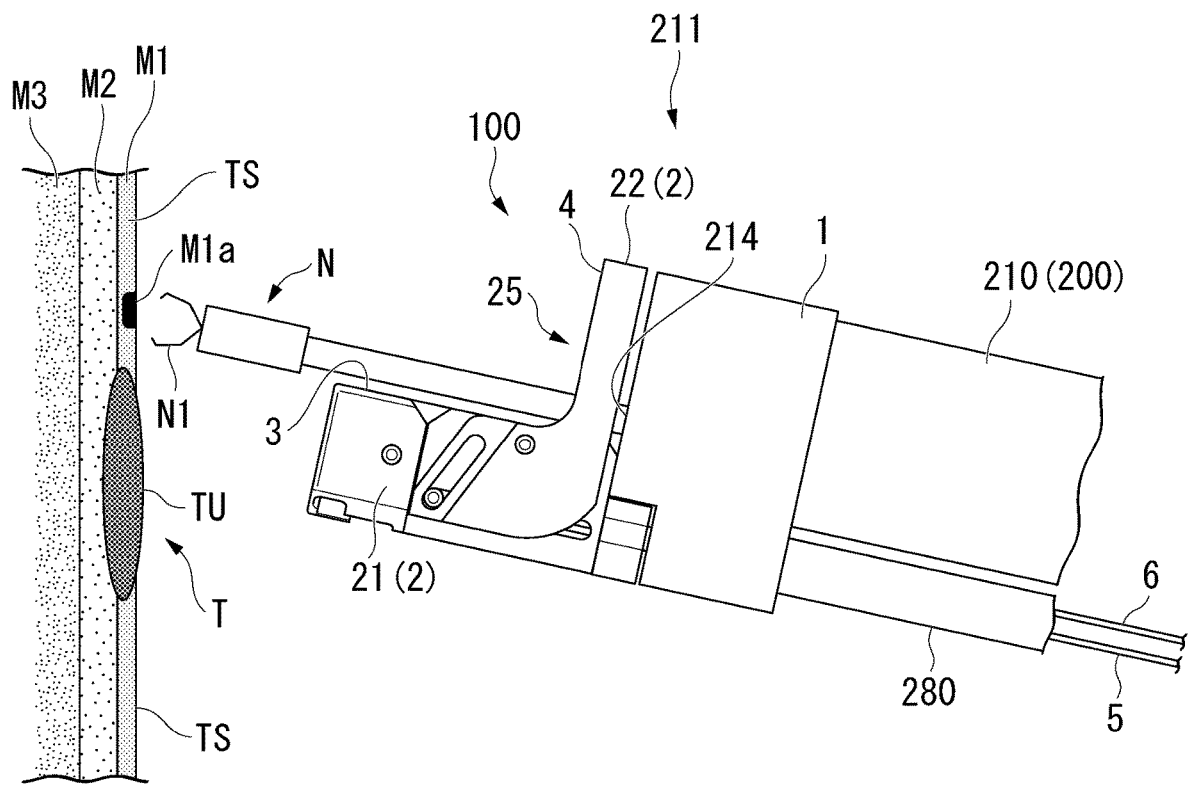
FIG. 14 is a view showing the marking step in the resection method.
Figure 15:
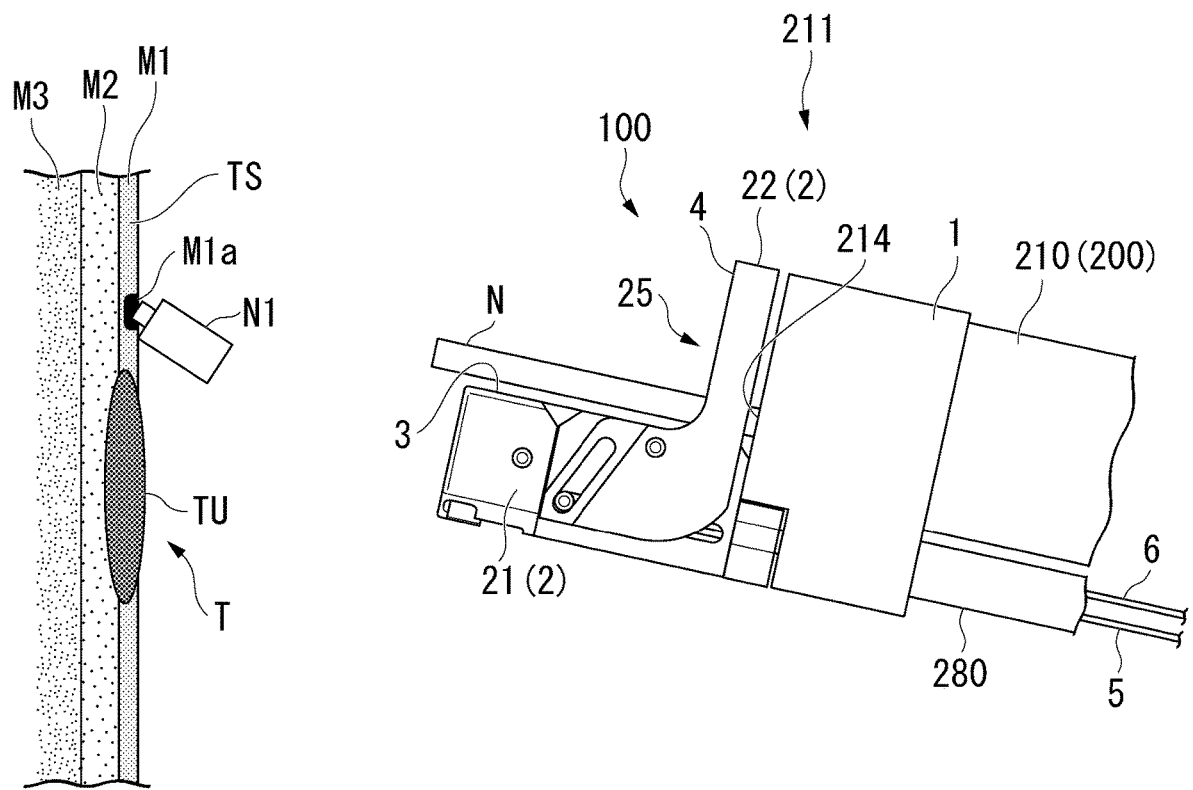
FIG. 15 is a view showing the marking step in the resection method.

Next, the surgeon forms a three-dimensional marking in the peripheral tissues TS of the tumor TU as the treatment target T (Step S4). The marking step of forming the three-dimensional marking is described using FIG. 13. FIG. 14 and FIG. 15 are views showing the marking step in the lesion resection method.

As shown in FIG. 13 and FIG. 14, the surgeon inserts a clip indwelling device N into the treatment channel 230 (see FIG. 1) and protrudes the clip N1 provided at the distal end of the clip indwelling device N from the forceps port 214 (Step S411). The central axis A2 of the forceps port 214 passes through the visual field 25 such that the clip N1 of the clip indwelling device N passes through the grasping portion 2 to approach the tumor TU positioned at the distal end side.

The surgeon bends the endoscope 200 to tilt the clip N1 to an arbitrary direction to determine the position of the clip N1 (Step S412).

Here, the example in which the distal end of the clip N1 is indwelled in a direction separating from the tumor TU will be described. In other words, it is the example in which the proximal end of the clip N1 is indwelled in the direction approaching the tumor Tu.

Next, as shown in FIG. 15, the surgeon operates the clip indwelling device N while pressing the clip N1 to a first part Mia positioned in the mucosal layer of the peripheral tissues TS so as to separate the clip N1 from the distal end of the clip indwelling device N and indwell the clip N1 at the first part Mia (Step S413).

Here, the first part Mia of the peripheral tissues TS is the part positioned at the upper side of the tumor TU when viewed from the retraction direction (visual field of the endoscope) of the grasping forceps G when the grasping forceps G is retracted into the medical stapler 100 during the following retracting step (Step S8).

Next, the surgeon removes the clip indwelling device N from the treatment device channel 230 (see FIG. 1) (Step S414).

The marking step is performed as described above.

<Grasping Step>

Figure 16:
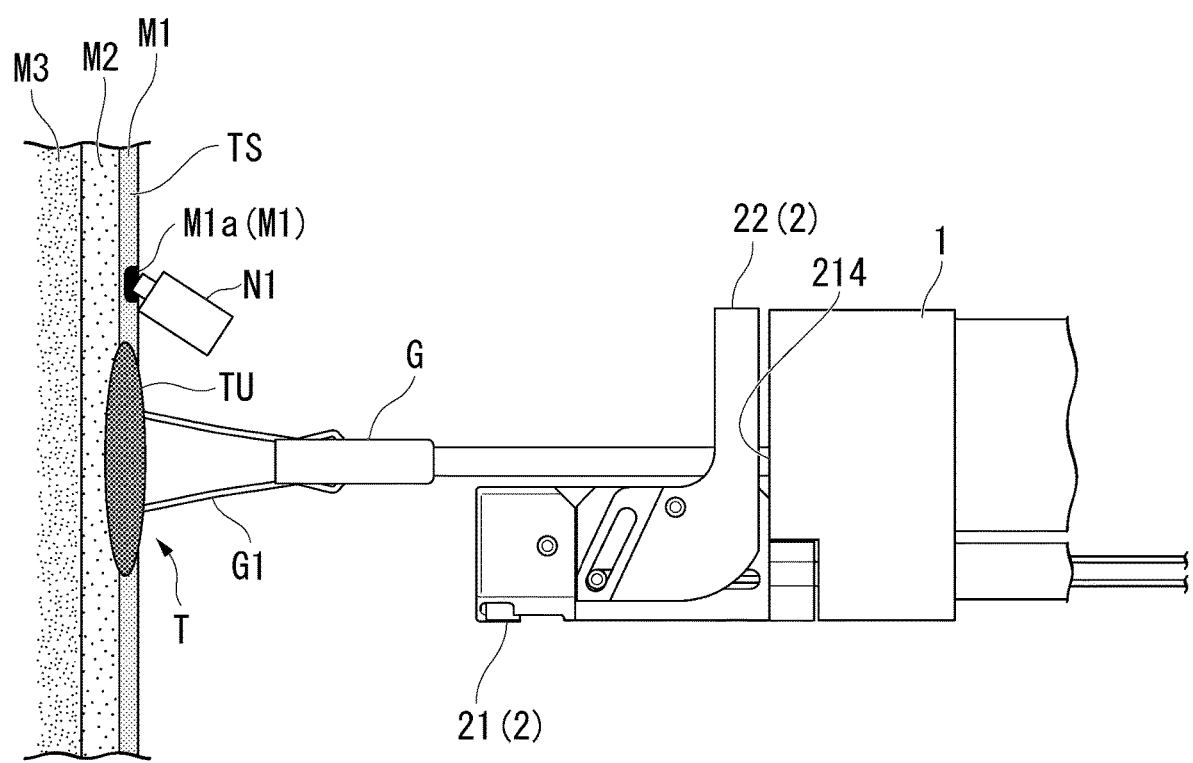
FIG. 16 is a view showing a grasping step in the resection method.

FIG. 16 is a view showing the grasping step in the lesion resection method.

When the surgeon firstly insert the medical stapler 100 into the body, it is in the state in which the tumor TU is not grasped by the grasping forceps G (Grasping confirmation Step S5: No as shown in FIG. 12) such that the next step is executed.

After removing the clip indwelling device N, as shown in FIG. 16, the surgeon inserts the grasping forceps G into the treatment channel 230 to protrude the forceps portion G1 provided at the distal end of the grasping forceps G from the forceps port 214 (Step S6).

The surgeon presses the forceps portion G1 to contact the tumor TU while closing the forceps portion G1 to grasp the tumor TU (Step S7).

<Retracting Step>

Figure 17:
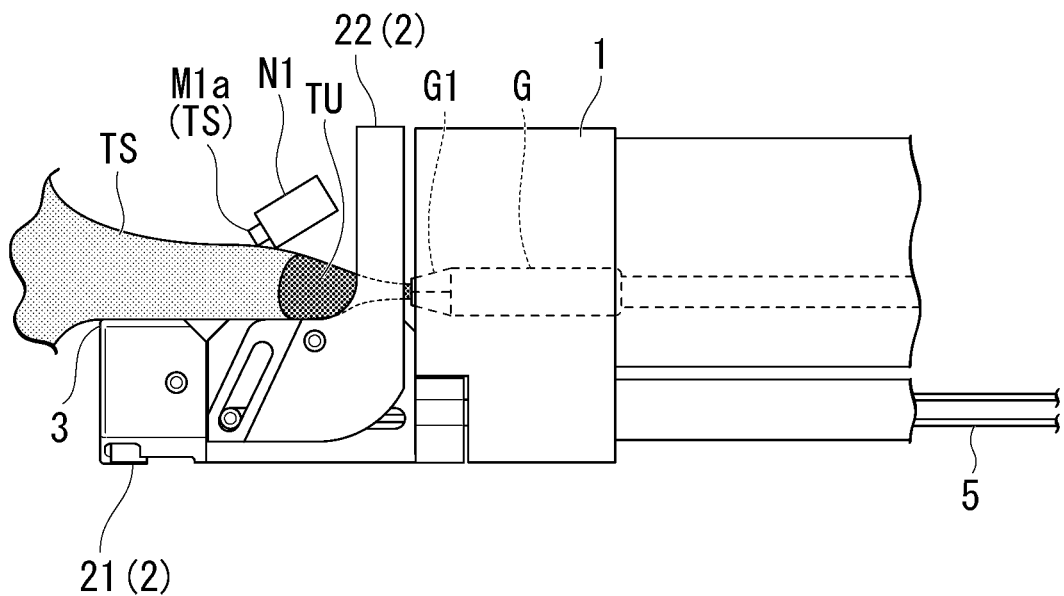
FIG. 17 is a view showing a retracting step in the resection method.
Figure 18:
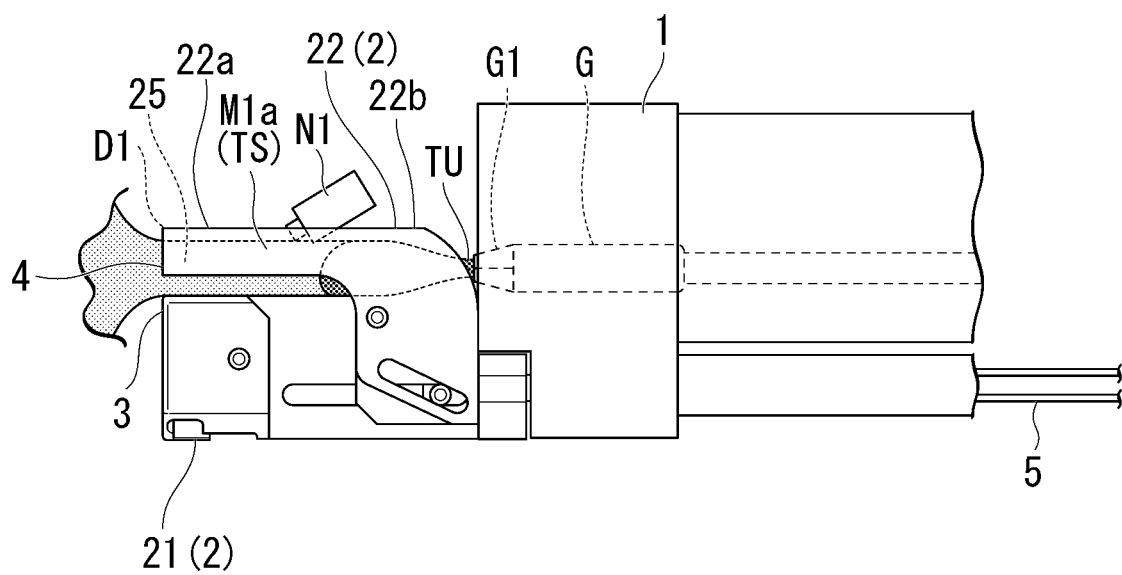
FIG. 18 is view showing the retracting step in the resection method.
Figure 19:
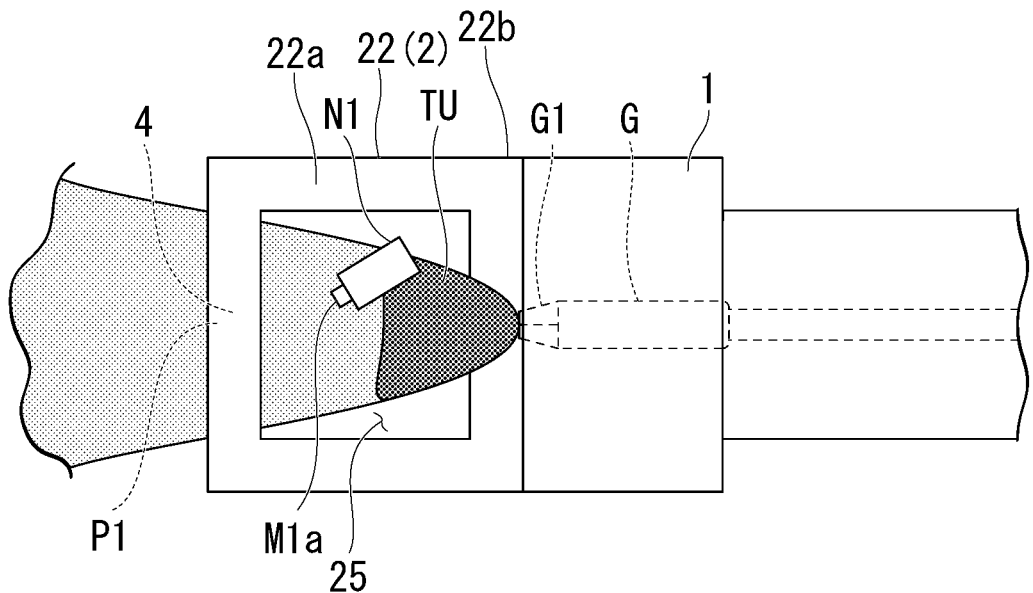
FIG. 19 is a view showing a top view of the retracting step in the resection method.

FIG. 17 is a view showing a retracting step in the lesion resection method. FIG. 18 is a side view showing the retracting step in the lesion resection method. FIG. 19 is a top view showing the retracting step in the lesion resection method.

As shown in FIG. 17, the surgeon pulls and draws the grasping forceps G with the tumor TU grasped by the forceps portion G1 toward the hand side (proximal end side of the endoscope, the proximal end side of the grasping forceps, and the proximal end side of the medical stapler). The surgeon pulls the grasping forceps G to the hand side of the endoscope 200 in the state in which the tumor TU is grasped by the forceps portion G1 and makes the grasping forceps G to retract (Step S8). As shown in FIG. 17, the surgeon retracts the grasping forceps G such that the distal end of the grasping forceps G is disposed at the hand side of the endoscope 200 with respect to the staple extraction portion 3. It is preferable that the grasping forceps G is retracted such that the clip N1 is disposed at the hand side of the endoscope 200 with respect to the staple extraction portion 3.

After the surgeon operates the open-close operation portion 250 (see FIG. 1) to retract the open-close operation wire 5, as shown in FIG. 18, the grasping portion 2 is in the closed state (Step S9). The surgeon makes a ligation position P1 (see FIG. 19) where is at the outside of the tumor TU with respect to the first part M1a of the peripheral tissues TS to be clamped by the staple extraction portion 3 of the first grasping member 21 and the staple reception 4 of the second grasping member 22.

At this time, the surgeon clamps the ligation position P1 in the state in which the clip N1 is disposed at the hand side of the endoscope 200 with respect to the staple extraction portion 3. Accordingly, the tumor TU positioned at the inside of the first part Mia of the peripheral tissues TS is disposed at the hand side of the endoscope 200 with respect to the staple extraction portion 3 and the staple reception portion 4.

When the grasping portion 2 is in the closed state, the tumor TU and the clip N that are disposed at the hand side of the endoscope 200 with respect to the staple extraction portion 3 and the staple reception portion 4 are accommodated in the space formed by the U-shaped member 22a and the second main body portion 22b of the second grasping member 22 (the visual field space 25 shown in FIG. 19) such that the grasping operation by the first grasping member 21 and the second grasping member 22 is not obstruct.

The distal end of the clip N1 is directed to the direction separating from the tumor TU (the direction in which the proximal end of the clip N1 approaches the tumor TU) such that the proximal end of the clip N1 is directed to the tumor TU side and it is difficult for the proximal end of the clip N1 to interfere the ligation position P1. Accordingly, the possibility that the clip N1 is clamped at the time when the ligation position P1 is grasped by the first grasping member 21 and the second grasping member 22 is low and it is difficult to obstacle the grasping operation by the grasping portion 2.

<Observing Step>

After the grasping portion 2 is in the closed state, the surgeon observes the positional relationship between the first grasping member 21 and the three-dimensional marking (clip N1) in the visual field of the endoscope (Step S10). As shown in FIG. 9, the optical axis A1 of the object lens 215 passes through the upper side B1 of the first grasping member 21 and the second grasping member 22. Accordingly, the surgeon may also observe the grasped tissues (tumor TU) through the imaging unit of the endoscope 200 when the grasping portion 2 is in the closed state.

Next, according to the observation result, the surgeon determines whether the position grasped by the grasping portion 2 is appropriate or not (Step S11).

If the position grasped by the grasping portion 2 is appropriate (Step S11; Yes), the ligating Step S12 described below will be performed.

On the other hand, in a case in which the position grasped by the grasping portion 2 is inappropriate (Step S11; No), the first grasping member 21 is operated to be in the open state with the tumor TU is maintained to be grasped by the grasping forceps G (Step S3). Due to the state in which the tumor TU is grasped by the grasping forceps G (Grasping confirmation Step S5: Yes), the surgeon determines to transition to the retracting Step S8 at the grasping confirmation Step S5 to adjust the grasping position of the grasping portion 2. As an example of the case in which the grasping position by the grasping portion 2 is inappropriate, a case in which the grasping position by the grasping portion 2 overlaps the clip N1 as the three-dimensional marking, a case in which the clip N1 is significantly separated, and other cases in which the grasping position is not the desired grasping position by the surgeon can be considered.

In the lesion resection method according to the present embodiment, Step S10 and Step S11 may be omitted.

Figure 20:
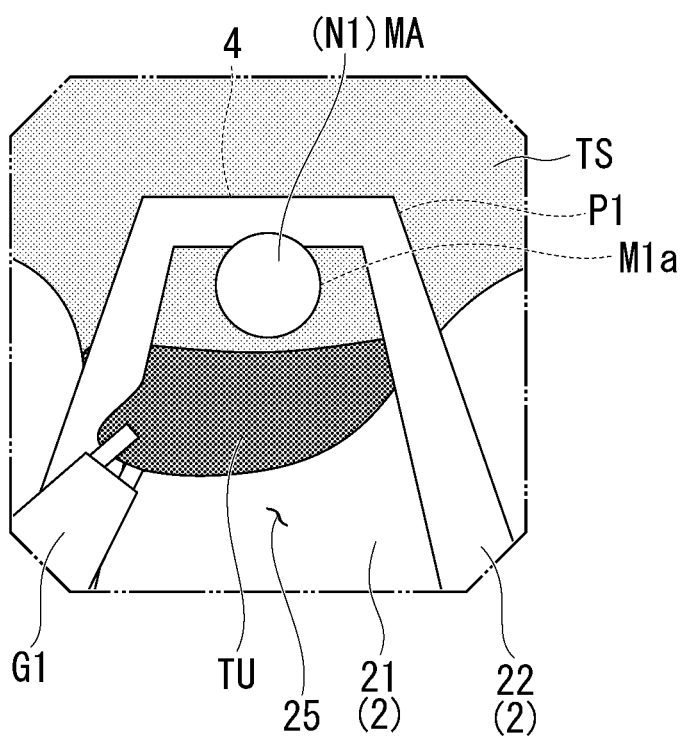
FIG. 20 is a view showing a view field of an endoscope in the retracting step in the resection method.

FIG. 20 is a view showing the visual field of the endoscope in the Retracting step of the lesion resection method.

FIG. 20 is a view showing the visual field of the endoscope when the ligation position P1 is clamped by the staple extraction portion 3 of the first grasping member 21 and the staple reception portion 4 of the second grasping member 22.

Since the clip N1 indwelled at the first part Mia of the peripheral tissues TS is three-dimensional, it is easy to visually confirm the front-rear relationship between the second grasping member 22 and the three-dimensional marking (clip N1) in the visual field of the endoscope.

Accordingly, it is possible to recognize that the ligation position P1 being at the deep side in the visual field (body side) with respect to the three-dimensional marking (clip N1) is grasped, and it is possible to make the full thickness resection to be performed more correctly.

<Ligating Step>

Figure 21:
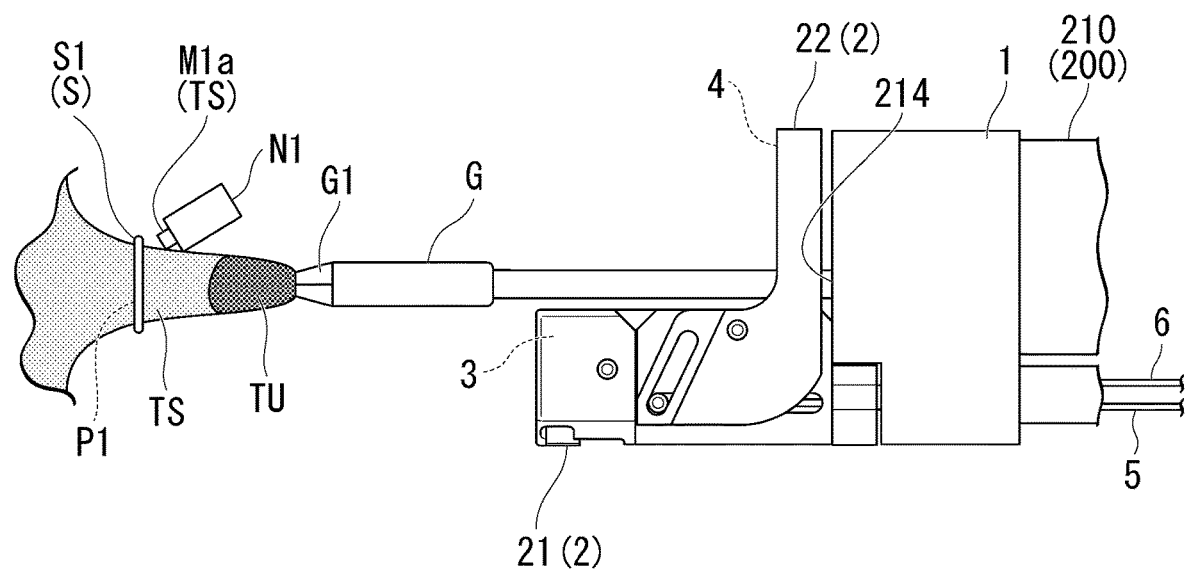
FIG. 21 is a view showing a ligating step in the resection method.

FIG. 21 is a view showing the Ligating step in the lesion resection method.

The surgeon operates the extraction operation portion 270 (see FIG. 1) to pull the extraction operation wire 6 in the state in which the ligation position P1 is clamped by the staple extraction portion 3 and the staple reception portion 4 so as to eject the accommodated staple S from the staple reception 4 to perform the ligation (Step S12). The needle tip S1 of the staple S penetrates the ligation position P1 and comes into contact with the pocket 41 of the staple reception portion 4 to be bent. As a result, the ligation position P1 is ligated.

As shown in FIG. 21, the surgeon operates the open-close operation portion 250 (see FIG. 1) to make the grasping portion 2 into the open state again. The surgeon opens the grasping forceps G to release the grasp of the tumor TU by the grasping forceps G (Step S13).

Here, it is described that the grasping forceps G is separated from the tumor TU after ligating the peripheral tissues TS; however, it is possible to separate the grasping forceps G from the tumor TU at any timing after the grasping portion 2 is in the closed state in the retracting Step S8.

<Resecting Step>

Figure 22:
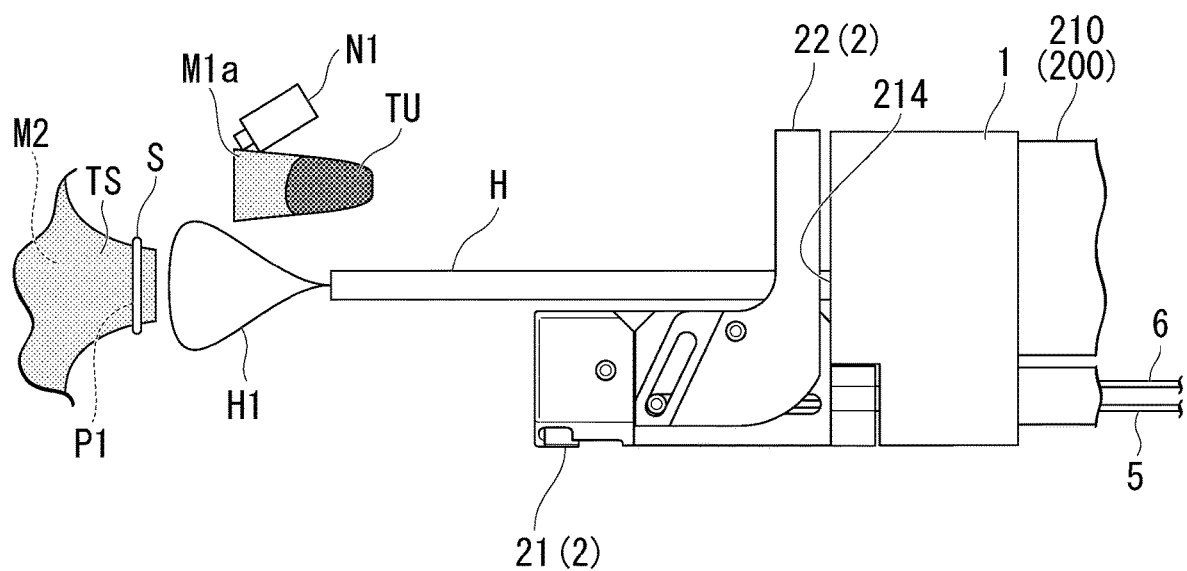
FIG. 22 is a view showing a resecting step in the resection method.

FIG. 22 is a view showing the resecting step in the lesion resection method.

Next, the surgeon removes the grasping forceps G from the treatment channel 230 (see FIG. 1) and inserts a high-frequency snare H as a resection treatment device (Step S14) to protrude a snare wire H1 provided at the distal end of the high-frequency snare H from the forceps port 214. As shown in FIG. 22, the surgeon resects the part including the tumor TU at the hand side (the tumor TU side) of the endoscope 200 with respect to the part ligated by the staple S and at the distal end side (the opposite side of the tumor TU) of the endoscope 200 with respect to the first part Mia of the peripheral tissues TS (Step S15). Specifically, the surgeon resects the specific part of the peripheral tissues TS including the tumor TU and excluding the ligated part. The tumor TU is disposed at the hand side of the endoscope 200 with respect to the ligated part (the ligation position P1) such that the surgeon may definitely resect the whole tumor TU without any part left. Even the tumor TU is large to reach the submucosa layer M2, the surgeon may definitely resect the whole tumor TU without any part left. The surgeon collects the resected tumor TU (Step S16) to finish the lesion resection treatment.

As disclosed above, according to the lesion resection method of the present embodiment, when the peripheral tissues TS is grasped by the first grasping member 21 and the second grasping member 22, it is easy to visually confirm whether the three-dimensional marking (clip N1) is at the hand side (the endoscope side) with respect to the second distal end portion 22c of the second grasping member 22 viewed from the direction of retracting the grasping forceps G (the imaging unit side). Accordingly, it is possible to definitely retract the three-dimensional marking (clip N1) positioned at the outside of the tumor TU into the medical stapler 100 (the visual field space 25) and to ligate the ligation position P1 positioned at the outside of the first part M1a of the peripheral tissues TS. Accordingly, the surgeon may definitely resect the whole tumor TU without any part left.

Figure 23:
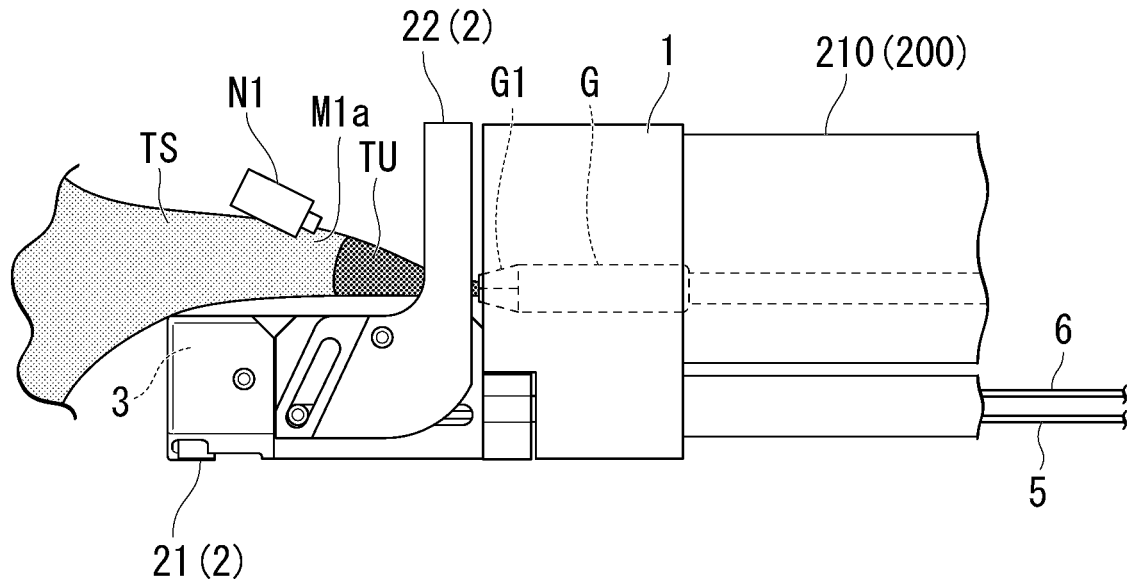
FIG. 23 is a view showing another example of the marking step and the retracting step in the resection method.

In the present embodiment, it is described that in the Marking step S4, the clip N1 is disposed such that the distal end of the clip N1 is directed toward the direction separating from the tumor TU; however, it is not limited to the configuration. For example, in the marking Step S4, as shown in FIG. 23, the clip N1 may be disposed such that the distal end of the clip N1 is directed toward the direction approaching the tumor TU (the direction in which the proximal end of the clip N1 separates from the tumor TU).

In the case in which the clip N1 is indwelled at the first part M1a of the peripheral tissues TS such that the distal end of the clip N1 is directed to the direction separating from the tumor TU, it enters the state in which the distal end of the clip N1 approaches the endoscope 200 and the proximal end of the clip N1 separates from the endoscope at the time of the retraction step (Step S8), such that the merit is achieved that the clip N1 is prevented from being hooked on the inner circumferential edge of the second grasping member (U-shaped member 22a) in the open state.

Figure 24:
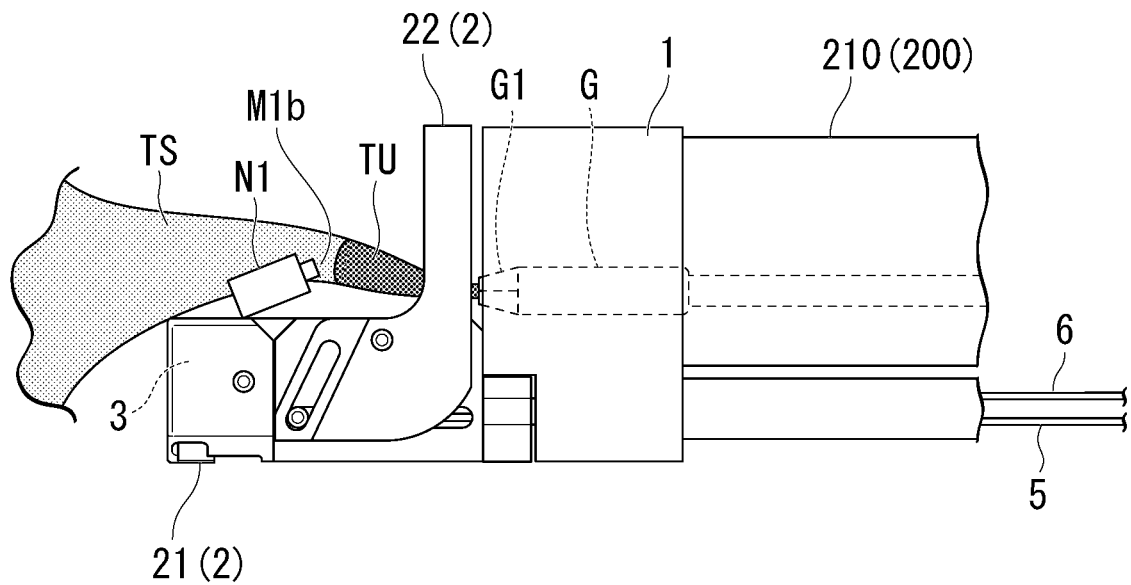
FIG. 24 is a view showing another example of the marking step and the retracting step in the resection method.

In the present embodiment, in the marking step S4, it is described to indwell the clip N1 at the first part M1a of the peripheral tissues TS, however, as shown in FIG. 24, the clip N1 may be indwelled at a second part M1b in the mucosa layer M1 of the peripheral tissues TS.

Here, the second part M1b of the peripheral tissues is the part positioned at the lower side (the first grasping member 21 side) of the tumor TU in the visual field of the endoscope when the grasping forceps G is retracted into the medial stapler 100 during the retraction step (Step S8).

According to the method, when the tumor TU is pulled by the grasping forceps G (Step S8), the second grasping member 22 comes into contact with the clip N1 and it is possible to bring the resistance feeling (click feeling) to the surgeon. Accordingly, it is possible to notify the surgeon that the second part M1b of the peripheral tissues TS is retracted to the hand side of the endoscope 200 with respect to the staple extraction portion 3.

Although the first embodiment of the present disclosure has been described above referring to the figures, the technical scope of the present disclosure is not limited to the above-described embodiment, and various changes or deletion may be made to each component within a range that does not deviate from the gist of the present invention. The configuration elements shown in the above-described embodiment and the modification example may be appropriately combined.

In the above-described embodiment, it is described to indwell one clip N1 with respect to the peripheral tissues TS in the marking step, however, the aspect of the marking step is not limited thereto.

Modification Example 1-1

Figure 25:
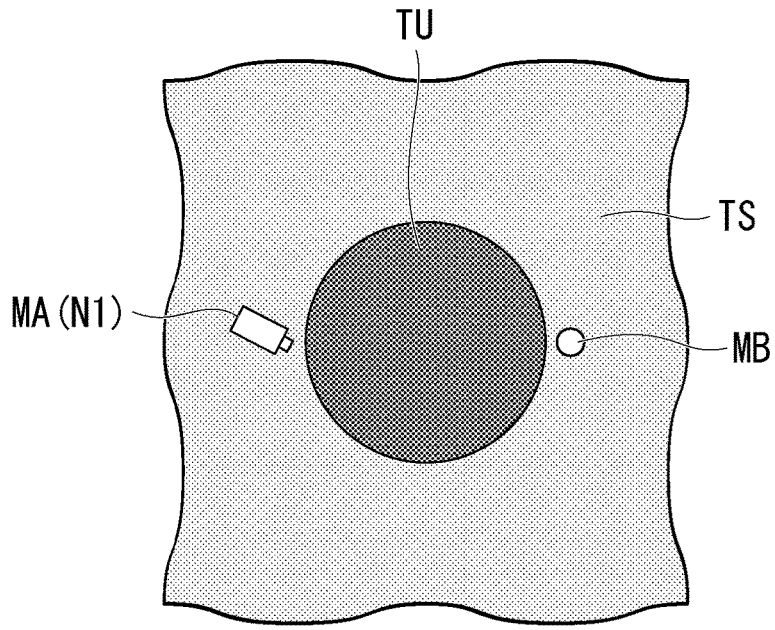
FIG. 25 is a view showing a marking step in a modification example 1-1 of the resection method.
Figure 26:
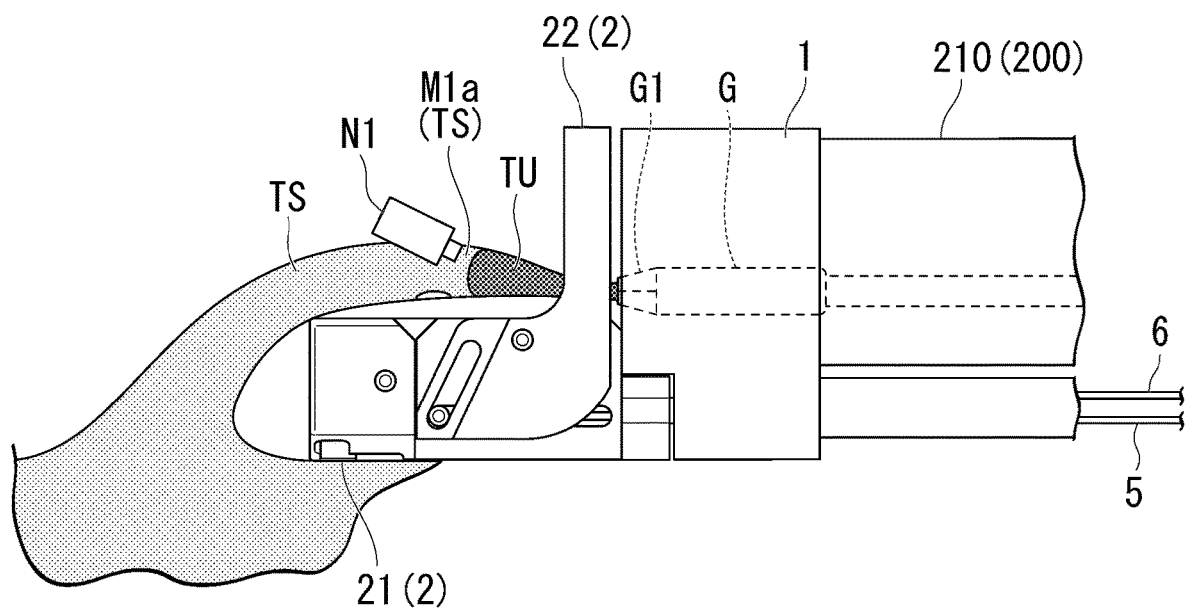
FIG. 26 is a view showing a retracting step in the modification example 1-1 of the resection method.

FIG. 25 is a view showing a marking step in the modification example 1-1 of the resection method. FIG. 26 is a view showing a retracing step in the modification example 1-1 of the resection method.

As shown in FIG. 25, in the marking step S4 of the modification example 1-1 of the first embodiment, a three-dimensional marking MA by the clip N1 and a planar marking MB by the cauterization are formed in the peripheral tissues TS surrounding the tumor TU and there are two markings being made in total.

In the present embodiment, among the peripheral tissues surrounding the circumference of the tumor TU, in the part at the opposite side of the three-dimensional marking by the clip N1, the planar marking MB is made by pressing the high-frequency knife to perform the cauterization. The planar marking Mb is made by cauterizing the mucosa layer M1, and the planar marking MB does not reach the submucosa layer M2 and the muscular layer M3. As shown in FIG. 26, by making the planar marking MB beside the three-dimensional marking by the clip N1, it is easy to recognize the size of the tumor TU and to definitely retract the whole tumor TU into the stapler 100.

Among the peripheral tissue TS surrounding the circumference of the tumor TU, the positions of the three-dimensional marking MA by the clip N1 and the planar marking MB by the cauterization are not limited to the positions shown in FIG. 25 and may be appropriately changed. For example, each of the marking MA and the marking MB may be at the reversed positions with respect to the tumor TU.

Modification Example 1-2

Figure 27:
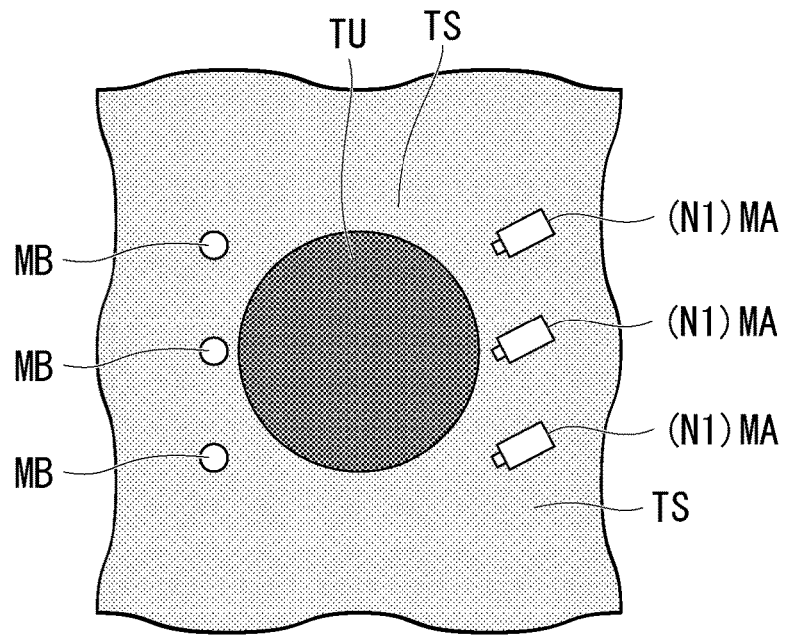
FIG. 27 is a view showing a marking step in a modification example 1-2 of the resection method.
Figure 28:
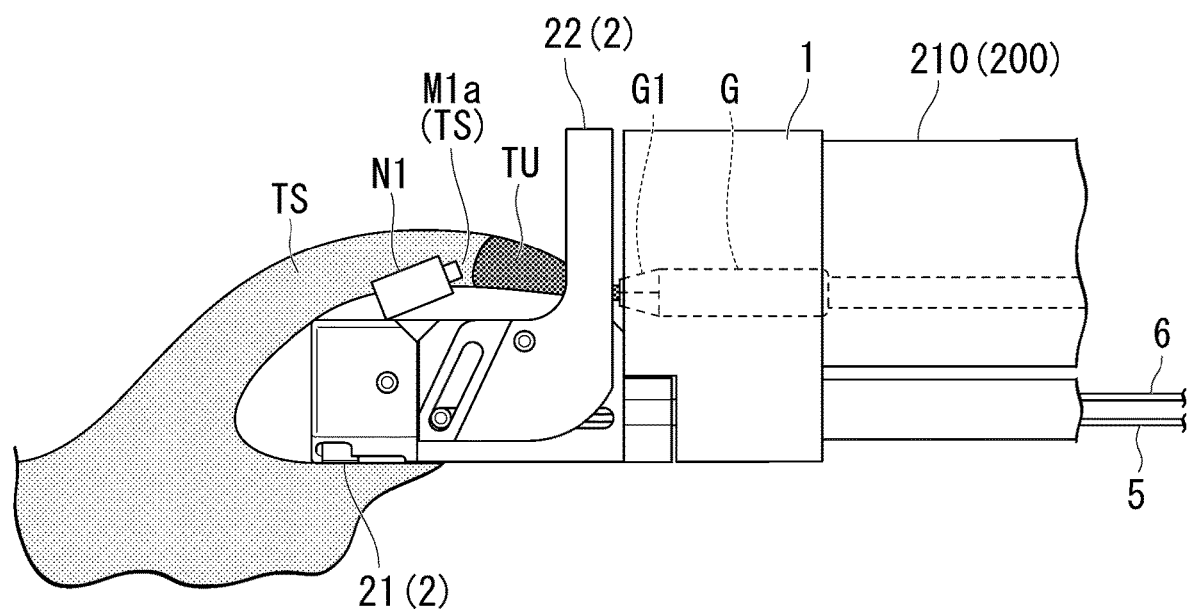
FIG. 28 is a view showing a retracting step in the modification example 1-2 of the resection method.

FIG. 27 is a view showing a marking step in a modification example 1-2 of the resection method. FIG. 28 is a view showing a retracting step in the modification example 1-2 of the resection method.

The marking step in the modification example 1-2 is a method adopted in a case in which the tumor TU is large. As shown in FIG. 27, in the modification example 1-2, a plurality of the three-dimensional markings MA by the clip N1 and a plurality of the planar markings MB by the cauterization are formed respectively.

In the present modification example, among the peripheral tissue TS surrounding the tumor TU, triple of three-dimensional markings MA are formed at one side of the tumor TU while triple of planar markings MB are formed at the other side of the tumor TU. At this time, it is preferable to form the three-dimensional markings MA and the planar markings MB by a predetermined interval in accordance with the size of the tumor TU so as to recognize the range of the tumor TU.

In a case in which the tumor TU is large, it is possible to ligate the whole tumor TU by dividing the ligation into multiple times and to perform the resecting step by multiple times by performing the retracting step and the ligating step repeatedly for multiple times with respect to the tumor TU with the plurality of markings MA and the plurality of markings MB as visual marks. Accordingly, it is possible to resect the whole large tumor TU efficiently without any part left.

In the present modification example, all of the proximal ends of the clips N1 are directed to the direction separating from the tumor TU (the direction in which the distal ends of the clips N1 approach the tumor TU) such that even the three-dimensional marking MA will not be the obstacle at the time of the retraction and the tumor TU together with the clip N1 may be smoothly retracted.

In the present modification example, triple of the three-dimensional markings MA and triple of the planar markings MB are formed; however, the number of the three-dimensional markings MA and the planar markings MB may be appropriately set due to the size of the tumor TU. Also, it is not limited that the number of the three-dimensional markings MA and the number of the planar markings MB is the same. Furthermore, the positions where the three-dimensional markings MA and the planar marking MB are not limited to the position as shown in figures.

Furthermore, each proximal end of the plurality of clips N1 may be directed to the tumor TU side. Accordingly, at the time of retracting the tumor TU, it is possible to regulate the volume of the normal tissues in the circumference of the tumor TU that is retracted together with each clip N1 to a minimum volume. Accordingly, it is possible to reduce the resection volume of the healthy tissues.

Modification Example 1-3

In a marking step S4 according to a modification example 1-3 of the first embodiment, two three-dimensional markings are formed by the clip N1.

Figure 29:
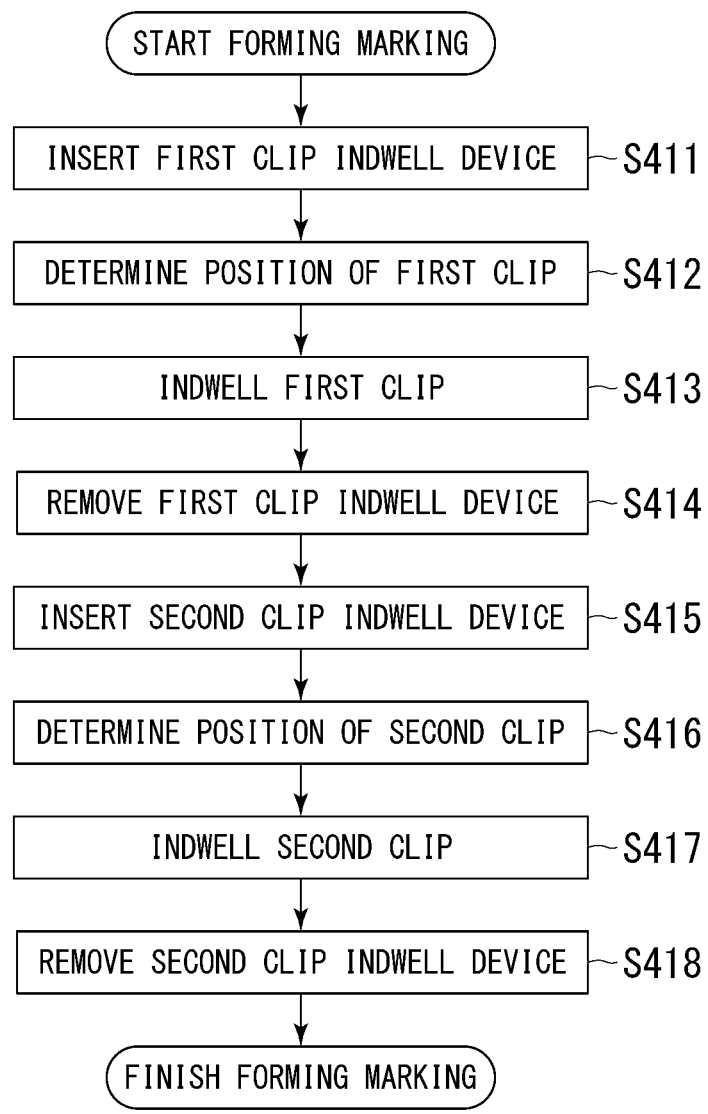
FIG. 29 is a view showing a flowchart of a marking step in a modification example 1-3 of the resection method.
Figure 30:
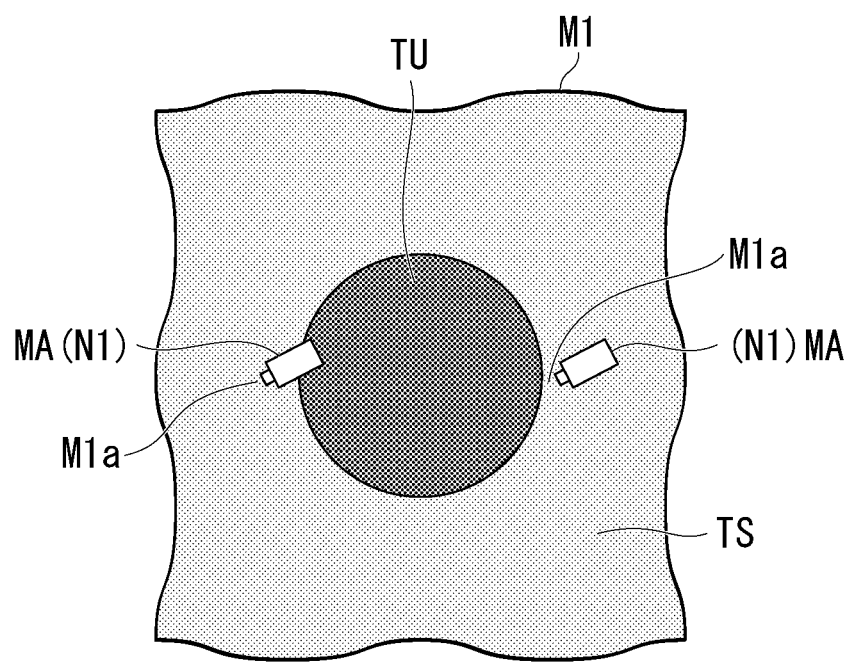
FIG. 30 is a view showing a marking step in the modification example 1-3 of the resection method.
Figure 31:
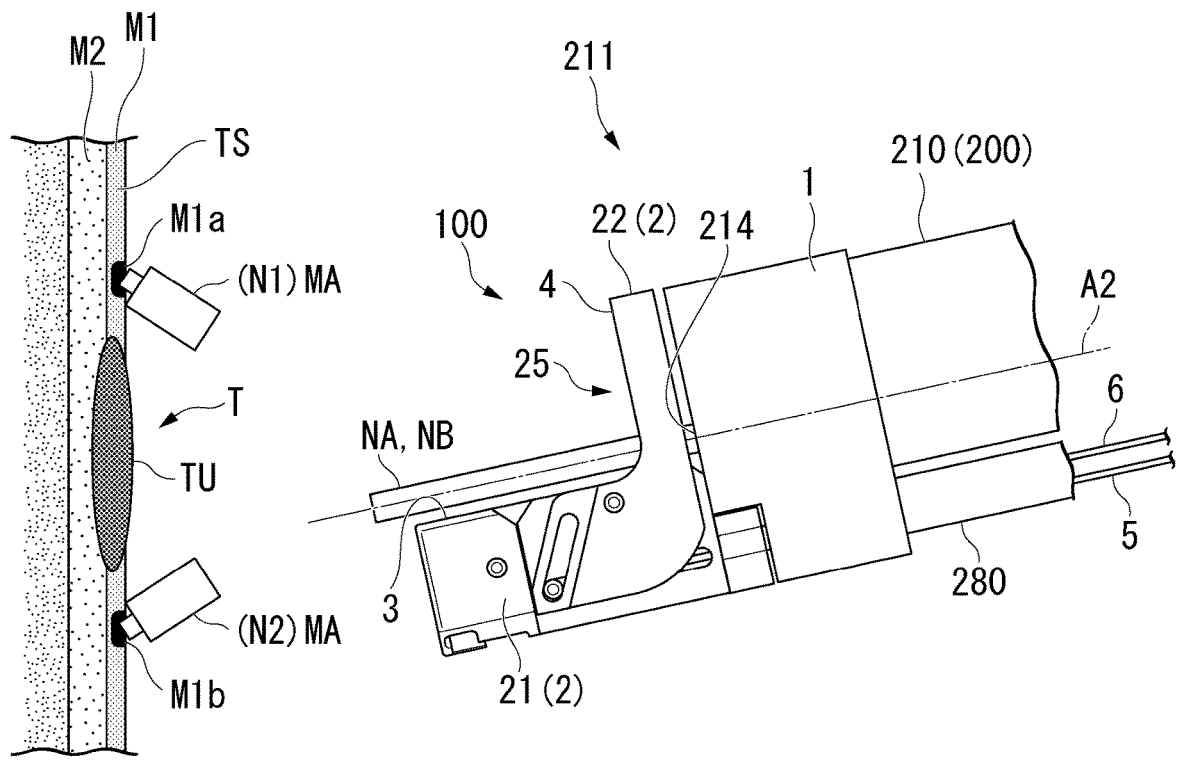
FIG. 31 is a view showing the marking step in the modification example 1-3 of the resection method.
Figure 32:
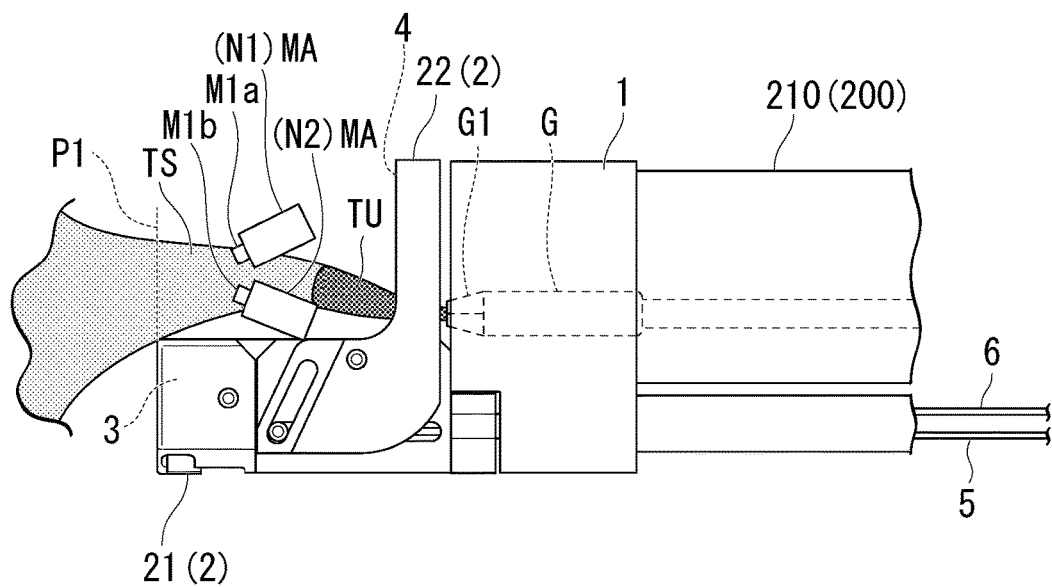
FIG. 32 is a view showing a retracting step in the modification example 1-3 of the resection method.
Figure 33:
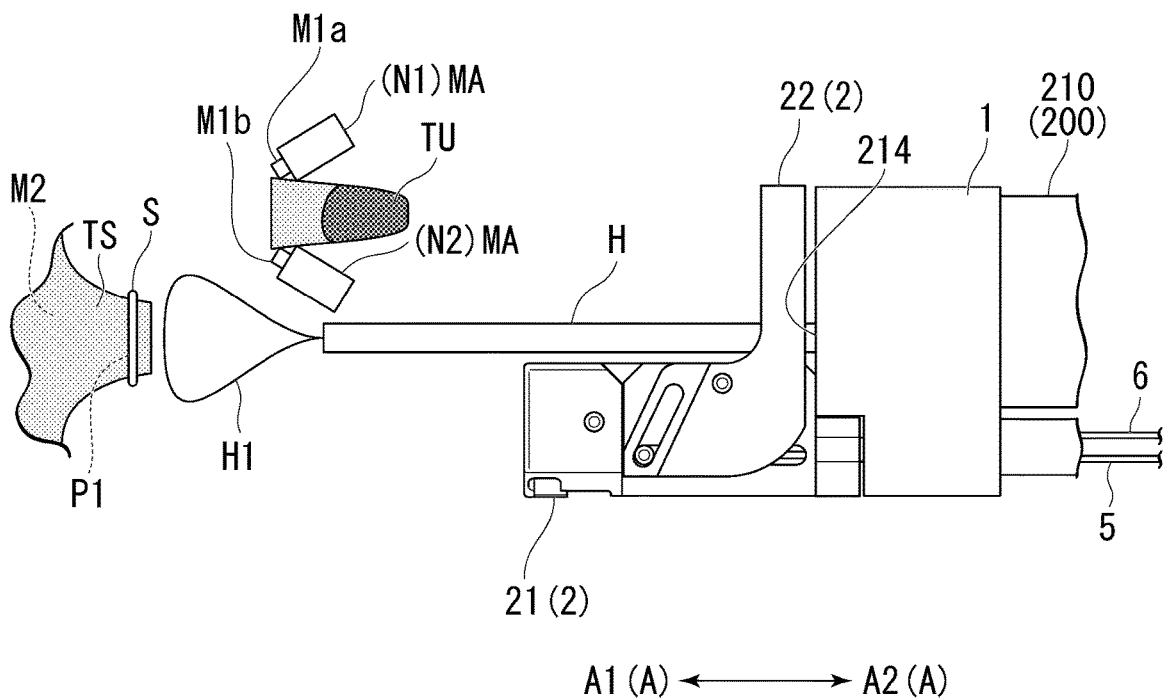
FIG. 33 is a view showing a resecting step in the modification example 1-3 of the resection method.
Figure 34:
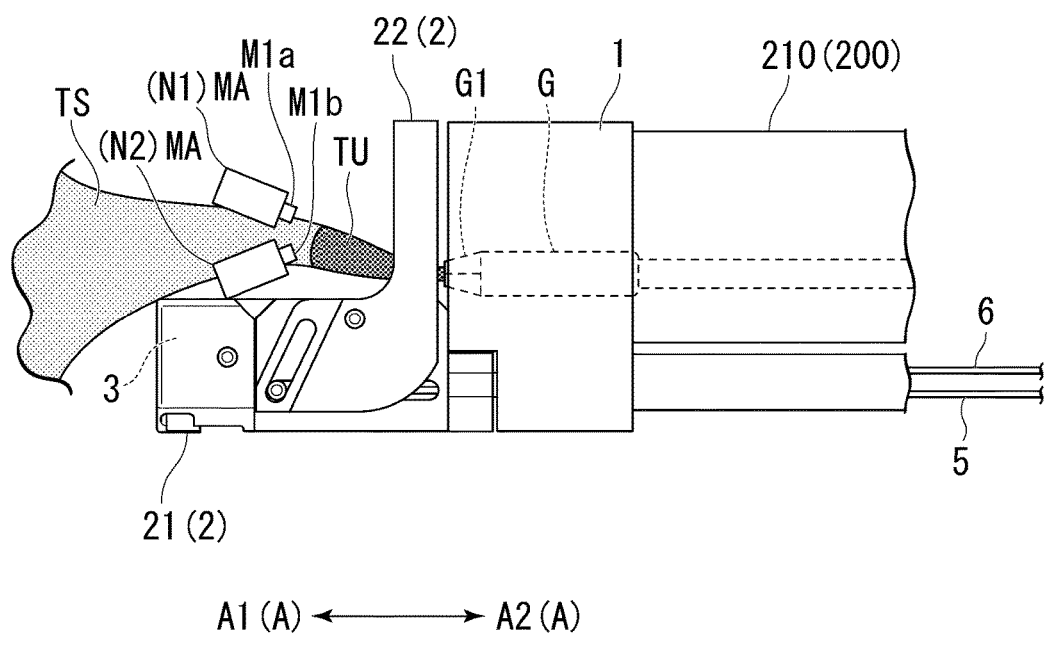
FIG. 34 is a view showing another example of the marking step and the retracting step in the modification example 1-3 of the resection method.

FIG. 29 is a flowchart showing the marking step according to the modification example 103 in the lesion resection method. FIG. 30 is a view showing the marking step of the modification example 1-3 in the lesion resection method. FIG. 31 is a view showing the marking step of the modification example 1-3 in the resection method. FIG. 32 is a view showing a retracting step of the modification example 1-3 in the resection method. FIG. 33 is a view showing a resecting step of the modification example 1-3 in the resection method. FIG. 34 is a view showing other examples of the marking step and the retracting step in the resection method.

In the first embodiment, it is described that one clip N1 is indwelled in the peripheral tissues TS of the tumor TU in the marking step, however, the aspect of the marking step is not limited thereto.

According to the modification example 1-3, the marking step (Step S4) shown in FIG. 12 and FIG. 13 may be replaced with the procedures shown in FIG. 29. The method for forming the three-dimensional marking in the modification example 1-3 of the first embodiment will be described based on the flowchart in FIG. 29. The method except for the points described below is the same with that of the above-described first embodiment and the description will be omitted.

As shown in FIG. 29, in the marking step in the modification example 1-3, as shown in FIG. 29, the first clip indwelling device NA is inserted into the treatment channel 230 (see FIG. 1) (Step S411), as shown in FIG. 30, the position of the first clip N1 is determined at the first part M1a of the mucosa layer M1 in the peripheral tissues TS (Step S412), and the first clip N1 is indwelled (Step S413). Thereafter, until the first clip indwelling device NA is removed from the treatment channel 230 (Step S414), the procedures are the same with that of the first embodiment.

In the present modification example, after the first clip indwelling device NA is removed, the second clip indwelling device NB is inserted into the treatment device channel 230 (Step S415), and the second clip N2 is protruded from the forceps port 214.

When the grasping portion 2 is in the open state, the central axis A2 of the forceps port 214 passes through the visual field space 25 such that it is possible to make the second clip N2 of the second clip indwelling device NB to approach the tumor TU as the treatment target T.

The surgeon bends the insertion portion 210 of the endoscope 200 and tilt the second clip N2 to an arbitrary direction to determine the position thereof (Step S416).

Here, an example in which the second clip N2 is indwelled such that the distal end of the second clip N2 is directed to the direction separating from the tumor TU will be described. In other word, it is an example in which the second clip N2 is indwelled such that the proximal end of the second clip N2 is directed to the direction approaching the tumor TU.

After determining the position of the second clip N2, the surgeon pushes the second clip N2 to the second part M1b of the peripheral tissues TS while operating the second clip indwelling device NB, as shown in FIG. 31, to indwell the second clip N2 at the second part M1b (Step S417).

Here, the second part M1b of the peripheral tissues TS is the part positioned at the lower side of the tumor TU in the visual field of the endoscope when the grasping forceps G is retracted into the medical stapler 100 in the retracting step (Step S8).

A preferable positional relationship between the first part M1a of the peripheral tissues TS and the second part M1b of the peripheral tissues TS is that the second part M1b is at the opposite side of the first part M1a of the peripheral tissues TS to sandwich the tumor TU therebetween.

Next, the surgeon removes the second indwelling device NB from the treatment channel 230 (Step S418).

Thereafter, as same as the first embodiment, the resection of the target tissues (tumor TU) is performed. Only the different part of each step from that of the first embodiment will be described.

<Retracting Step>

FIG. 27 is a view showing a retracting step of the modification example 1 of the resection method.

As described above, after removing the second clip indwelling device NB from the treatment device channel 230, the surgeon inserts the grasping forceps G into the treatment channel 230. Subsequently, after the tumor TU is grasped by the forceps portion G1, the surgeon pulls the grasping forceps G to the hand side in the visual field of the endoscope while keeping the same state. At this time, as shown in FIG. 27, the surgeon retracts the grasping forceps G such that the first clip N1 and the second clip N2 are disposed at the hand side of the endoscope 200 with respect to the staple extraction portion 3.

At this time, since the three-dimensional marking (second clip N2) is also indwelled at the second part M1b in the peripheral tissues TS of the tumor TU, when the tumor TU is retracted and the proximal end of the second clip N2 is placed on the second grasping member 22, it is possible for the surgeon to fell the resistance feeling (click feeling). According, the surgeon may understand that the second clip N2 is disposed at the hand side of the endoscope 200 with respect to the staple extraction portion 3 not only by the visual sense but also by the touch sense.

Thereafter, the surgeon operates the open-close operation portion 250 (see FIG. 1) to retract the open-close operation wire 5 to make the grasping portion 2 in the closed state (Step S9; FIG. 12), and clamps the ligation position P1 (see FIG. 19) that is positioned at the outside separating from the tumor TU with respect to the first part M1a to which the first clip N1 is indwelled and the second part M1b to which the second clip N2 is indwelled among the peripheral tissues TS by the staple extraction portion 3 of the first grasping member 21 and the staple reception portion 4 of the second grasping member 22.

<Observing Step>

After the grasping portion 2 is in the closed state, the surgeon observes the positional relationship between the first grasping member 21 and the three-dimensional marking (the first clip N1, the second clip N2) in the visual field of the endoscope (Step S10: FIG. 12).

<Ligating Step>

The surgeon operates the extraction operation portion 270 (see FIG. 1) to pull the extraction operation wire 6 in the state in which the ligation position P1 of the peripheral tissues TS is clamped by the staple extraction portion 3 and the staple reception portion 4 so as to eject the staple S accommodated in the first grasping member 21 toward the staple reception portion 4 of the second grasping member 22 to ligate the ligation position P1 (Step S12: FIG. 12).

<Resecting Step>

FIG. 28 is a view showing the resecting step of the modification example 1 in the lesion resection method.

The surgeon removes the grasping forceps G from the treatment channel 230 in the state in which the tissue is grasped by the grasping portion 2, inserts the high-frequency snare H as the resection treatment device (Step S14: FIG. 12), and protrudes the snare wire H1 provided at the distal end of the high-frequency snare H from the forceps port 214. As shown in FIG. 28, the surgeon resects the part including the whole tumor TU at the hand side (the tumor TU side: A2 side) of the endoscope 200 with respect to the part (ligation position P1) that is ligated by the staple S, and at the distal end side (the opposite side of the tumor TU: A1 side) of the endoscope 200 with respect to the first clip N1 indwelled in the first part M1a of the peripheral tissues TS and the second clip N2 indwelled in the second part M1b. In other words, the part including the whole tumor TU at the hand side (the tumor TU side) of the endoscope 200 with respect to the part ligated by the staple S and at the distal end side of the endoscope 200 (the opposite side of the tumor TU: A1 side) with respect to the positions where the first clip N1 and the second clip N2 are indwelled is resected.

According to the method, when the peripheral tissues TS are resected by the snare wire H1, there are two markings to show the resection line such that the resection line is stable and it is possible to perform the full thickness resection more correctly.

In the above-described modification example 1, the method of indwelling the second clip N2 such that the distal end of the second clip N2 is directed to the direction separating from the tumor TU is described, however, as shown in FIG. 29, the second clip N2 may be indwelled such that the distal end of the second clip N2 is directed to the direction approaching the tumor TU, that is, the proximal end of the second clip N2 is directed to the direction separating from the tumor TU.

According to the method, at the time of the retracting step S8 (Step S12), when the distal end of the second clip N2 is placed on the second grasping member 22, there is less resistance feeling and it is easy for the surgeon to retract the grasping forceps G.

Modification Example 1-4

Figure 35:
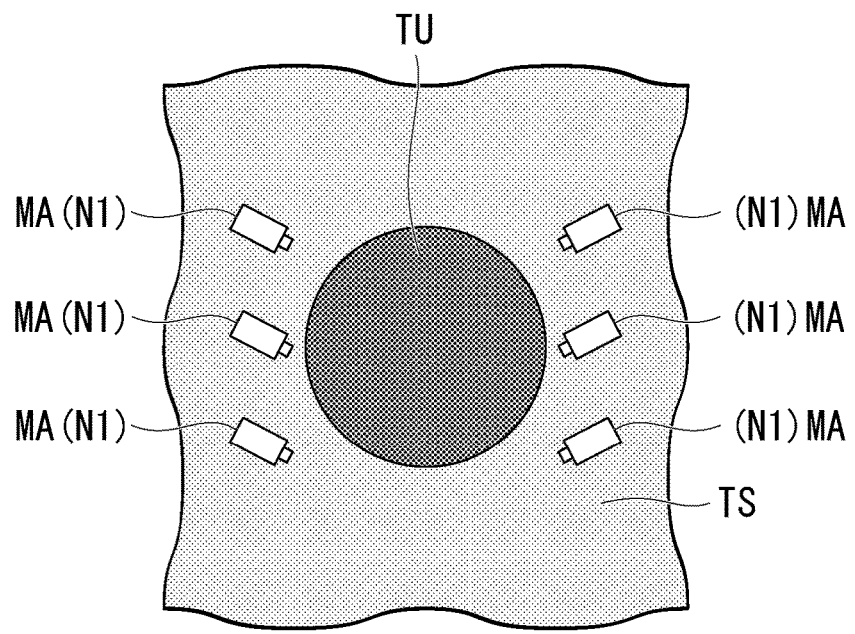
FIG. 35 is a view showing a marking step in a modification example 1-4 of the resection method.
Figure 36:
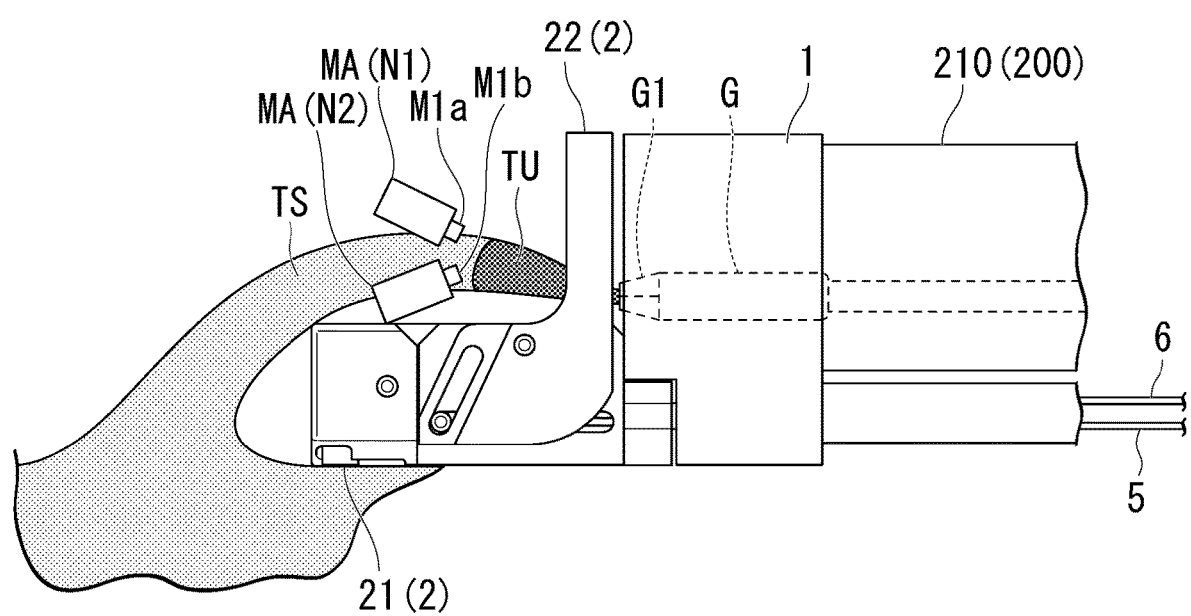
FIG. 36 is a view showing a retracting step in the modification example 1-4 of the resection method.

FIG. 35 is a view showing a marking step in the modification example 1-4 of the resection method. FIG. 36 is a view showing a retracting step in the modification example 1-4 of the resection method.

The marking step of the modification example 1-4 according to the first embodiment is a method adopted in the case when the tumor TU is large, and all of the markings applied around the tumor TU is the three-dimensional markings MA by the clip. As the present modification example, a plurality of the three-dimensional markings MA may be formed around the tumor TU by the clip N1. In FIG. 35, the plurality of clips N1 are disposed at the two sides of the tumor TU such that a pair of the clips N1 are opposite to each other with the tumor TU being sandwiched therebetween; however, the positions for disposing the clip N1 is not limited thereto. The plurality of clips N1 may be disposed at the outer circumference of the tumor TU to surround the tumor TU.

Modification Example 1-5

Figure 37:
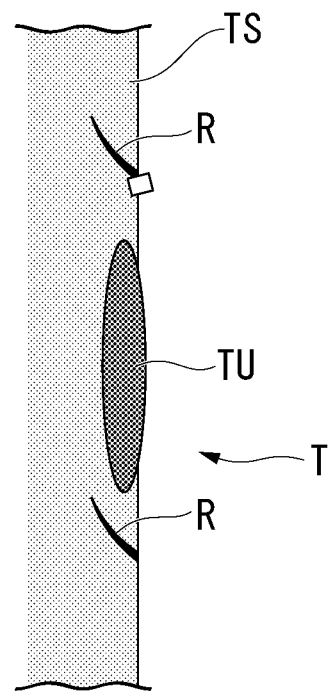
FIG. 37 is a view showing a marking step in a modification example 1-5 of the resection method.
Figure 38:
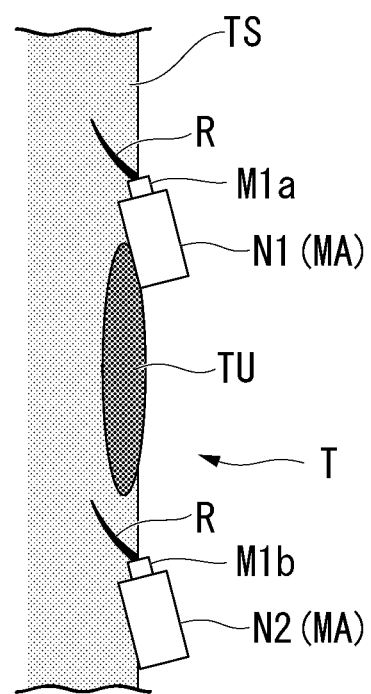
FIG. 38 is a view showing another example of a marking step in the modification example 1-5 of the resection method.

FIG. 37 is a view showing a marking step in the modification example 1-5 of the resection method. FIG. 38 is a view showing another aspect of the marking step in the modification example 1-5 of the resection method.

In the marking step S4 of the modification example 1-5, firstly, the surgeon cuts off part of the peripheral tissues TS of the tumor TU to form the flaps R at two positions, and then forms two of the three-dimensional markings MA by attaching the clip N1 to each flap R.

The flap R is a tissue piece by cutting off part of the mucosa layer M1 and the tissue is not completely resected. The flap R is formed by cutting off part of the mucosa layer M, and the notch does not reach the submucosa layer M2 and the muscular layer M3.

In the present modification example, when the clip N1 is attached to the flap R formed by cutting off part of the mucosa layer M1, the flap R does not have the rigidity for supporting the weight of the clip N1 such that the clip N1 is in a state of falling down.

In this manner, by attaching the clip N1 to the flap R, it is easy for the clip N1 to move even the clip N1 comes into contact with the grasping portion 2 at the time of retracting the tumor TU such that it is possible to prevent the clip N1 from being hooked to the grasping portion 2.

It is described that two of the three-dimensional markings MA by attaching the clip N1 to the flap R; however, the number of the three-dimensional markings MA is not limited thereto, and the number may be one or the number may be equal to or more than three.

Second Embodiment

A second embodiment of the present disclosure will be described referring to FIG. 39 to FIG. 51. In the following description, the common configurations that have been described will be designated with the same references signs and the duplicate description will be omitted. The resection method according to the second embodiment, for example, is performed by using the medical system 300 shown in the first embodiment.

[Usage Method of Medical Stapler 100]

The usage method of the medial stapler 100 (the resection method using the medical stapler 100) will be described.

FIG. 39 to FIG. 51 are views for describing the usage method of the medical stapler 100.

Figure 39:
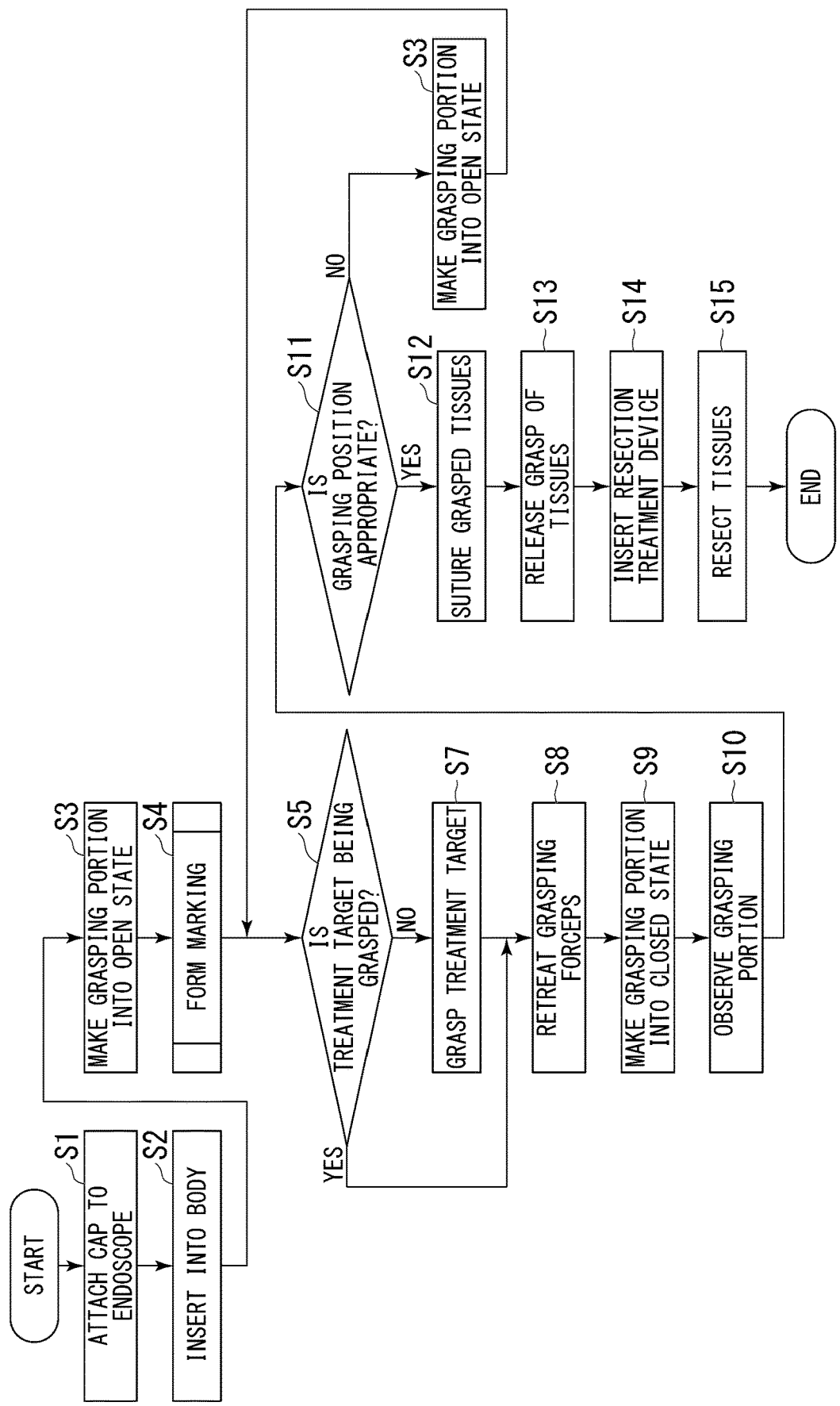
FIG. 39 is a flowchart showing a resection method according to a second embodiment of the present invention.

The lesion resection method according to the present embodiment will be described based on the flowchart showing the whole lesion resection method in FIG. 39 and the three-dimensional marking formation method in FIG. 40.

<Insertion Step>

The surgeon uses the cap 1 included in the medical stapler 100 to attach the medical stapler 100 to the insertion portion 210 of the endoscope 200 (Step S1).

The surgeon inserts the insertion portion 210 of the endoscope 200 to which the medical stapler 100 is attached from the mouth as the natural orifice of the subject (Step S2), and makes the distal end portion 211 to approach the tumor (lesion tissues) TU (see FIG. 14) as the treatment target T.

Next, the surgeon operates the open-close operation portion 250 to advance the open-close operation wire 5 to make the grasping portion 2 into the open state (Step S3).

Even the grasping portion 2 is in the open state, as shown in FIG. 9, the optical axis A1 of the object lens 215 passes through the visual field space 25 such that the surgeon may observe the tumor TU through the imaging unit of the endoscope 200.

<Marking Step>

Next, the surgeon forms the three-dimensional marking in the peripheral tissues TS of the tumor TU as the treatment target T (Step S4). The marking step for forming the three-dimensional marking will be described using FIG. 40.

Figure 40:
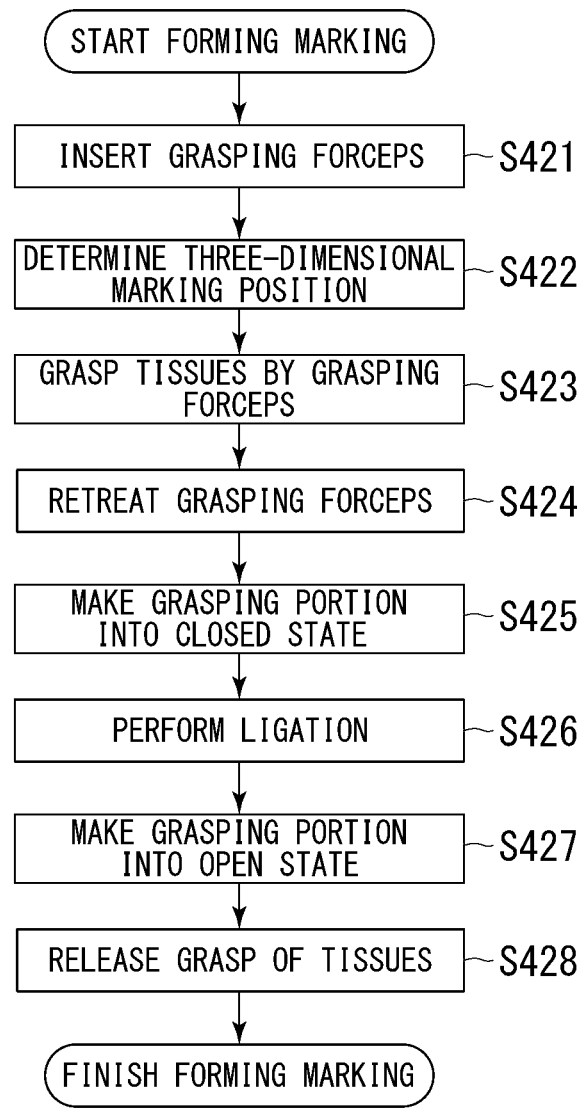
FIG. 40 is a flowchart showing a marking step in the resection method.

As shown in FIG. 40, the surgeon inserts the grasping forceps G into the treatment channel 230 (shown in FIG. 1) (Step S421) and protrudes the forceps portion G1 provided at the distal end of the grasping forceps G from the forceps port 214. The central axis A2 of the forceps port 214 (see FIG. 9) passes through the visual field space 25 such that the forceps portion G1 of the grasping forceps G passes the grasping portion 2 to approach the tumor TU positioned at the distal end side.

The surgeon operates the endoscope 200 to make the forceps portion G1 to approach an arbitrary position of the peripheral tissues TS to determine the position of the marking (Step S422). At this time, the surgeon determines the position of the forceps portion G1 at the outside of the tumor TU with respect the position where the three-dimensional marking is desired to be formed.

Figure 41:
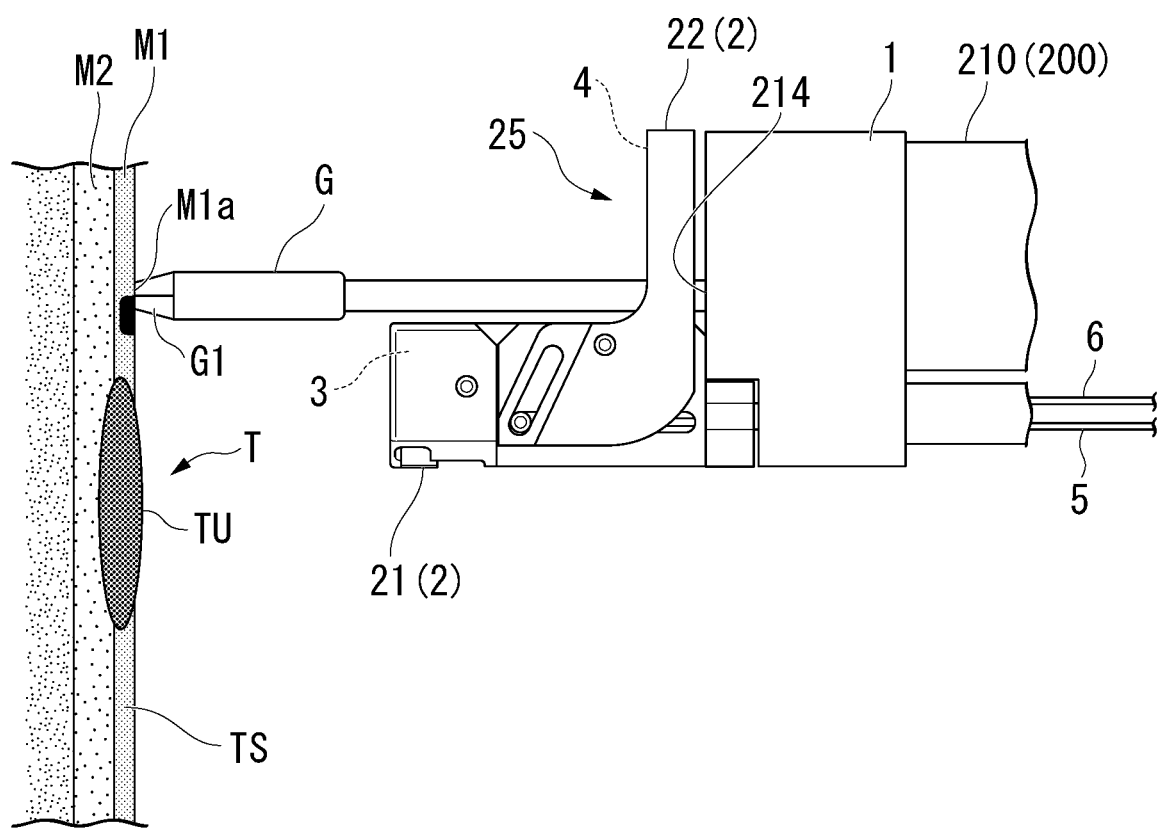
FIG. 41 is a view showing the marking step in the resection method.

Next, as shown in FIG. 41, the surgeon operates the grasping forceps G to make the forceps portion G1 to press the outside of the first part Mia of the peripheral tissues TS so as to grasp the outside of the first part M1a of the peripheral tissues TS by the forceps portion G1 (Step S423).

Here, the first part Mia of the peripheral tissues TS is the part positioned at the upper side of the tumor TU in the visual field of the endoscope when the grasping forceps G is retracted into the medical stapler 100 during the following retracting step (Step S424).

Figure 42:
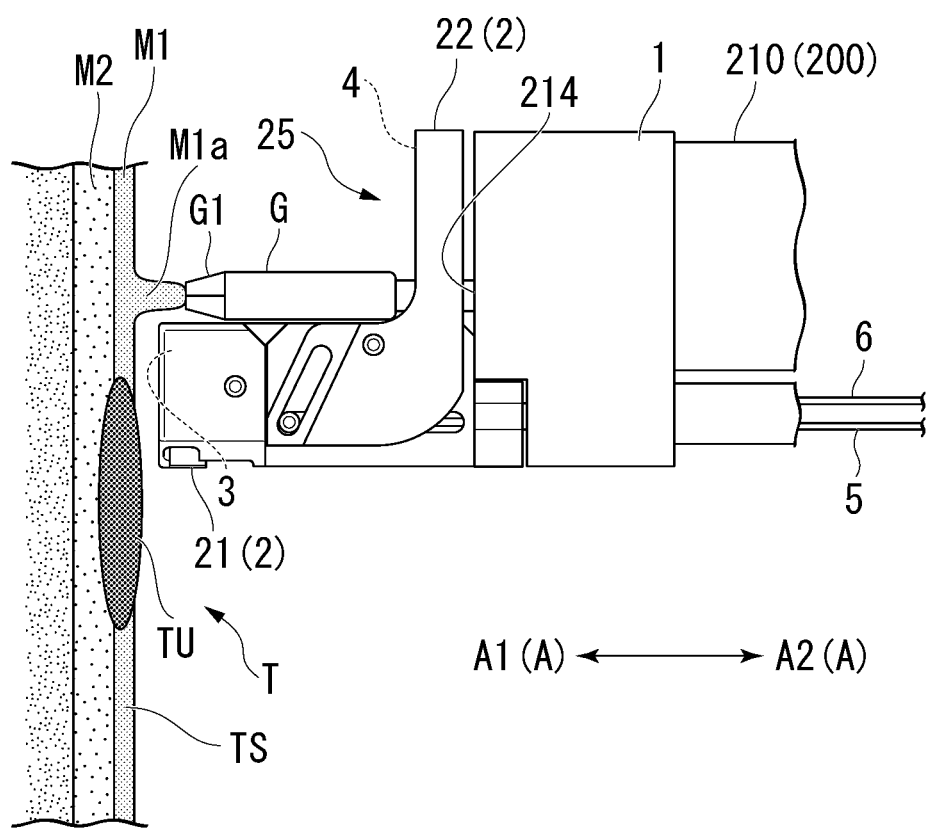
FIG. 42 is a view showing the marking step in the resection method.

Subsequently, as shown in FIG. 42, in the state in which the outside of the first part M1a of the peripheral tissues TS is grasped by the grasping forceps G, the surgeon pulls the grasping forceps G to the hand side of the surgeon to retract the grasping forceps (Step S424). At this time, the surgeon pulls the distal end of the forceps portion G1 to the endoscope side (the proximal end side of the grasping forceps G, the hand side of the surgeon) with respect to the staple extraction portion 3.

Figure 43:
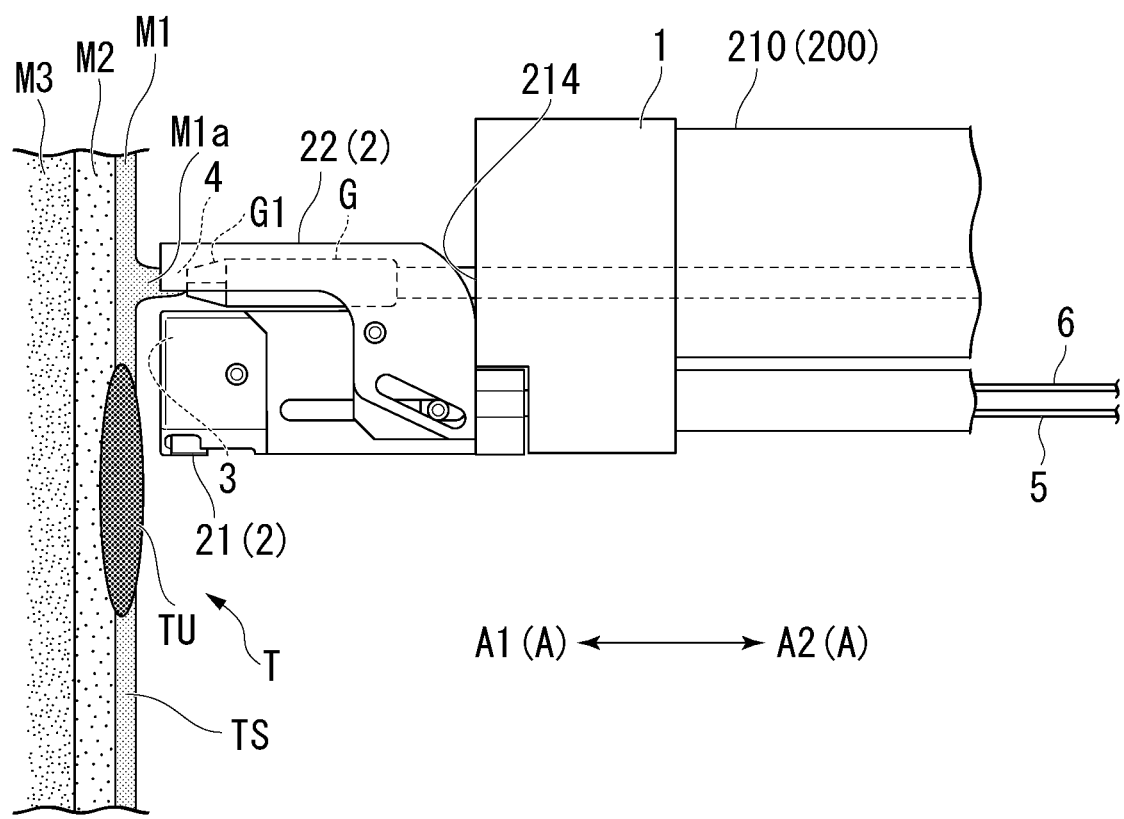
FIG. 43 is a view showing the marking step in the resection method.

Subsequently, as shown in FIG. 43, the surgeon operates the open-close operation portion 250 to retract the open-close operation wire 5 and makes the grasping portion 2 into the closed state (Step S425). The surgeon clamps the first part M1a of the peripheral tissues TS by the staple extraction portion 3 of the first grasping member 21 and the staple reception portion 4 of the second grasping member 22.

At this time, the surgeon confirms whether the tumor TU is pulled to the endoscope side with respect to the staple extraction portion 3. In the case in which the tumor TU together with the first part M1a are pulled to the endoscope side with respect to the staple extraction portion 3, the surgeon makes the grasping portion 2 into the open state again with the outside of the first part M1a of the peripheral tissues TS being in the state of being grasped by the grasping forceps G.

Thereafter, the surgeon operates the open-close operation portion 250 to retract the open-close operation wire 5 and advance the grasping forceps G so as to return the tumor TU that is pulled together with the first part M1a to the outside of the staple extraction portion 3.

Subsequently, the surgeon pulls the grasping forceps G to the hand side of the surgeon in the state in which the outside of the first part M1a of the peripheral tissues TS is grasped by the grasping forceps G so as to retract the grasping forceps G again (Step S424) and make the peripheral tissues TS including the first part Mia only to be at the endoscope side with respect to the staple extraction portion 3 of the first grasping member 21.

Subsequently, the surgeon operates the open-close operation portion 250 to retract the open-close operation wire 5 so as to make the grasping portion 2 to be in the closed state again as shown in FIG. 43 (Step S425).

Figure 44:
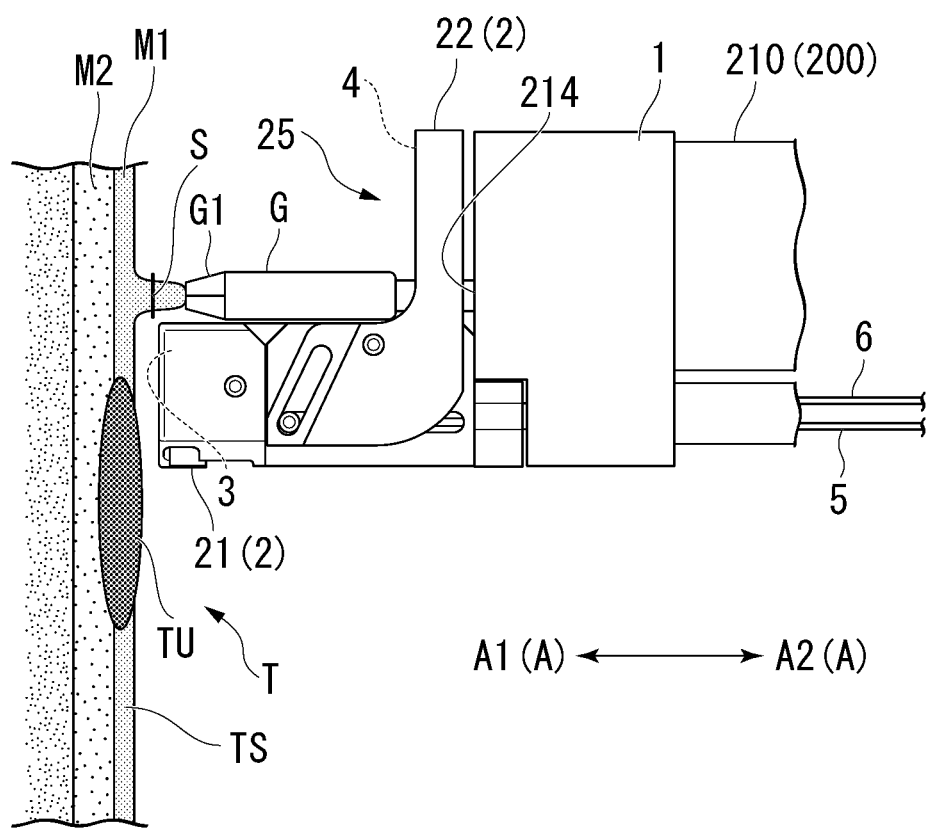
FIG. 44 is a view showing the marking step in the resection method.

Next, as shown in FIG. 43, the surgeon operates the extraction operation portion 270 (shown in FIG. 1) in the state in which the peripheral tissues TS including the first part M1a thereof is clamped by the staple extraction portion 3 and the staple reception portion 4 to pull the extraction operation wire 6 so as to eject the staple S accommodated in the first grasping member 21 toward the staple reception portion 4 of the second grasping member 22 to ligate the peripheral tissues TS (Step S426). As shown in FIG. 44, part of the peripheral tissues TS is raised up to form the three-dimensional marking L1 by ligating the peripheral tissues TS.

At this time, the surgeon determines the size of the formed three-dimensional marking 11 due to the volume of the peripheral tissues TS that is pulled into the medical stapler 100 in the above-described Step S424. In other words, when the grasping portion 2 is in the closed state, the three-dimensional marking L1 is raised up and easy to be visually confirmed as the volume of the peripheral tissues TS that is retracted to the endoscope side with respect to the staple extraction portion 3 is large.

Subsequently, as shown in FIG. 44, the surgeon operates the open-close operation portion 250 to make the grasping portion 2 into the open state again (Step S427). The surgeon opens the forceps portion G1 of the grasping forceps G to release the grasping with respect to the peripheral tissues TS including the first part Mia (Step S428).

Here, it is described to release the grasping with respect to the peripheral tissues TS by the grasping forceps G after the ligation of the peripheral tissues TS, however, the grasping forceps G may be separated from the peripheral tissues TS at any timing after the grasping portion 2 is in the closed state (Step S425).

As described above, the marking step is performed.

<Grasping Step>

Figure 45:
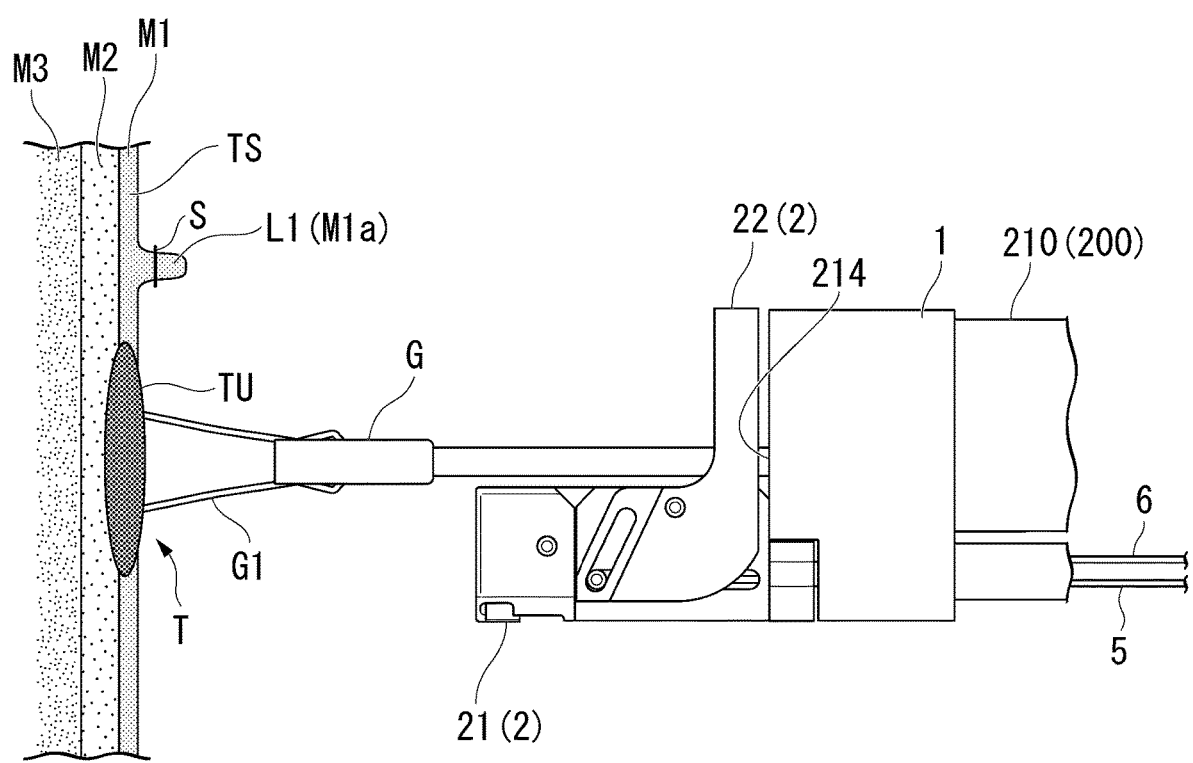
FIG. 45 is a view showing a retracting step in the resection method.

Subsequently, as shown in FIG. 45, the surgeon presses the forceps portion G1 to the tumor TU and close the forceps portion G1 to grasp the tumor TU (Step S7).

<Retracting Step>

Figure 46:
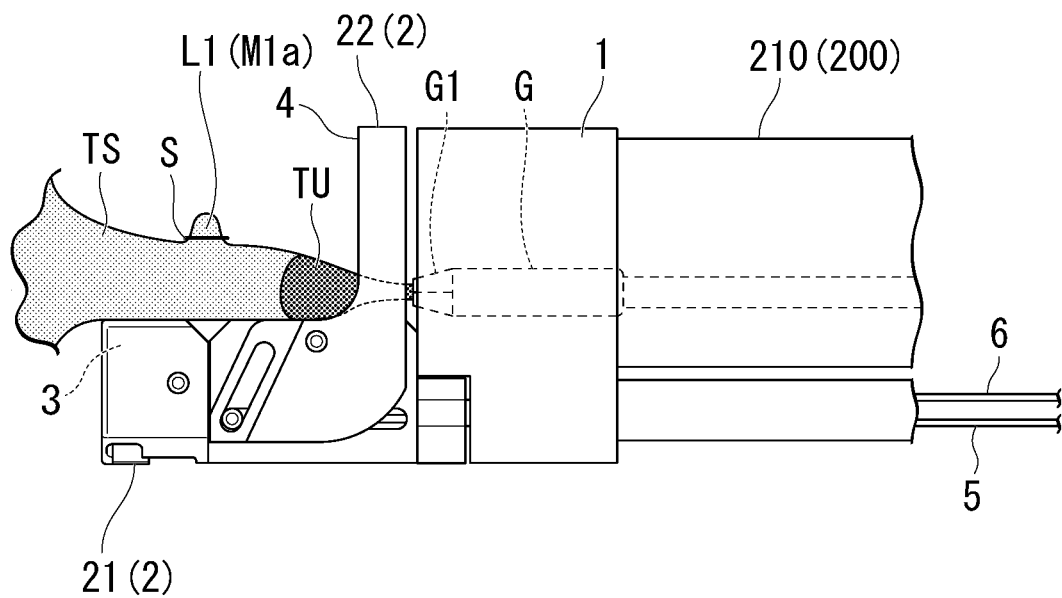
FIG. 46 is a view showing a retracting step in the resection method.

The surgeon retracts the grasping forceps G with the forceps portion G1 grasping the tumor TU at the distal end thereof to the hand side in the visual field of the endoscope (the proximal end side of the endoscope, the proximal end side of the grasping forceps, and the proximal end of the medical stapler). As shown in FIG. 46, the surgeon retracts the grasping forceps G to the proximal end side in the state in which the tumor TU is grasped by the forceps portion G1 (Step S8). The surgeon retracts the grasping forceps G such that the distal end of the grasping forceps G is disposed at the proximal end side with respect to the staple extraction portion 3. It is preferable that the grasping forceps G is retracted such that the three-dimensional marking 11 is disposed at the proximal end side of the staple extraction portion 3.

Figure 47:
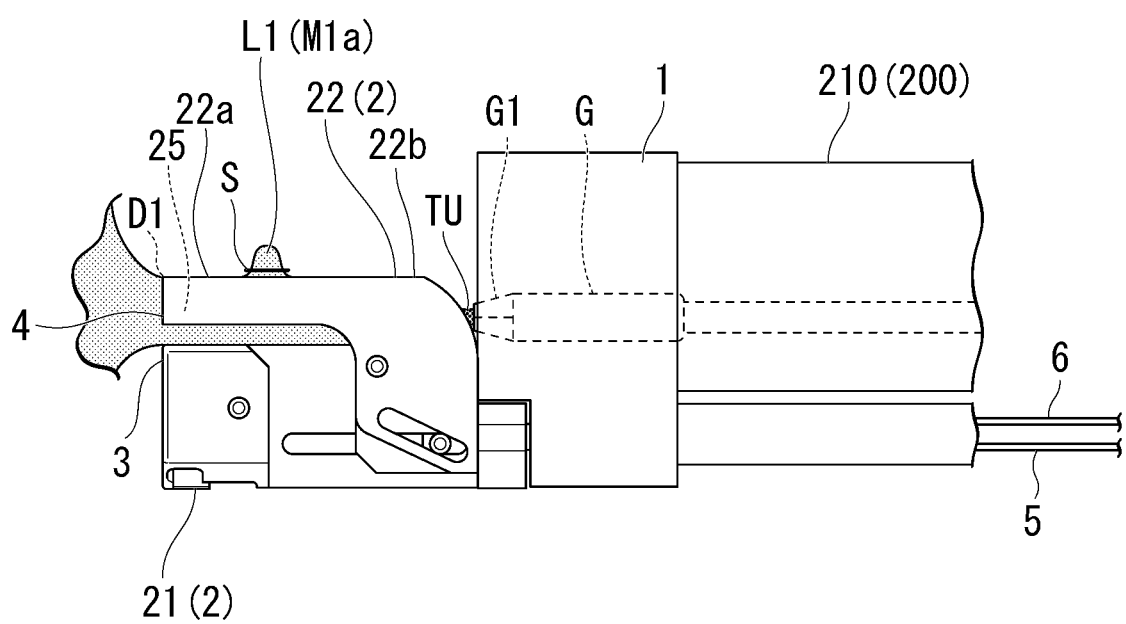
FIG. 47 is a view showing a retracting step in the resection method.
Figure 48:
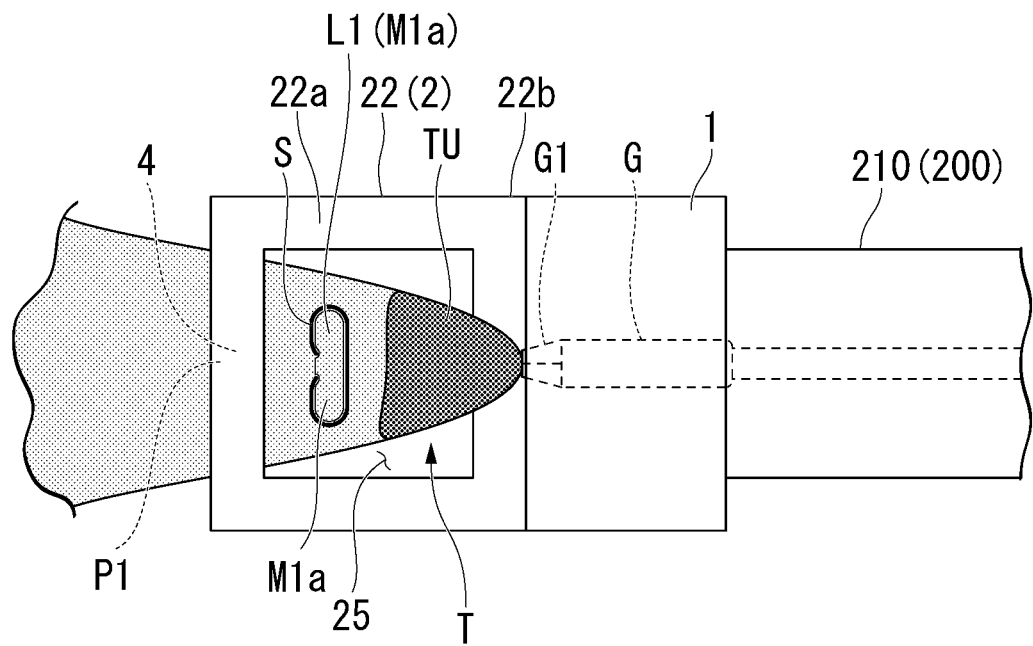
FIG. 48 is a top view showing a retracting step in the resection method.

The surgeon operates the open-close operation portion 250 to retract the open-close operation wire 5 to make the grasping portion 2 into the closed state as shown in FIG. 47 (Step S9). The surgeon clamps the ligation position P1 (see FIG. 48) positioned at the outside of the tumor TU with respect to the first part M1a of the peripheral tissues TS by the staple extraction portion 3 of the first grasping member 21 and the staple reception portion 4 of the second grasping member 22.

The surgeon clamps the ligation position P1 positioned at the outside of the tumor TU by the staple extraction portion 3 and the staple reception portion 4. Accordingly, the tumor TU positioned at the inside of the first part M1a of the peripheral tissues TS, that is, the whole tumor TU is disposed at the proximal end side with respect to the staple extraction portion 3.

When the grasping portion 2 is in the closed state, the tumor TU and the three-dimensional marking L1 disposed at the proximal end side of the staple extraction portion 3 are accommodated in the space (visual field space 25) formed by the U-shaped member 22a and the second main body portion 22b of the second grasping member 22 such that the grasping operation by the first grasping member 21 and the second grasping member 22 is not interfered.

<Observing Step>

After the grasping portion 2 is in the closed state, the surgeon observes the positional relationship between the first grasping member 21 and the three-dimensional marking L1 in the visual filed of the endoscope (Step S10). As shown in FIG. 9, the optical axis A1 of the object lens 215 passes through the upper side B1 of the first grasping member 21 and the second grasping member 22. Accordingly, even the grasping portion 2 is in the closed state, the surgeon is able to observe the treatment target T through the imaging unit of the endoscope 200.

Subsequently, according to the observation result, the surgeon determines whether the position grasped by the grasping portion 2 is appropriate (Step S11). If the position grasped by the grasping portion 2 is appropriate (Step S11: Yes), the ligating step described below will be performed.

On the other hand, in a case in which the position grasped by the grasping portion 2 is inappropriate (Step S11: No), the surgeon opens the first grasping member 21 with the tumor TU being grasped by the grasping forceps G (Step S3) to perform the position adjustment. As an example in which the position grasped by the grasping portion 2 is inappropriate, a case in which the grasping portion 2 overlaps the three-dimensional marking L1, a case in which the grasping portion 2 is significantly separated from the three-dimensional marking 11, and other cases in which the grasping position is not the desired position by the surgeon can be considered. The Step S10 and the Step S11 may be omitted.

Figure 49:
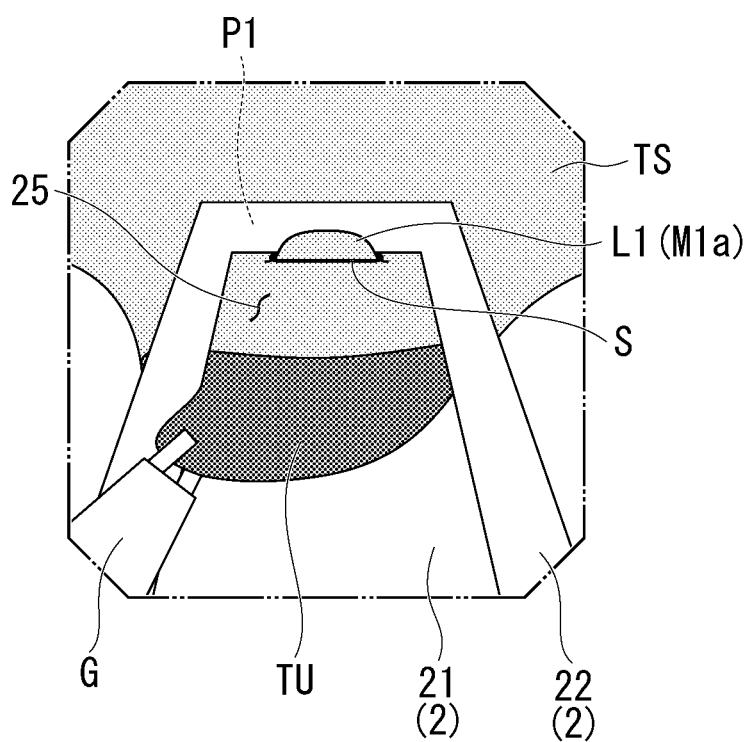
FIG. 49 is a view showing a view field of an endoscope in the retracting step in the resection method.

FIG. 49 is a view showing the visual field of the endoscope when the ligation position P1 is clamped by the staple extraction portion 3 of the first grasping member 21 and the staple reception portion 4 of the second grasping member 22.

The three-dimensional marking L1 formed by the first part M1a of the peripheral tissues TS is three-dimensional such that it is easy to visually confirm the front-rear relationship between the second grasping member 22 and the three-dimensional marking L1 in the visual field of the endoscope. Accordingly, it is possible to understand that the deep side with respect to the three-dimensional marking 11 is grasped in the visual field of the endoscope and it is possible to perform the full thickness resection more correctly.

<Ligating Step>

The surgeon ejects the accommodated staple S toward the staple reception portion 4 and performs the ligation (Step S12) by operating the extraction operation portion 270 to pull the extraction operation wire 6 in the state in which the ligation position P1 is clamped by the staple extraction portion 3 and the staple reception portion 4. The needle tip S1 of the staple S penetrates the ligation position P1 to come into contact with the pocket 41 of the staple reception portion 4 to be bent. As a result, the ligation position P1 is ligated.

Figure 50:
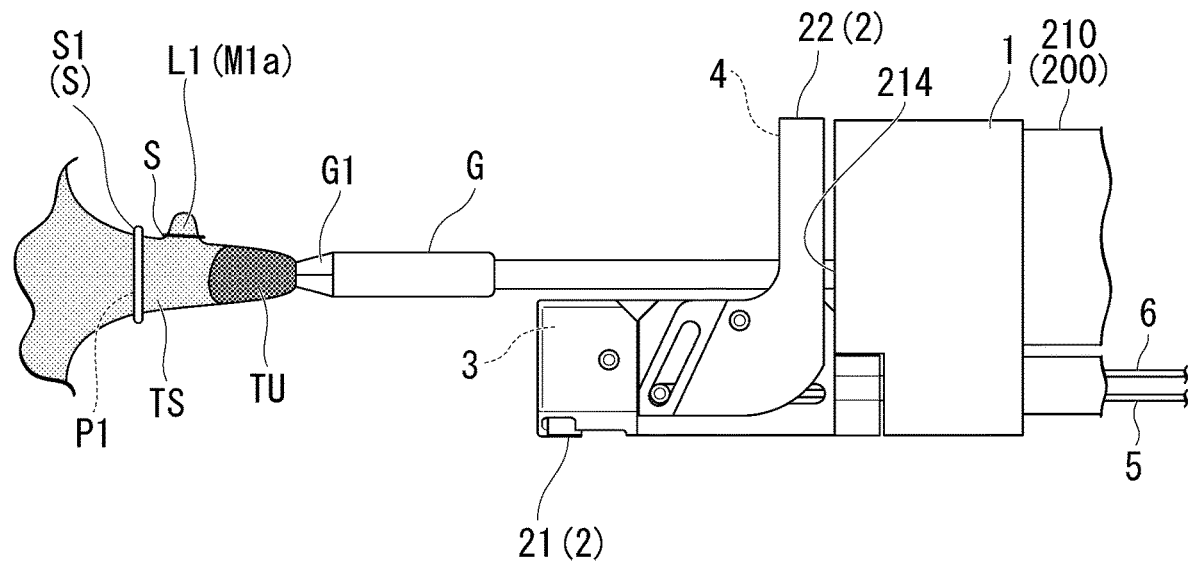
FIG. 50 is a view showing a ligating step in the resection method.

As shown in FIG. 50, the surgeon operates the open-close operation portion 250 to make the grasping portion 2 to be in the open state again. The surgeon opens the grasping forceps G to separate the grasping forceps G from the tumor TU (Step S13).

Here, it is described to separate the grasping forceps G from the tumor TU after ligating the tissues, however, the grasping forceps G may be separated from the tumor TU at any timing after the grasping portion 2 is in the closed state in the retracting step.

<Resecting Step>

Figure 51:
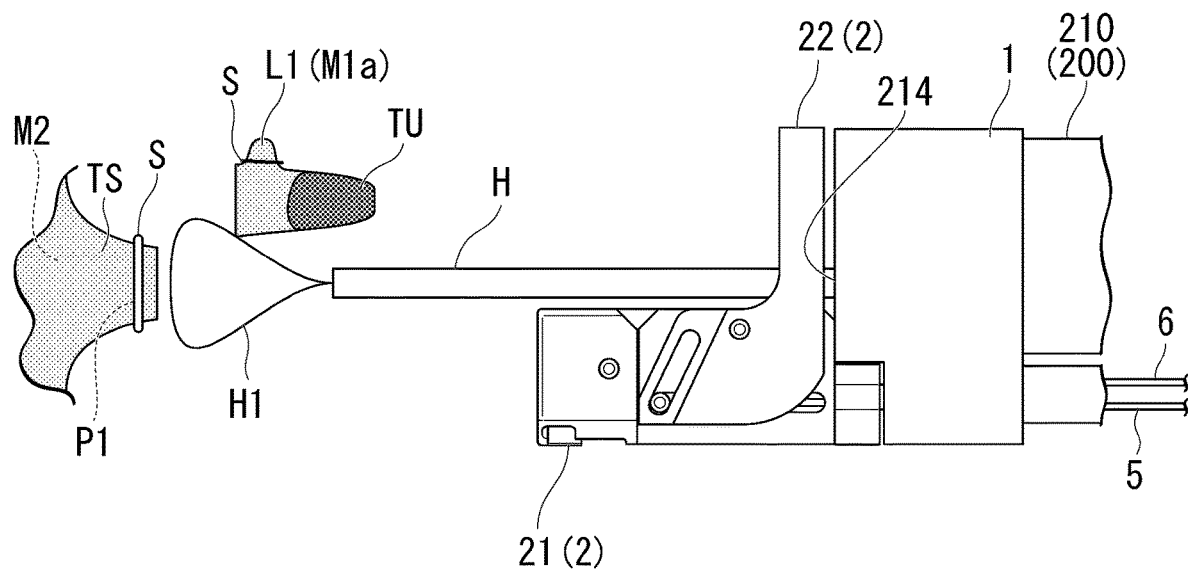
FIG. 51 is a view showing a resecting step in the resection method.

The surgeon removes the grasping forceps G from the treatment channel 230, inserts the high-frequency snare H as the resection treatment device as shown in FIG. 51 (Step S14), and protrudes the snare wire H1 provided at the distal end of the high-frequency snare H from the forceps port 214.

Subsequently, as shown in FIG. 51, the surgeon resects the part including the tumor TU at the proximal end side (the tumor TU side) with respect to the part ligated by the staple S and at the distal end side (the opposite side with respect to the tumor TU) with respect to the first part M1a of the peripheral tissues TS. More specifically, the surgeon resects the part including the tumor TU and excluding the ligated part. The tumor TU is disposed at the proximal end side of the ligated part (the ligation position P1) such that the surgeon may definitely resect the whole tumor TU without any part left. Even the tumor TU is large to reach the submucosa layer M2, the surgeon may definitely resect the whole tumor TU without any part left.

The surgeon collects the resected tumor TU to finish the resecting treatment.

As described above, according to the resection method of the present embodiment, when the first grasping member 21 and the second grasping member 22 grasp the peripheral tissues TS, it is easy to visually confirm whether the three-dimensional marking L1 is at the front side of the first grasping member 21 when viewed from the retraction direction by the grasping forceps G. Accordingly, it is possible to definitely retract the three-dimensional marking L1 positioned at the outside of the tumor TU into the medical stapler 100 and ligate the ligation position P1 positioned at the outside of the first part M1a of the peripheral tissues TS. Accordingly, the surgeon may definitely resect the whole tumor TU without any part left.

Figure 52:
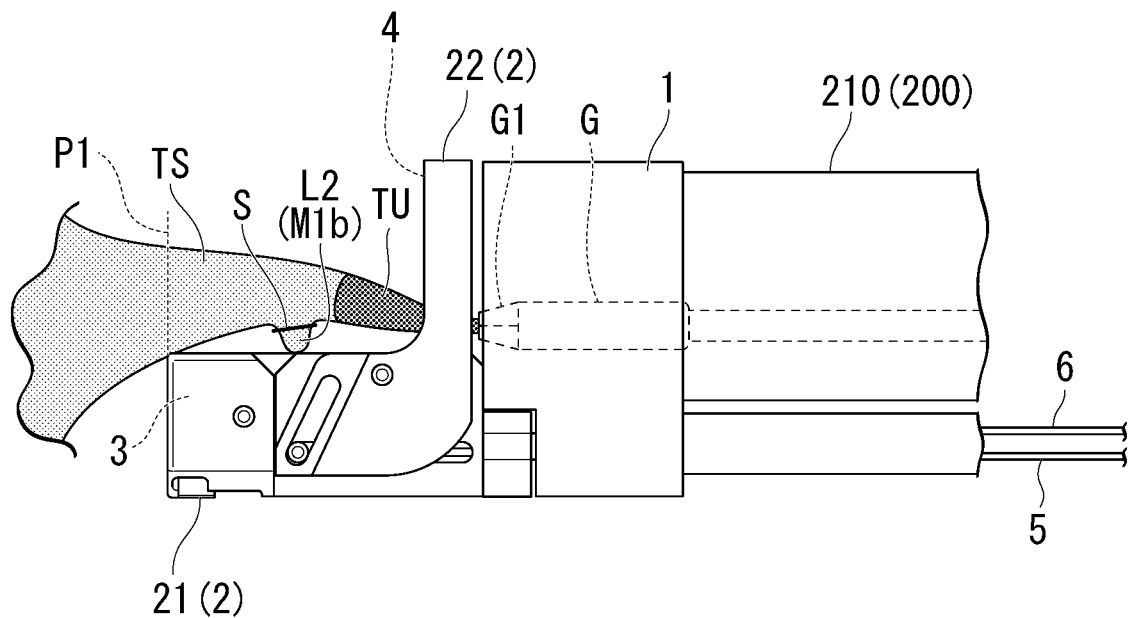
FIG. 52 is a view showing another example of the retracting step in the resection method.

In the present embodiment, the method of indwelling the three-dimensional marking L1 in the first part M1a of the peripheral tissues TS is described, however, as shown in FIG. 52, the three-dimensional marking L1 may be formed in the second part M1b of the peripheral tissues TS.

Herein, the second part M1b of the peripheral tissues TS is the part positioned at the lower side of the peripheral tissues TS when viewed from the retraction direction of the grasping forceps G (the visual field of the endoscope) and when the grasping forceps G is retracted into the medical stapler 100 in the retracting step (Step S8).

According to the method, at the time of pulling the tumor TU by the grasping forceps G (Step S8), the second grasping member 22 comes into contact with the three-dimensional marking L1 and provides the resistance feeling (click feeling) to the surgeon. Accordingly, it is possible to notify the surgeon that the second part M1b of the peripheral tissues TS is retracted with respect to the staple extraction portion 3.

Although the second embodiment of the present disclosure has been described above referring to the figures, the technical scope of the present disclosure is not limited to the above-described embodiment, and various changes or deletion may be made to each component within a range that does not deviate from the gist of the present invention. The configuration elements shown in the above-described embodiment and the modification example may be appropriately combined.

According to the present embodiment, one of the three-dimensional marking L1 is indwelled in the circumference of the tumor TU, however, the aspect of the marking step such as the number and the position of the three-dimensional marking L1 are not limited thereto.

Modification Example 2-1

Figure 53:
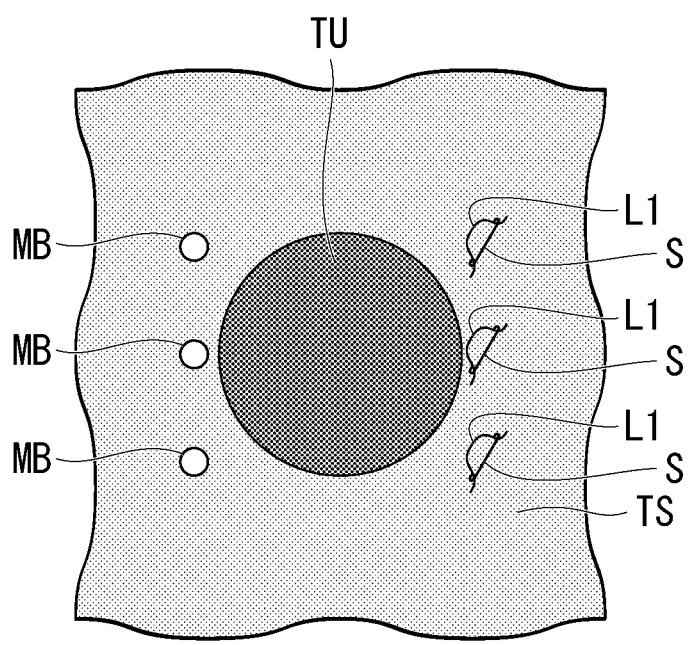
FIG. 53 is a view showing a marking step in a modification example 2-1 of the resection method.

FIG. 53 is a view showing a marking step in the modification example 2-1 of the resection method.

The marking step S4 in the modification example 2-1 is adopted in the case when the tumor TU is large. More specifically, a plurality of three-dimensional markings L1 by the staples S and a plurality of planar markings MB by the cauterization are formed. In the present modification example, triple of three-dimensional markings L1 and triple of planar markings MB are formed respectively, however, the number is not limited thereto. It is not necessary for the ratio of the number to be the same.

Accordingly, with the plurality of three-dimensional markings L1, MB as the visual marks, it is possible to perform the retracting step and the ligating step for several times so as to divide the whole tumor TU into multiple parts to ligate and resect. Accordingly, it is possible to resect the whole large tumor TU efficiently without any part left.

Modification Example 2-2

Figure 54:
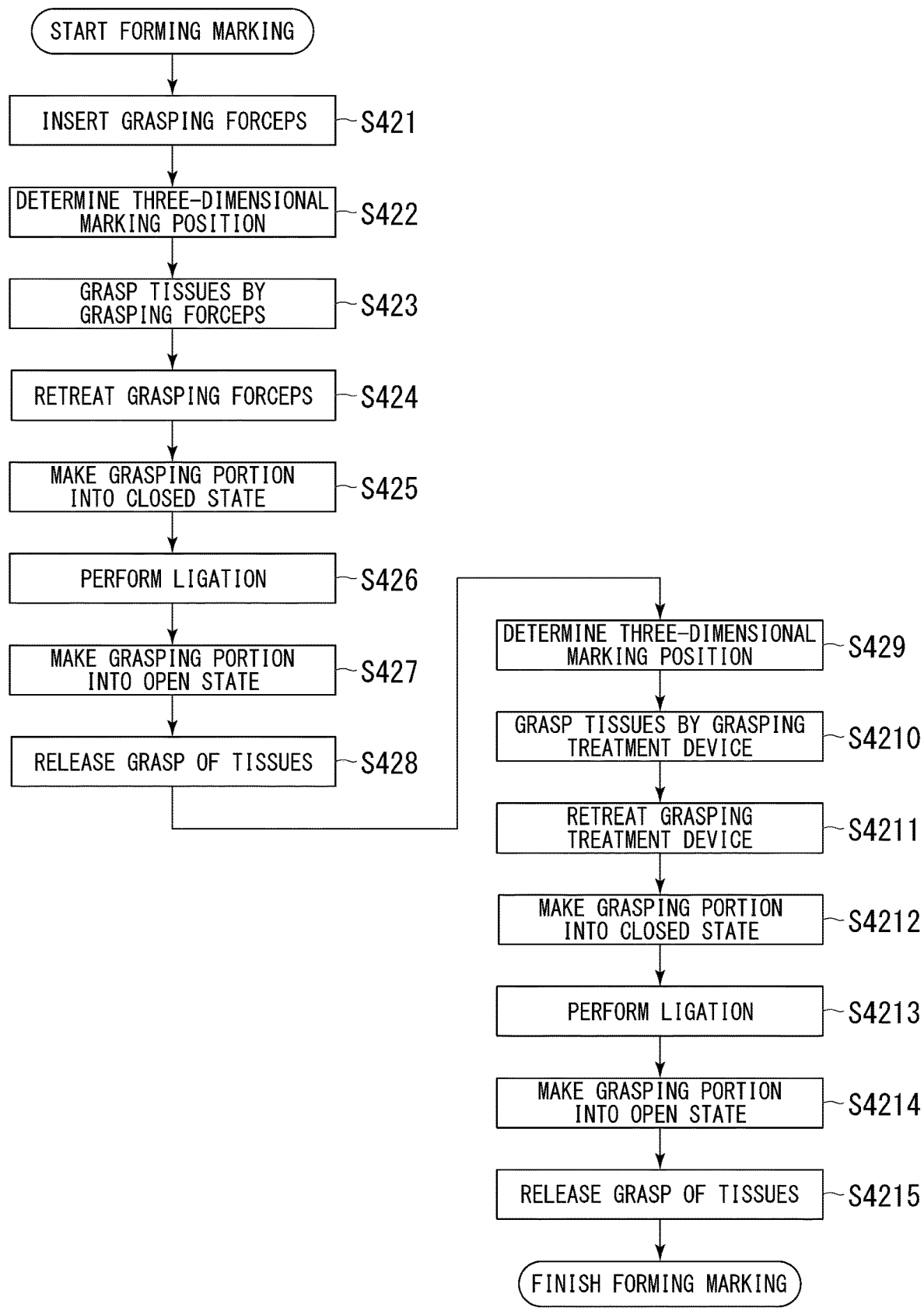
FIG. 54 is a flowchart showing a marking step in a modification example 2-2 of the resection method.
Figure 55:
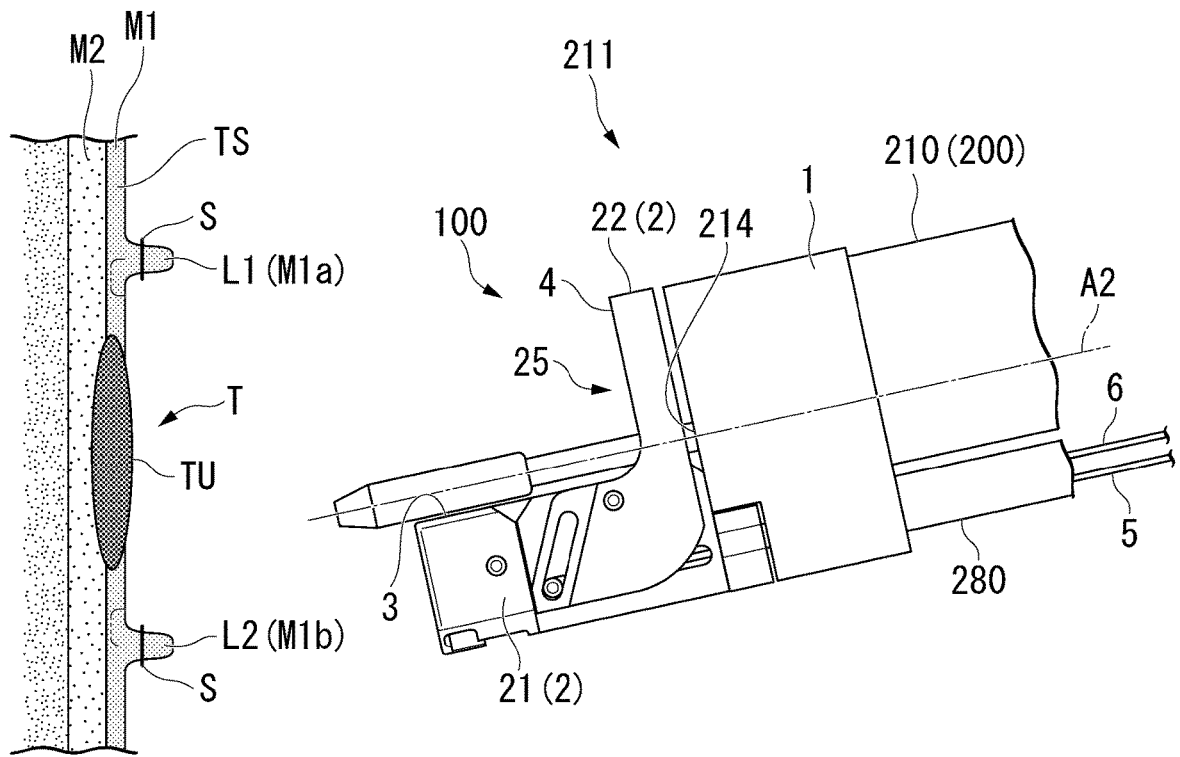
FIG. 55 is a view showing the marking step in the modification example 2-2 of the resection method.
Figure 56:
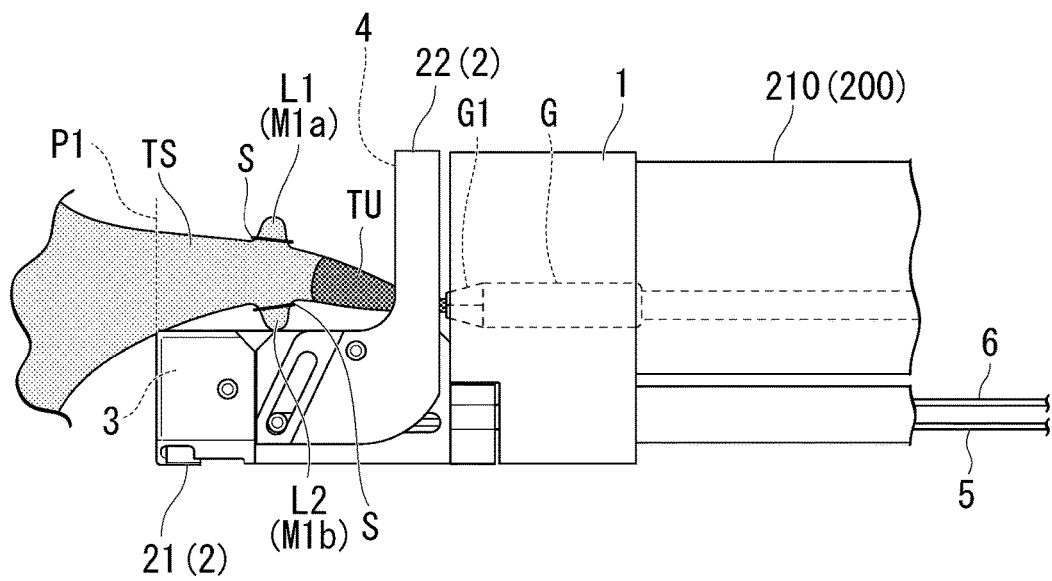
FIG. 56 is a view showing a retracting step in the modification example 2-2 of the resection method.
Figure 57:
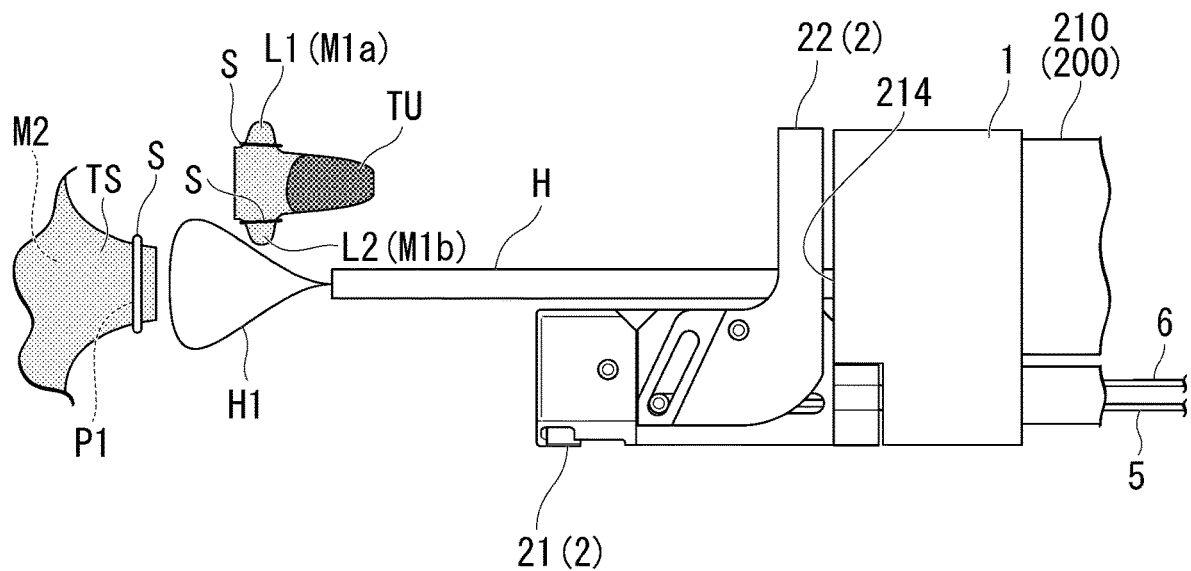
FIG. 57 is a view showing a resecting step in the modification example 2-2 of the resection method.

FIG. 54 is a flowchart showing the marking step in the modification example 2-2 of the resection method. FIG. 55 is a view showing the marking step in the modification example 2-2 of the resection method. FIG. 56 is a view showing the retracting step in the modification example 2-2 of the resection method. FIG. 57 is a view showing the resecting step in the modification example 2-2 of the resection method.

The marking step in the modification example 2-2 is the method adopted in the case in which the tumor TU is large. As shown in FIG. 54, in the marking step in the modification example 2-2, two of the three-dimensional markings are formed by the staple S.

The method of forming the three-dimensional marking of the modification example 2-2 is described based on the flowchart of FIG. 54. With regard to the disclosure same with the above-described second embodiment, the description will be omitted.

As shown in FIG. 54, the surgeon inserts the grasping forceps G into the treatment channel 230 (Step S421), determines the position of the grasping forceps G at the outside of the first part M1a of the peripheral tissues TS (Step S422), grasps the outside with respect to the first part M1a of the peripheral tissues TS by the grasping forceps G (Step S423), retracts the grasping forceps G (Step S424), makes the grasping portion 2 into the closed state (Step S425), forms the first three-dimensional marking L1 by ligating the peripheral tissues TS including the first part M1a of the peripheral tissues TS (Step S426), makes the grasping portion 2 into the open state (Step S427), and releases the grasping of the peripheral tissues TS (Step S428). The procedures up to this step are the same with that of the second embodiment.

Subsequently, the surgeon operates the endoscope 200 to determine the position by making the forceps portion G1 to approach the second part M1b of the peripheral tissues TS (FIG. 55) (Step S429). At this time, the surgeon determines the position of the forceps portion G1 at the outside of the tumor TU with respect to the position where the three-dimensional marking is desired to be formed.

Subsequently, the surgeon operates the grasping forceps G to press the forceps portion G1 to the outside of the second part M1b of the peripheral tissues TS and grapes the outside of the second part M1b of the peripheral tissues TS by the forceps portion G1 (Step S4210).

Here, the second part M1b of the peripheral tissues TS is the part positioned at the lower side of the peripheral tissues TS viewed in the visual field of the endoscope (the retraction direction of the grasping forceps G) when the grasping forceps G is retracted into the medical stapler 100 in the retracting step (FIG. 56) described below.

It is preferable that the second part M1b of the peripheral tissues TS is at the opposite side of the first part Mia of the peripheral tissues TS to sandwich the tumor TU therebetween.

Subsequently, the surgeon pulls the grasping forceps G to the hand side of the surgeon to retract the grasping forceps G (Step S4211) in the state in which the outside of the second part M1b of the peripheral tissues TS is grasped by the grasping forceps G. At this time, the surgeon pulls the distal end of the forceps portion G1 to the endoscope side (the proximal end side of the grasping forceps G and the hand side of the surgeon) with respect to the staple extraction portion 3.

Subsequently, similar to the procedures for forming the three-dimensional marking 11, the surgeon operates the open-close operation portion 250 to retract the open-close operation wire 5 and make the grasping portion 2 into the closed state (Step S4212). The surgeon clamps the peripheral tissues TS including the second part M1b thereof by the staple extraction portion 3 of the first grasping member 21 and the staple reception portion 4 of the second grasping member 22.

At this time, the surgeon confirms whether the tumor TU is retracted to the endoscope side with respect to the stapler extraction portion 3. In the case in which the tumor TU is retracted to the endoscope side with respect to the staple extraction portion 3, the surgeon operates the open-close operation portion 250 to retract the open-close operation wire 5 in the state in which the outside of the second part M1b of the peripheral tissues TS is grasped by the grasping forceps G to make the grasping portion 2 to be in the open state again. Thereafter, the surgeon operates the grasping forceps G to make the tumor TU into the state in which the tumor TU is at the endoscope side with respect to the staple extraction portion 3 of the first grasping member 21. Thereafter, the surgeon confirms that the tumor TU is not retracted to the endoscope side with respect to the staple extraction portion 3 and then operates the open-close operation portion 250 to retract the open-close operation wire 5 to make the grasping portion 2 into the closed state (Step S4212).

At this time, the surgeon determines the size of the three-dimensional marking L1 due to the volume of the peripheral tissues TS that is retracted into the medical stapler 100. In other words, when the grasping portion 2 is in the closed state, the second three-dimensional marking L2 is raised up and easy to be visually confirmed as the volume of the peripheral tissues disposed at the endoscope side with respect to the staple extraction portion 3 is large.

Subsequently, the surgeon operates the extraction operation portion 270 to pull the extraction operation wire 6 in the state in which the peripheral tissues TS including the second part M1b of the peripheral tissues TS is clamped by the staple extraction portion 3 and the staple reception portion 4 so as to eject the accommodated staple S toward the staple reception portion 4, as shown in FIG. 55, for ligating the second part M1b (Step S4213). Part of the peripheral tissues TS is raised up to form the second three-dimensional marking L2 by the ligating operation.

Subsequently, as shown in FIG. 55, the surgeon operates the open-close operation portion 250 to make the grasping portion 2 in the open state again (Step S4214). The surgeon opens the forceps portion G1 of the grasping forceps G to release the grasping with respect to the peripheral tissues TS including the second part M1b (Step S4215).

Here, it is described that the grasping forceps G is separated from the peripheral tissues TS after the peripheral tissues TS is ligated, however, the grasping forceps G may be separated from the peripheral tissues TS at any timing after the grasping portion is in the closed state (Step S4212).

In the above-described manner, the marking step is performed.

Subsequently, similar to the second embodiment, the procedures until the resection of the treatment T is performed. Only the different part in each step from the second embodiment will be disclosed.

<Retracting Step>

Subsequently, as shown in FIG. 56, the surgeon pulls the grasping forceps G grasping the tumor TU to the hand side in the visual field of the endoscope. At this time, the surgeon retracts the grasping forceps G such that the first three-dimensional marking L1 and the second three-dimensional marking L2 are at the proximal end side with respect to the staple extraction portion 3.

At this time, there is also the three-dimensional marking L2 formed at the second part M1b of the peripheral tissues TS such that it is possible to provide the resistance feeling (click feeling) to the surgeon when the second dimensional marking is on the second grasping member 22. Accordingly, it is possible to understand that the second three-dimensional marking L2 is disposed at the proximal end side with respect to the staple extraction portion 3 not only by the visual sense but also by the touch sense.

Subsequently, the surgeon operates the open-close operation portion 250 to retract the open-close wire 5 for making the grasping portion 2 into the closed state (Step S9). The surgeon clamps the ligation position P1 (see FIG. 56) positioned at the outside of the tumor TU with respect to the first part Mia and the second part M1b of the peripheral tissues TS in the peripheral tissues by the staple extraction portion 3 of the first grasping member 21 and the staple reception portion 4 of the second grasping member 22.

<Observing Step>

After the grasping portion 2 is in the closed state, the surgeon observes the positional relationship of the first grasping member, the first three-dimensional marking L1, and the second three-dimensional marking L2 in the visual field of the endoscope (Step S10).

According to the observation result, the surgeon determines whether the position grasped by the grasping portion 2 is appropriate (Step S11). If the position grasped by the grasping portion 2 is appropriate (Step S11; Yes), the following ligating step S12 is performed, and in the case in which the position grasped by the grasping portion 2 is inappropriate (Step S11; Yes), the adjustment of the grasping position is performed.

<Ligating Step>

The surgeon operates the extraction operation portion 270 to pull the extraction operation wire 6 in the state in which the ligation position P1 is clamped by the staple extraction portion 3 and the staple reception portion 4 so as to eject the accommodated staple S toward the staple reception portion 4 to ligate the ligation position P1 (Step S12).

<Resecting Step>

The surgeon removes the grasping forceps G from the treatment channel 230, inserts the high-frequency snare H as the resection treatment device (Step S14), and then protrudes the snare wire H1 disposed at the distal end of the high-frequency snare H from the forceps port 214. As shown in FIG. 57, the surgeon resects the part including the tumor TU at the proximal end side (the tumor TU side) with respect to the part ligated by the staple S and at the distal end side (the opposite side with respect to the tumor TU) with respect to the first part Mia and the second part M1b of the peripheral tissues TS. In other words, the surgeon resects the part including the tumor TU at the proximal end side (the tumor TU side) with respect to the part ligated by the staple S and at the distal end side (the opposite side with respect to the tumor TU) with respect to the positions where the first three-dimensional marking L1 and the second three-dimensional marking L2 are indwelled.

According to the method, there are two markings indicating the resection line at the time of resecting the peripheral tissues TS by the snare wire H1 such that it is easy to make the resection line to be stable.

Modification Example 2-3

Figure 58:
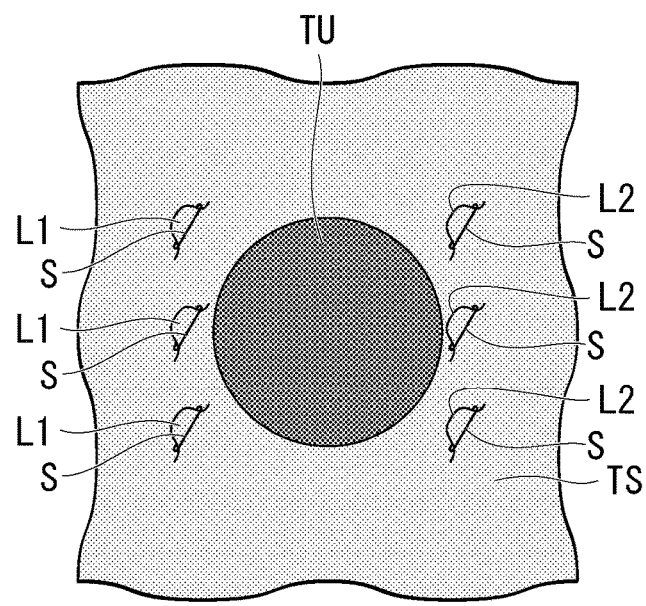
FIG. 58 is a view showing a marking step in a modification example 2-3 of the resection method.

FIG. 58 is a view showing a marking step in the modification example 2-3 of the resection method.

The marking step in the modification example 2-3 is adopted in the case in which the tumor TU is large, and a plurality of the three-dimensional markings L1 and a plurality of the three-dimensional markings L2 are formed by the staple S.

In the present modification example, among the peripheral tissue TS surrounding the tumor TU, triple of the three-dimensional markings L1 are formed at one side of the tumor TU while triple of the three-dimensional markings L2 are formed at the other side of the tumor TU. At this time, it is preferable to form the three-dimensional markings L1 and the three-dimensional markings L2 by a predetermined interval in accordance with the size of the tumor TU so as to recognize the range of the tumor TU.

In a case in which the tumor TU is large, it is possible to ligate the whole tumor TU by dividing the ligation into multiple times and to perform the resecting step by multiple times by performing the retracting step and the ligating step repeatedly for multiple times with respect to the tumor TU with the plurality of markings L1 and the plurality of markings L2 as visual marks. Accordingly, it is possible to resect the whole large tumor TU efficiently without any part left.

Third Embodiment

Figure 59:
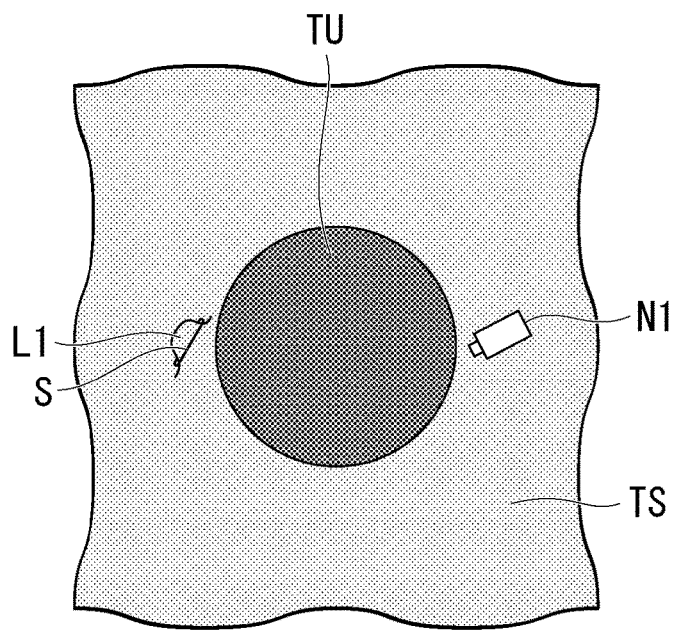
FIG. 59 is a view showing a marking step of a lesion resection method in a resection method according to a third embodiment of the present disclosure.

FIG. 59 is a view showing a marking step of a lesion resection method in the resection method according to the third embodiment of the present disclosure.

Figure 60:
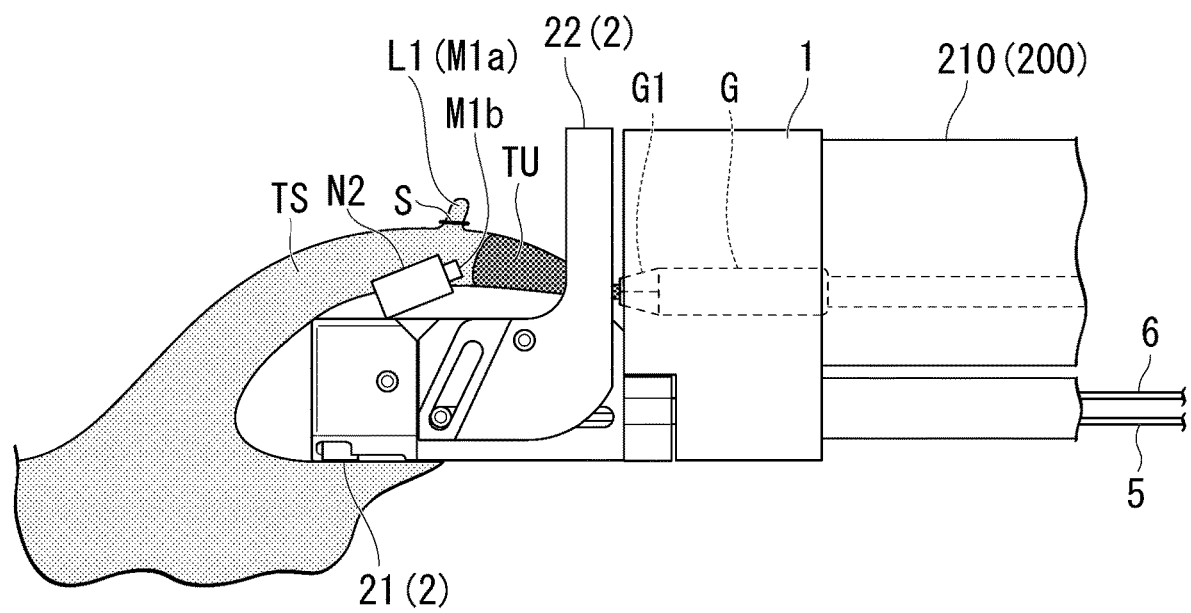
FIG. 60 is a view showing a retracting step of the resection method.

The third embodiment of the present disclosure will be described referring to FIG. 59 and FIG. 60. In the following description, the common configurations that have been described will be designated with the same references signs and the duplicate description will be omitted. The resection method according to the third embodiment, for example, is performed by using the medical system 300 shown in the first embodiment.

According to the present embodiment, in the marking step, a single three-dimensional marking MA by the clip N1 and a single three-dimensional marking L1 by the staple S are formed in the peripheral tissues TS surrounding the tumor TU such that there are totally tow of three-dimensional markings are applied. According to the present embodiment, the staple S is applied to the first part Mia of the peripheral tissues TS and the clip N1 is applied to the second part M1b.

Between the two of the three-dimensional markings, the three-dimensional marking MA is formed by using the clip N1 so as to be easy to see and it is possible to provide the resistance feeling (click feeling) to the surgeon, and it is possible to understand that the clip N1 is disposed at the hand side of the endoscope 200 with respect to the staple extraction portion 3 not only by the visual sense but also by the touch sense. Also, one of the two three-dimensional markings is the three-dimensional marking L1 by the staple S such that it is possible to reduce the number of the clip N1 being used to reduce the cost.

Figure 61:
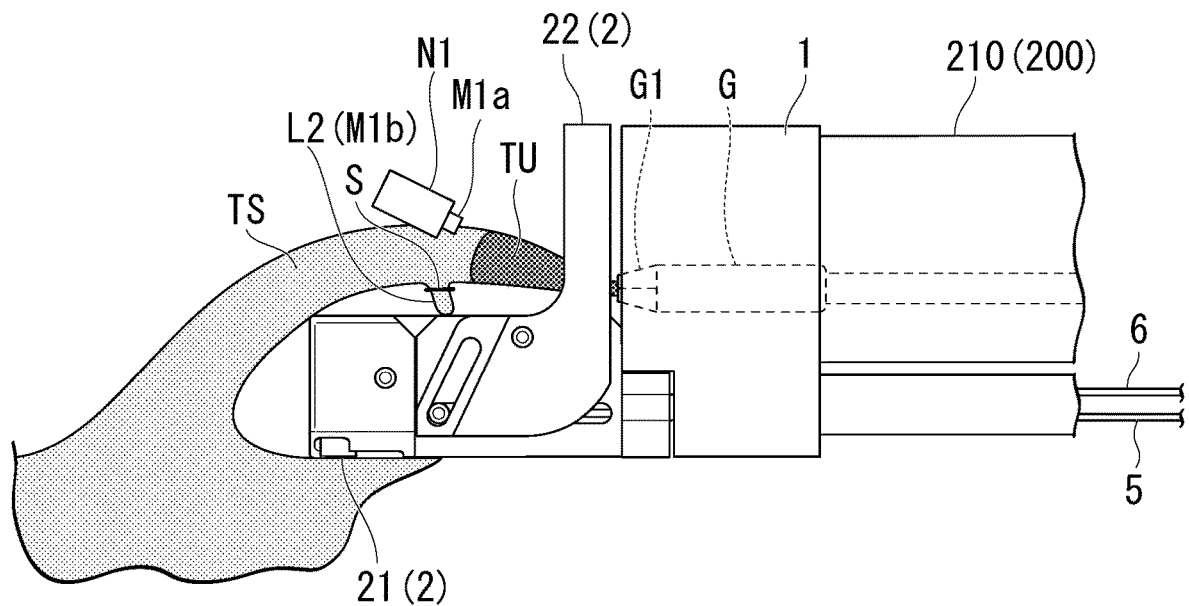
FIG. 61 is a view showing another example of the retracting step of the resection method.

FIG. 61 is a view showing another example of the retracting step of the resection method.

According to the embodiment, in the peripheral tissues TS, the three-dimensional marking L1 by the staple S is applied to the first part Mia, and the three-dimensional marking MA by the clip N1 is applied to the second part M1b. However, the present embodiment is not limited to the configuration, for example, as shown in FIG. 61, the three-dimensional marking MA by the clip N1 may be applied to the first part Mia and the three-dimensional marking L1 by the staple S may be applied to the second part M1b.

Accordingly, during the retracting step, the clip N1 does not interfere the first grasping member 21 of the grasping portion 2 such that it is possible to smoothly retract the tumor TU to the endoscope side.

Modification Example 3-1

Figure 62:
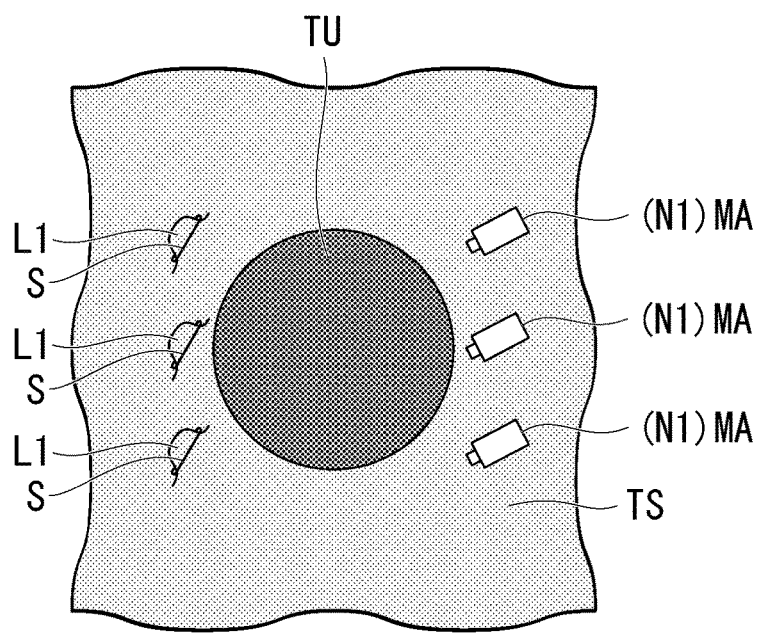
FIG. 62 is a view showing a marking step in a modification example 3-1 of the resection method.

FIG. 62 is a view showing a marking step in the modification example 3-1 of the resection method.

The marking step in the modification example 3-1 is adopted in the case when the tumor TU is large.

In the modification example 3-1, a plurality of the three-dimensional markings MA by the staples S and a plurality of the three-dimensional markings L1 by the first clip N1 are formed respectively.

In the present modification example, among the peripheral tissue TS surrounding the tumor TU, triple of the three-dimensional markings L1 are formed at one side of the tumor TU while triple of the three-dimensional markings MA are formed at the other side of the tumor TU. At this time, it is preferable to form the three-dimensional markings L1 and the three-dimensional markings MA by a predetermined interval in accordance with the size of the tumor TU so as to recognize the range of the tumor TU.

In a case in which the tumor TU is large, it is possible to ligate the whole tumor TU by dividing the ligation into multiple times and to perform the resecting step by multiple times by performing the retracting step and the ligating step repeatedly for multiple times with respect to the tumor TU with the plurality of markings L1 and the plurality of markings MA as visual marks. Accordingly, it is possible to resect the whole large tumor TU efficiently without any part left.

What is claimed is:

1. A lesion resection method, comprising:
   a marking step of forming a three-dimensional marking in peripheral tissues of a lesion;
   a grasping step of grasping the lesion by a grasping forceps;
   a retracing step of pulling the marking to a hand side of a staple ejection position of a stapler by pulling the grasping forceps grasping the lesion;
   a ligating step of ejecting a staple from the stapler to ligate the peripheral tissues of the lesion; and
   a resecting step of resecting the lesion.

2. The lesion resection method according to claim 1, wherein in the resecting step, tissues between a ligation position by the staple and the marking is resected to resect the lesion.

3. The lesion resection method according to claim 1, further comprising:
   a collecting step of grasping tissues including the resected lesion by the grasping forceps and removes the grasping forceps to collect the resected lesion.

4. The lesion resection method according to claim 1, wherein the marking step including:
   a first marking step of forming the marking in a first part of the peripheral tissues; and
   a second marking step of forming the marking in a second part of the peripheral tissues.

5. The lesion resection method according to claim 4, wherein the lesion resection method is performed by being observed in an endoscopic visual field,
   the first part is disposed on an upper side of the lesion in the endoscopic visual field in the retracting step, and
   the second part is disposed on a lower side of the lesion in the endoscopic visual field in the retracting step.

6. The lesion resection method according to claim 5, wherein at least one three-dimensional marking is formed in the first marking step.

7. The lesion resection method according to claim 6, wherein the three-dimensional marking is formed by indwelling a clip, and the clip is indwelled such that a distal end of the clip is directed to a direction separating from the lesion.

8. The lesion resection method according to claim 5, wherein at least one planar marking is disposed in the second marking step.

9. The lesion resection method according to claim 5, wherein at least one three-dimensional marking is disposed in the second marking step.

10. The lesion resection method according to claim 9,
wherein the three-dimensional marking is formed by indwelling a clip, and
the clip is indwelled such that a distal end of the clip is directed to a direction approaching the lesion.

11. The lesion resection method according to claim 1, wherein the marking step includes forming the three-dimensional marking by disposing a clip.

12. The lesion resection method according to claim 11, wherein in the marking step, the clip is disposed such that a distal end of the clip is directed to a direction approaching the lesion.

13. The lesion resection method according to claim 11, wherein in the marking step, the clip is disposed such that a distal end of the clip is directed to a direction separating from the lesion.

14. The lesion resection method according to claim 1, wherein the marking step includes forming the three-dimensional marking by raising up and ligating the peripheral tissues.

* * * * *